(12) United States Patent
Reddy et al.

(10) Patent No.: US 8,669,259 B2
(45) Date of Patent: Mar. 11, 2014

(54) HETEROCYCLIC AMIDE COMPOUNDS AS PROTEIN KINASE INHIBITORS

(75) Inventors: Panduranga P. Adulla Reddy, Walpole, MA (US); M. Arshad Siddiqui, Newton, MA (US); Tzu Tshin Wong, Belmont, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/391,402

(22) PCT Filed: Aug. 19, 2010

(86) PCT No.: PCT/US2010/045994
§ 371 (c)(1),
(2), (4) Date: Apr. 12, 2012

(87) PCT Pub. No.: WO2011/025706
PCT Pub. Date: Mar. 3, 2011

(65) Prior Publication Data
US 2012/0208826 A1     Aug. 16, 2012

Related U.S. Application Data

(60) Provisional application No. 61/237,009, filed on Aug. 26, 2009.

(51) Int. Cl.
*A61K 31/496*     (2006.01)
*C07D 401/04*     (2006.01)

(52) U.S. Cl.
USPC ..................... 514/253.01; 544/360

(58) Field of Classification Search
USPC ........................ 544/364; 514/253.1
See application file for complete search history.

(56) References Cited

U.S. PATENT DOCUMENTS

| 6,960,594 | B2 | 11/2005 | Labrecque et al. | |
| 7,015,218 | B1 * | 3/2006 | Ushio et al. | 514/227.8 |
| 2008/0076777 | A1 | 3/2008 | Cassayre et al. | |
| 2010/0331313 | A1 * | 12/2010 | Reddy et al. | 514/218 |

FOREIGN PATENT DOCUMENTS

| EP | 2009005 A1 | | 12/2008 |
| JP | 2002161084 | * | 6/2002 |
| WO | 2005100351 A1 | | 10/2005 |
| WO | 2006012642 A2 | | 2/2006 |
| WO | 2007022258 A1 | | 2/2007 |
| WO | 2008054605 A2 | | 5/2008 |
| WO | 2008054749 A1 | | 5/2008 |
| WO | WO2008054749 | * | 5/2008 |
| WO | WO2009017701 | * | 2/2009 |
| WO | WO2009058728 | * | 5/2009 |

* cited by examiner

*Primary Examiner* — Yong Chu
*Assistant Examiner* — Karen Cheng
(74) *Attorney, Agent, or Firm* — Richard S. Parr; Laura M. Ginkel

(57) ABSTRACT

The present invention relates to heterocyclic amide derivatives of Formula (I): Formula (I) wherein the variables are as defined in the specification. The present invention further relates to compositions comprising said heterocyclic amide derivatives of formula (I) and methods for using said heterocyclic amide derivatives of formula (I) for treating or preventing a disease or disorder related to the activity of a protein kinase, in particular, a proliferative disease, an anti-proliferative disorder, inflammation, arthritis, a neurological or neurodegenerative disease, a cardiovascular disease, alopecia, a neuronal disease, an ischemic injury, a viral disease or a fungal infection.

(I)

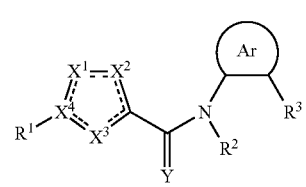

18 Claims, No Drawings

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:

<223> OTHER INFORMATION: This peptide substrate for Akt1, Aurora A, Aurora B, Aurora C, PAK2, PKA and PKG is TAMRA (Abs/Em = 541/565 nm) labeled on the N-terminus.

<400> SEQUENCE: 1

Gly Arg Thr Gly Arg Arg Asn Ser Ile
1               5

HETEROCYCLIC AMIDE COMPOUNDS AS PROTEIN KINASE INHIBITORS

CROSS REFERENCE TO RELATED APPLICATIONS

This application is a U.S. National Phase application under 35 U.S.C. §371 of PCT Application Number, PCT/US2010/045994, filed Aug. 19, 2010, which claims priority from U.S. Provisional Application Ser. No. 61/237,009, filed Aug. 26, 2009.

SEQUENCE LISTING

The sequence listing submitted via EFS, in compliance with 37 CFR §1.52(e)(5), is incorporated herein by reference. The sequence listing text file submitted via EFS contains the file "OC20097047USPCT-SEQTXT-25APR2012" created on Apr. 25, 2012, which is 578 bytes in size.

FIELD OF THE INVENTION

The present invention relates to compounds useful as protein kinase inhibitors, regulators or modulators, pharmaceutical compositions comprising the compounds, and methods of treatment using the compounds and compositions to treat various diseases such as cancer, inflammation, arthritis, viral diseases, neurodegenerative diseases such as Alzheimer's disease, cardiovascular diseases, and fungal diseases.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (Chk) (e.g., CHK-1, CHK-2 etc.) kinases, AKT kinases, PDK-1, JNK, and the like. Examples of protein kinase inhibitors are described in WO02/22610 A1 and by Y. Mettey et al., in *J. Med. Chem.*, 46:222-236 (2003).

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1S, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al., *J. Clin. Oncol.* 16:2986-2999 (1998).

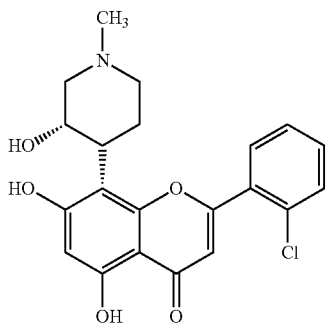

Other known inhibitors of CDKs include, for example, olomoucine (J. Vesely et al., *Eur. J. Biochem.*, 224:771-786 (1994)) and roscovitine (I. Meijer et al., *Eur. J. Biochem.*, 243:527-536 (1997)). U.S. Pat. No. 6,107,305 describes certain pyrazolo[3,4-b]pyridine compounds as CDK inhibitors. An illustrative compound from the '305 patent is:

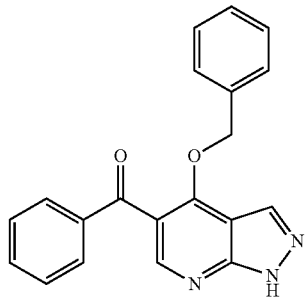 [SMILES: O=C(c1ccccc1)c1cnc2[nH]ncc2c1OCc1ccccc1]

K. S. Kim et al., *J. Med. Chem.* 45:3905-3927 (2002) and WO 02/10162 disclose certain aminothiazole compounds as CDK inhibitors.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G.sub.2 arrest induced by DNA damage inflicted by either anticancer agents or endogenous DNA damage, as well as result in preferential killing of the resulting checkpoint defective cells. See, e.g., Peng et al., *Science*, 277:1501-1505 (1997); Sanchez et al., *Science*, 277:1497-1501 (1997); Nurse, *Cell*, 91:865-867 (1997); Weinert, *Science*, 277:1450-1451 (1997); Walworth et al., *Nature*, 363:368-371 (1993); and Al-Khodairy et al., *Molec. Biol.* Cell., 5:147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, 395:507-510 (1998); Matsuoka, *Science*, 282:1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HERS and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1(FLK-1), fetal liver kinase-4 (FLK-4) and the fms-like tyrosine kinase-1 (fit-1). For detailed discussion of the receptor-type tyrosine kinases, see Plowman et al., *DN&P* 7(6):334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8:2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lek, Blk, Hck, Fgr, and Yrk. The Src subfamily of enzymes has been linked to oncogenesis. For a more detailed discussion of the non-receptor type of tyrosine kinases, see Bolen, *Oncogene*, 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Res.*, 56:3540-3545 (1996)), as has been shown with mutants of VEGF-R2 which fail to mediate signal transduction. Millauer et al, *Cancer Res.*, 56:1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57: 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, 17:5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277:55-60 (1997).

The kinase, JNK, belongs to the mitogen-activated protein kinase (MAPK) superfamily. JNK plays a crucial role in inflammatory responses, stress responses, cell proliferation, apoptosis, and tumorigenesis. JNK kinase activity can be activated by various stimuli, including the proinflammatory cytokines (TNF-alpha and interleukin-1), lymphocyte costimulatory receptors (CD28 and CD40), DNA-damaging chemicals, radiation, and Fas signaling. Results from the JNK knockout mice indicate that JNK is involved in apoptosis induction and T helper cell differentiation.

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa—Tom. 616, (Aug. 30, 2005), http://kirjasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (see Bischoff et al., EMBO J., 17:3052-3065 (1998); Schumacher et al., *J. Cell Biol.* 143:1635-1646 (1998); Kimura et al., *J. Biol. Chem.*, 272:13766-13771 (1997)).

c-Met is a proto-oncogene that encodes for a tyrosine kinase receptor for hepatocyte growth factor/scatter factor (HGF/SF). The c-Met protein is expressed mostly in epithelial cells, and due to its function it is also known as hepatocyte growth factor receptor, or HGFR. When HGF/SF activates c-Met, the latter in turn may activate a number of kinase pathways, including the pathway from Ras to Raf to Mek to the mitogen-activated protein kinase ERK1 to the transcription factor ETS1. Met signaling has been implicated in the etiology and malignant progression of human cancers (see Birchmeier et al., *Nature Reviews Molecular Cell Biology*, 4:915-925 (2003); Zhang et al., *Journal of Cellular Biochemistry*, 88:408-417 (2003); and Paumelle et al., *Oncogene*, 21:2309-2319 (2002)).

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes PKA, PKB (c-Akt), PKC, PRK1, 2, $p70^{S6K}$, and PDK.

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J. Neurosci.* 2000, 20, 2875-2886,)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 1997, 17, 1595-1606,); (Hemmings, B. A., *Science*, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. O. et al., *Proc. Natl. Acad. Sci. U.S.A.* 1992, 89, 9267-9271). It has also been found to be overexpressed in 12% of pancreatic cancers (Cheng, J. O. et al., *Proc. Natl. Acad. Sci. U.S.A.* 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer* 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.* 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., *Recent Prog. Horm. Res.* 1988, 44, pp. 307). Three isoforms of the catalytic subunit (C-α, C-β and C-γ) have been reported to date (Beebe, S. J. et al., *J. Biol. Chem.* 1992, 267, 25505-25512) with the C-α subunit being the most extensively studied, primarily because of its elevated expression in primary and metastatic melanomas (Becker, D. et al., *Oncogene* 1990, 5, 1133). To date, strategies to modulate the activity of the C-α subunit involve the use of antibodies, molecules that block PKA activity by targeting regulatory dimers and antisense oligonucleotides expression.

The ribosomal protein kinases $p70^{S6K}$-1 and -2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). $p70^{S6K}$ dependent S6 phosphorylation is stimulated in response to a variety of hormones and growth factors primarily via the PI3K pathway (Coffer, P. J. et al., *Biochem. Biophys. Res. Commun,* 1994 198, 780-786), which may be under the regulation of mTOR, since rapamycin acts to inhibit $p70^{S6K}$ activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.*, 1998, 8, 69-81). The use of rapamycin and gene deletion studies of dp70S6K from *Drosophila* and p70$^{S6K}$1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frodin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70), PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of P13K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.*, 1997 57, 5221-5225), (Brognard, J. et al., *Cancer Res.*, 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer Ther.* 2002, 1, 707), colon [(*Neoplasia* 2001, 3, 278), (Arica, S. et al., *J. Biol. Chem.* 2002, 277, 27613-27621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biot.* 2000, 10, 1439-1442)].

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNFα), interleukin 6 (IL-6) and interferon gamma (IFNg), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α (see Deak et al., *EMBO*. 17:4426-4441 (1998); Shi et al., *Biol. Chem.* 383:1519-1536 (2002); Staklatvala., *Curr. Opin. Pharmacol.* 4:372-377 (2004); and Shiroto et al., *J. Mol. Cell Cardiol.* 38:93-97 (2005)).

Published patent application U.S. 20070043045 relates to novel high-affinity thiophene-based and furan-based kinase ligands, useful for the treatment of diseases associated with the activity of protein kinases.

International Publication WO 2007/123269 relates to azolecarboxamide derivatives useful for treatment of lower urinary tract disease or various diseases accompanied by pain.

International Publications WO 2008/054701, WO 2008/054702 and WO 2008/054749 relate to 2-aminothiazole-4-carboxylic acid amides as protein kinase inhibitors useful for the treatment of diseases associated with the activity of protein kinases.

There is a need for effective inhibitors of protein kinases in order to treat or prevent disease states associated with abnormal cell proliferation. Moreover, it is desirable for kinase inhibitors to possess both high affinities for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF (VEGF-R2), Pim-1, PDK-1, CDKs or CDK/cyclin complexes and both receptor and non-receptor tyrosine kinases.

SUMMARY OF THE INVENTION

In its many embodiments, the present invention provides a novel class of heterocyclic amide derivatives, pharmaceutical compositions comprising one or more of said compounds, and methods for using said compounds for treating or preventing a proliferative disease, an anti-proliferative disorder, inflammation, arthritis, a neurological or neurodegenerative disease, a cardiovascular disease, alopecia, a neuronal disease, an ischemic injury, a viral disease or a fungal disease.

Accordingly, in one aspect, the present invention provides a heterocyclic amide derivative of Formula (I):

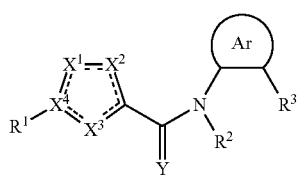

Formula (I)

wherein

Ar is $C_{6-10}$ arylene or a 5-10 membered heteroarylene comprising one ring or two rings fused together at adjacent ring atoms, and comprising 1-3 heteroatoms independently selected from O, S and N, said $C_{6-10}$arylene and 5-10 membered heteroarylene being joined to $NR^2$ and $R^3$ via any two adjacent ring carbons on said $C_{6-10}$arylene and 5-10 membered heteroarylene, and being optionally substituted with one or more substituents independently selected from $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^4$, —$S(O)R^4$, —$S(O)_2R^4$, —$COR^4$, —$CO_2R^4$, —$CONHR^4$, —$CON(R^4)_2$, —$NHCOR^4$, CN and $NO_2$, wherein said $C_{1-6}$alkyl, $C_{3-8}$cycloalkyl and $C_{1-6}$alkyloxy are optionally substituted with one or more halogens and wherein said $C_{6-10}$aryl and $C_{6-10}$aryloxy are optionally substituted with one or more substituent independently selected from halogen, hydroxyl, $C_{1-6}$alkyl and $C_{1-6}$alkyloxy;

$R^1$ is $CONR^5R^6$, $NR^7COR^8$, $C_{6-10}$aryl or a 4-10 membered saturated or unsaturated heterocyclic ring system comprising one ring or two rings fused together at adjacent ring atoms and comprising a N atom and optionally comprising one or more further heteroatomic moiety independently selected from O, S and $N(R^{1a})_m$, said $C_{6-10}$aryl and 4-10 membered saturated or unsaturated heterocyclic ring system being optionally substituted with one or more substituent independently selected from $C_{1-6}$alkyl, $C_{3-8}$cycloalkyl, $C_{1-6}$alkyloxy, hydroxy$C_{1-6}$alkoxy, $C_{1-2}$alkoxy$C_{1-6}$alkoxy, $(C_{1-6}$alkyl$)_2$-N—$C_{1-6}$alkoxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^9$, —$S(O)R^9$, —$S(O)_2R^9$, —$COR^9$, —$CO_2R^9$, —$CON(R^9)_2$, —$NHCOR^9$, CN and $NO_2$, or two substituents on the same carbon form together with said carbon a carbonyl, wherein said $C_{1-6}$alkyl, $C_{3-8}$cycloalkyl and $C_{1-6}$alkyloxy are optionally substituted with one or more halogens and wherein said $C_{6-10}$aryl and $C_{6-10}$aryloxy are optionally substituted with 1-2 substituents independently selected from halogen, hydroxyl, $C_{1-6}$alkyl and $C_{1-6}$alkyloxy;

$R^{1a}$ is H or $C_{1-6}$alkyl;

$R^2$ is H or $C_{1-6}$alkyl;

$R^3$ is $C_{6-10}$aryl or a 4-12 membered saturated or unsaturated heterocyclic ring system comprising one ring or two rings fused together at adjacent ring atoms or comprising two rings linked together at the same ring atom thereby forming a spirocyclic ring, said 4-12 membered heterocyclic ring system comprising a N atom and optionally comprising one or more further heteroatomic moiety independently selected from O, S and $N(R^{3a})_n$, said $C_{6-10}$aryl and 4-12 membered saturated or unsaturated heterocyclic ring system being optionally substituted with one or more substituent independently selected from $C_{1-6}$alkyl optionally substituted with hydroxyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^{10}$, —$S(O)R^{10}$, —$S(O)_2R^{10}$, —$COR^{10}$, —$CO_2R^{10}$, —$CON(R^{10})_2$, —$NHCOR^{10}$, CN and $NO_2$, or two substituents on the same carbon form together with said carbon a carbonyl, wherein said $C_{1-6}$alkyl and $C_{1-6}$ alkyloxy are optionally substituted with one or more halogens and wherein said $C_{6-10}$aryl and $C_{6-10}$aryloxy are optionally substituted with 1-2 substituents independently selected from halogen, hydroxyl, $C_{1-6}$alkyl and $C_{1-6}$alkyloxy;

$R^{3a}$ is H or $C_{1-6}$alkyl;

each $R^4$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatomic moiety independently selected from O, S and $N(R^{4a})_p$, said $C_{1-6}$alkyl, $C_{3-8}$cycloalkyl, $C_{1-6}$alkyloxy and $C_{3-8}$cycloalkyloxy being optionally substituted with one or more halogen and said $C_{6-10}$aryl, $C_{6-10}$aryloxy and 4-7 membered saturated or unsaturated heterocyclic ring being optionally substituted with one or more substituent independently selected from halogen, hydroxyl, $C_{1-6}$alkyl and $C_{1-6}$alkyloxy;

$R^{4a}$ is H or $C_{1-6}$alkyl;

$R^5$ and $R^6$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatomic moiety independently selected from O, S and $N(R^{5a})_q$, said $C_{1-6}$alkyl and $C_{3-8}$cycloalkyl being optionally substituted with one or more halogens and said $C_{6-10}$aryl, $C_{6-10}$aryl$C_{1-2}$alkyl and 4-10 membered saturated or unsaturated heterocyclic ring system being optionally substituted with one or more substituent independently selected from halogen, hydroxyl, $C_{1-6}$alkyl and $C_{1-6}$alkyloxy or $R^5$ and $R^6$ together with the N to which they are bonded form a 4-7 membered heterocyclic ring optionally comprising a further hetroatomic moiety selected from O, S and $N(R^{6a})_r$;

$R^{5a}$ and $R^{6a}$ are independently H or $C_{1-6}$alkyl;

$R^7$ and $R^8$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatomic moiety independently selected from O, S and $N(R^{7a})_s$, said $C_{1-6}$alkyl and $C_{3-8}$cycloalkyl being optionally substituted with one or more halogens and said $C_{6-10}$aryl, $C_{6-10}$aryl$C_{1-2}$alkyl and 4-10 membered saturated or unsaturated heterocyclic ring system being optionally substituted with one or more substituent independently selected from halogen, hydroxyl, $C_{1-6}$alkyl and $C_{1-6}$alkyloxy;

$R^{7a}$ is H or $C_{1-6}$alkyl;

each $R^9$ is independently $C_{1-6}$alkyl, $C_{3-6}$cycloalkyl, $C_{1-6}$alkyloxy, $C_{3-6}$cycloalkyloxy, $C_{6-10}$aryl, $C_{6-10}$aryloxy or a 4-7 membered saturated or unsaturated heterocyclic ring comprising one or more heteroatomic moiety independently selected from O, S and $N(R^{9a})_t$, said $C_{1-6}$alkyl, $C_{3-6}$cycloalkyl, $C_{1-6}$alkyloxy and $C_{3-6}$cycloalkyloxy being optionally substituted with one or more halogen and said $C_{6-10}$aryl, $C_{6-10}$aryloxy and 4-7 membered saturated or unsaturated heterocyclic ring being optionally substituted with one or more substituent selected from halogen, hydroxyl, $C_{1-6}$alkyl and $C_{1-6}$alkyloxy;

$R^{9a}$ is H or $C_{1-6}$alkyl;

each $R^{10}$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatomic moiety independently selected from O, S and $N(R^{10a})_u$, said $C_{1-6}$alkyl, $C_{3-8}$cycloalkyl, $C_{1-6}$alkyloxy and $C_{3-8}$cycloalkyloxy being optionally substituted with one or more halogen and said $C_{6-10}$aryl, $C_{6-10}$aryloxy and 4-7 membered saturated or unsaturated heterocyclic ring being optionally substituted with one or more substituent selected from halogen, hydroxyl, $C_{1-6}$alkyl and $C_{1-6}$alkyloxy;

$R^{10a}$ is H or $C_{1-6}$alkyl;

X1, X2 and X3 are independently selected from O, S, $CR^{11}$ or $N(R^{11})_v$, with the provisos that (i) no more than one of X1, X2 and X3 is O or S;

(ii) when one of X1, X2 and X3 is N, then the other two are not S; and (iii) when one of X1, X2 and X3 is O or S and the other two are $CR^{11}$, then Ar cannot be $C_{6-10}$arylene;

each $R^{11}$ is independently H, $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatomic moiety independently selected from O, S and $N(R^{11a})_w$, said $C_{1-6}$alkyl, $C_{3-8}$cycloalkyl, $C_{1-6}$alkyloxy and $C_{3-8}$cycloalkyloxy being optionally substituted with one or more halogen and said $C_{6-10}$aryl, $C_{6-10}$aryloxy and 4-7 membered saturated or unsaturated heterocyclic ring being optionally substituted with one or more substituent selected from halogen, hydroxyl, $C_{1-6}$alkyl and $C_{1-6}$alkyloxy;

$X^4$ is N or C;

Y is O, S or $-NR^{12}$;

$R^{12}$ is H or $C_{1-4}$alkyl; and m, n, p, q, r, s, t, u, v and w are independently 0 or 1;

or a pharmaceutically acceptable salt, solvate, ester or prodrug thereof.

In one aspect, the heterocyclic amide derivatives of Formula (I) can be useful as protein kinase inhibitors.

In another aspect, the heterocyclic amide derivatives of Formula (I) can be useful for treating or preventing proliferative disease, an anti-proliferative disorder, inflammation, arthritis, a neurological or neurodegenerative disease, a cardiovascular disease, alopecia, a neuronal disease, an ischemic injury, a viral disease or a fungal disease (each being a "Condition").

In another aspect, the present invention provides pharmaceutical compositions comprising at least one heterocyclic amide derivative of Formula (I) and a pharmaceutically acceptable carrier. The compositions can be useful for treating or preventing a Condition in a patient.

In still another aspect, the present invention provides methods for treating a Condition in a patient, the method comprising administering to a patient an effective amount of at least one heterocyclic amide derivative of Formula (I).

In another aspect, the present invention provides methods for treating a cancer in a patient, the method comprising administering to a patient an effective amount of at least one heterocyclic amide derivative of Formula (I) and at least one additional anticancer agent which is not a heterocyclic amide derivative of Formula (I).

DETAILED DESCRIPTION OF THE INVENTION

In an embodiment, the present invention provides compounds of Formula (I) and or pharmaceutically acceptable salts and solvates thereof. The compounds of formula I can be useful for treating or preventing a Condition in a patient.

As used above, and throughout this disclosure, the following terms, unless otherwise indicated, shall be understood to have the following meanings:

"Patient" includes both human and animals.

"Mammal" means humans and other mammalian animals.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl. "$C_{1-6}$alkyl" represents an aliphatic hydrocarbon group which may be straight or branched and comprising 1 to 6 carbon atoms in the chain. Branched means that one or more alkyl group such as methyl, ethyl or propyl, is attached to a linear alkyl chain. Non-limiting examples of suitable $C_{1-6}$alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "$C_{6-10}$aryl" represents an aromatic monocyclic or multicyclic ring system comprising 6 to 10 carbon atoms and at least one aromatic ring. Non-limiting examples of suitable $C_{6-10}$aryl groups include phenyl and naphthyl.

"$C_{6-10}$arylene" represents a disubstituted aromatic monocyclic or multicyclic ring system comprising 6 to 10 carbon atoms and at least one aromatic ring.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. "$C_{3-8}$cycloalkyl" represents a non-aromatic mono- or multicyclic ring system comprising 3 to 8 carbon atoms, preferably 3 to 6 carbon atoms. Non-limiting examples of suitable monocyclic $C_{3-8}$cycloalkyls include cyclopropyl, cyclopentyl, cyclohexyl, cycloheptyl and the like. "$C_{3-8}$cycloalkyloxy" represents a $C_{3-8}$cycloalkyl-O— group in which the $C_{3-8}$cycloalkyl group is as previously described. Non-limiting examples of suitable $C_{3-8}$cycloalkyloxy groups include cyclopropyloxy, cyclopentyloxy, cyclohexyloxy and cycloheptyloxy. The bond to the parent moiety is through the ether oxygen.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

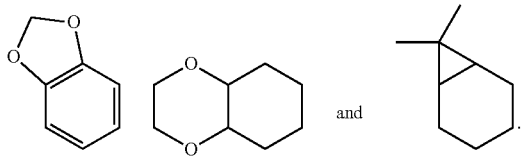

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like. "Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

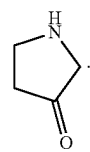

"Heterocyclylalkyl" means a heterocyclyl moiety as defined above linked via an alkyl moiety (defined above) to a parent core. Non-limiting examples of suitable heterocyclyialkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

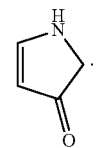

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

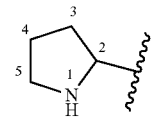

there is no —OH attached directly to carbons marked 2 and 5.

It should also be noted that tautomeric forms such as, for example, the moieties:

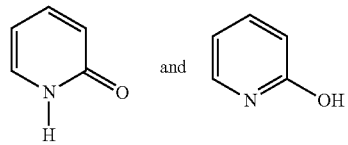 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen. "$C_{1-6}$alkyloxy" represents a $C_{1-6}$alkyl-O— group in which the $C_{1-6}$alkyl group is as previously described. Non-limiting examples of suitable $C_{1-6}$alkyloxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen. "$C_{6-10}$aryloxy" represents a $C_{6-10}$aryl-O— group in which the $C_{6-10}$aryl group is as previously described. Non-limiting examples of suitable $C_{6-10}$aryloxy groups include phenoxy and naphthyloxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidine-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I-IX, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) contains an alcohol functional group, a prodrug can be formed by the replacement of the hydrogen atom of the alcohol group with a group such as, for example, $C_{1-6}$alkanoyloxymethyl, 1-($C_{1-6}$alkanoyloxy)ethyl, 1-methyl-1-($C_{1-6}$alkanoyloxy)ethyl, $C_{1-6}$alkoxycarbonyloxymethyl, N—$C_{1-6}$alkoxycarbonylaminomethyl, succinoyl, $C_{1-6}$alkanoyl, $\alpha$-amino$C_{1-4}$alkanyl, arylacyl and $\alpha$-aminoacyl, or $\alpha$-aminoacyl-$\alpha$-aminoacyl, where each $\alpha$-aminoacyl group is independently selected from the naturally occurring L-amino acids, $P(O)(OH)_2$, —$P(O)(OC_{1-6}alkyl)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $C_{1-10}$alkyl, $C_{3-7}$cycloalkyl, benzyl, or R-carbonyl is a natural $\alpha$-aminoacyl or natural $\alpha$-aminoacyl, —C(OH)C(O)O$Y^1$ wherein $Y^1$ is H, $C_{1-6}$alkyl or benzyl, —C(O$Y^2$)$Y^3$ wherein $Y^2$ is $C_{1-4}$ alkyl and $Y^3$ is $C_{1-6}$alkyl, carboxy $C_{1-6}$alkyl, amino$C_{1-4}$alkyl or mono-N— or di-N,N—$C_{1-6}$alkylaminoalkyl, —C($Y^4$)$Y^5$ wherein $Y^4$ is H or methyl and $Y^6$ is mono-N— or di-N,N—$C_{1-6}$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I-IX can form salts which are also within the scope of this invention. Reference to a compound of Formula I-IX herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I-IX contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I-IX may be formed, for example, by reacting a compound of Formula I-IX with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g, methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I-IX, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I-IX, and of the salts, solvates, esters and prodrugs of the compounds of Formula I, are intended to be included in the present invention.

Heterocyclic Amide Compounds of the Invention

In one embodiment of the present invention, Ar is $C_{6-10}$arylene optionally substituted with one or more substituents independently selected from $C_{1-6}$alkyl, $C_{3-8}$cycloalkyl, $C_{1-6}$alkyloxy, $C_{3-8}$cycloalkyloxy, $C_{6-10}$aryloxy, halogen, hydroxyl, $NH_2$, —$NHC_{1-6}$alkyl, —$N(C_{1-6}$alkyl$)_2$, —$SR^4$, —$S(O)R^4$, —$S(O)_2R^4$, —$COR^4$, —$CO_2R^4$, —$CONHR^4$, —$CON(R^4)_2$, —$NHCOR^4$, CN and $NO_2$, wherein said $C_{1-6}$alkyl and $C_{1-6}$alkyloxy are optionally substituted with one or more halogens and wherein $R^4$ has the previously defined meanings.

In another embodiment, Ar is $C_{6-10}$arylene optionally substituted with one or more substituents independently selected from $C_{1-6}$alkyl, $C_{1-6}$alkyloxy and halogen.

In another embodiment, Ar is $C_{6-10}$arylene optionally substituted with methyl, ethyl, methoxy, ethoxy, fluoro or chloro.

In another embodiment of the present invention, Ar is a 5-11 membered heteroarylene system comprising 1-3 heteroatoms independently selected from O, S and N, said heteroarylene system being optionally substituted with one or more substituents independently selected from $C_{1-6}$alkyl, $C_{3-8}$cycloalkyl, $C_{1-6}$alkyloxy, $C_{3-8}$cycloalkyloxy, $C_{6-10}$aryloxy, halogen, hydroxyl, $NH_2$, —$NHC_{1-6}$alkyl, —$N(C_{1-6}alkyl)_2$, —$SR^4$, —$S(O)R^4$, —$S(O)_2R^4$, —$COR^4$, —$CO_2R^4$, —$CONHR^4$, —$CON(R^4)_2$, —$NHCOR^4$, CN and $NO_2$, wherein said $C_{1-6}$alkyl and $C_{1-6}$alkyloxy are optionally substituted with one or more halogens and wherein $R^4$ has the previously defined meanings.

In another embodiment, Ar is a heteroarylene formed from a heteroaromatic ring selected from thiophene, furan, pyrrole, thiazole, oxazole, imidazole, pyridine, pyrimidine and pyrazine, said heteroarylene being optionally substituted with one or more substituents independently selected from $C_{1-6}$alkyl, $C_{1-6}$alkyloxy and halogen.

In another embodiment Ar is a heteroarylene formed from a bicyclic heteroaromatic ring system selected from benzfuran, benzthiophene, indole, benzoxazole, quinoline and isoquinoline optionally substituted with one or more substituents independently selected from $C_{1-6}$alkyl, $C_{1-6}$alkyloxy and halogen.

In another embodiment, Ar is phenylene or pyridylene, optionally substituted with one or more substituent independently selected from $C_{1-6}$alkyl, $C_{1-6}$alkyloxy and halogen.

In another embodiment Ar is phenylene or pyridylene optionally substituted with methyl, methoxy, fluoro or chloro.

In another embodiment, Ar is selected from the group consisting of:

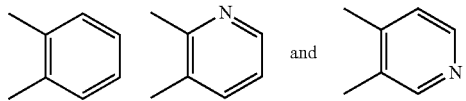

optionally substituted with methyl, fluoro or chloro.

In another embodiment, $R^1$ is $C_{6-10}$aryl optionally substituted with one or more substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O—.

In another embodiment, $R^1$ is $C_{6-10}$aryl optionally substituted with one or more substituent independently selected from methoxy, ethoxy, methyl, amino, halogen and $H_3C$—$(CH_2)_2$—O—.

In another embodiment, $R^1$ is a 4-10 membered saturated or unsaturated heterocyclic ring system comprising one ring or two rings fused together at adjacent ring atoms and comprising a N atom and optionally comprising one or more further heteroatomic moiety independently selected from O, S and $N(R^{1a})_p$, wherein $R^{1a}$ is H or methyl and wherein p is 0 or 1, said heterocyclic ring system being optionally substituted with one or more substituent independently selected from $C_{1-6}$alkyl, $C_{1-6}$alkyloxy, $C_{6-10}$aryl, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O— or two substituents on the same carbon form together with said carbon a carbonyl, wherein said $C_{6-10}$aryl is optionally substituted with 1-2 substituents independently selected from halogen, hydroxyl, $C_{1-6}$alkyl and $C_{1-6}$alkyloxy;

In another embodiment, $R^1$ is:

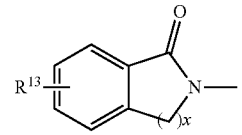

wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O— and x is an integer from 1-3.

In another embodiment, $R^1$ is:

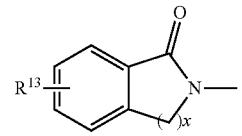

wherein $R^{13}$ is one or more optional substituent independently selected from methoxy, ethoxy, methyl, amino, halogen and $H_3C$—$(CH_2)_2$—O— and x is an integer from 1-2.

In another embodiment, $R^1$ is a fused bicyclic ring system selected from the group consisting of:

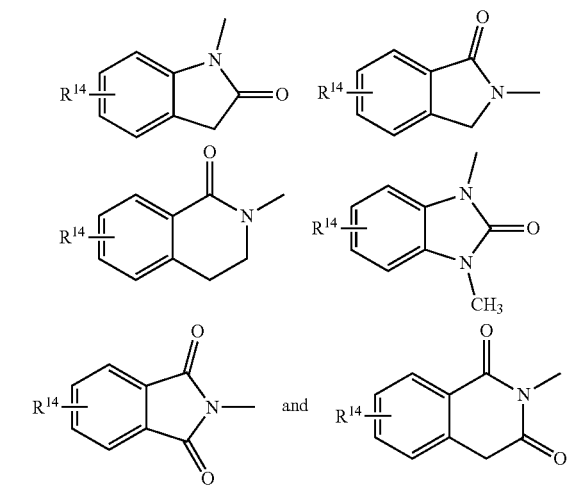

wherein $R^{14}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O—

In a further embodiment, $R^1$ is:

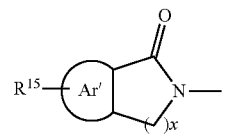

wherein $R^{15}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene- O— and $(C_{1-6}alkyl)_2$-N—$C_{1-2}$alkylene-O—, x is an integer from 1-3 and Ar' is a 5-6 membered heteroaryl ring system comprising 1-3 heteroatoms independently selected from O, S and N and optionally fused to the lactam ring at adjacent carbons.

In a further embodiment, $R^1$ is selected from the group consisting of:

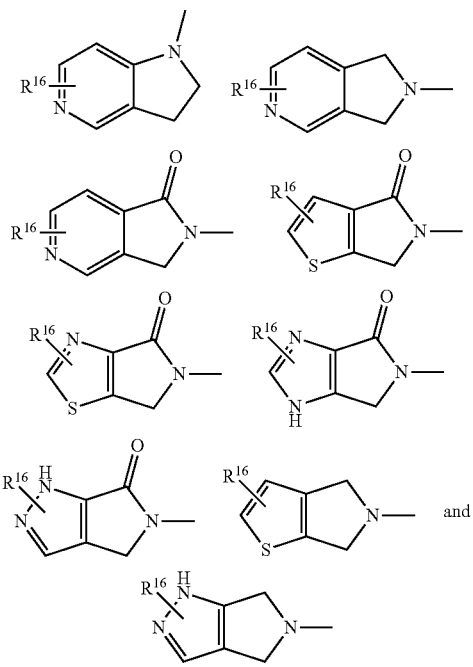

wherein $R^{16}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O—

In another embodiment, $R^1$ is selected from the group consisting of:

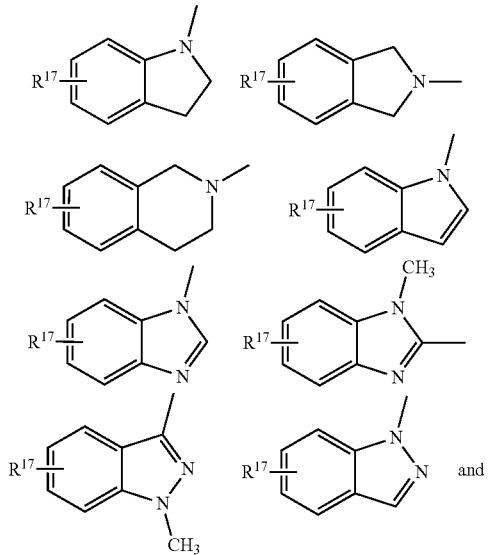

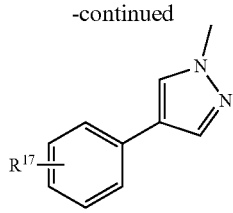

wherein $R^{17}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O—.

In another embodiment, $R^1$ is selected from the group consisting of:

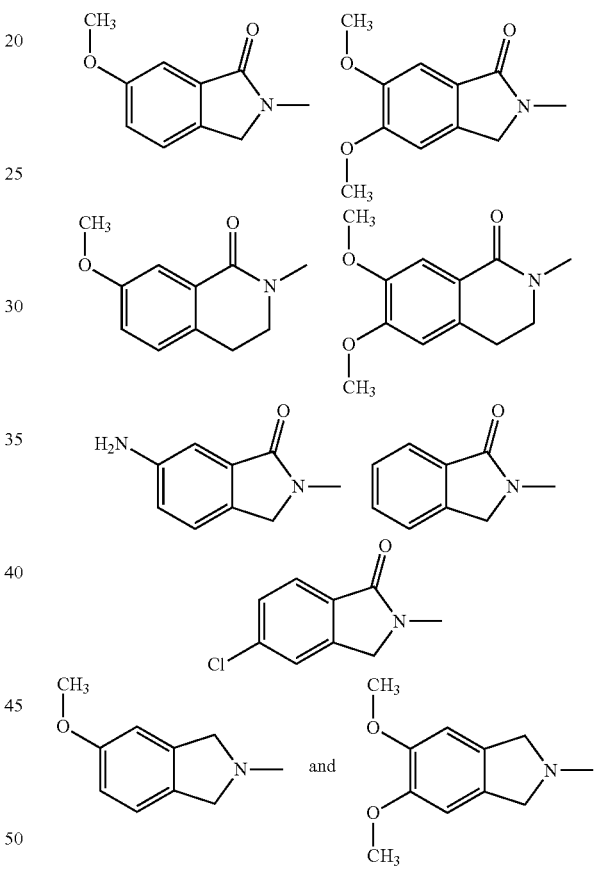

In another embodiment, $R^1$ is selected from the group consisting of:

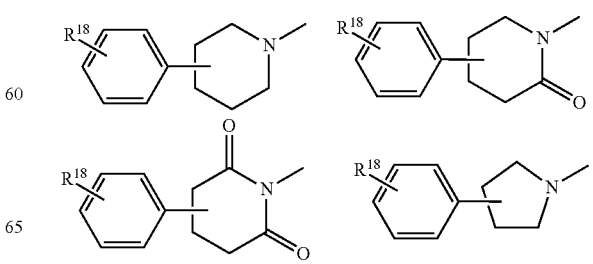

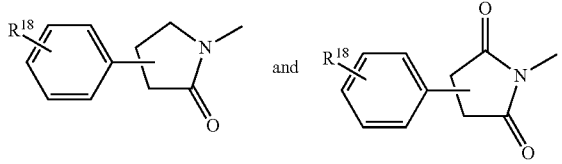

wherein $R^{18}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O—.

In another embodiment, $R^1$ is selected from the group consisting of:

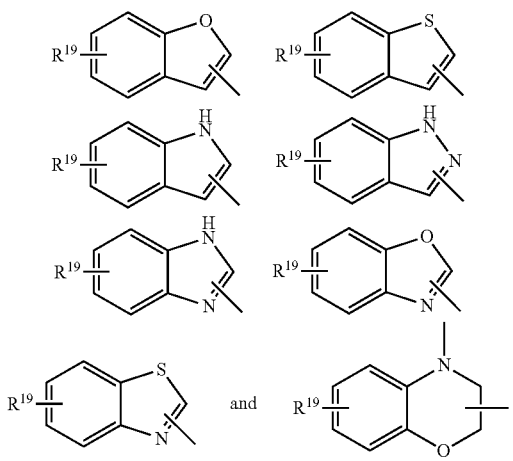

wherein $R^{19}$ is one or more optional substituent independently selected from $C_{1-2}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O—.

In another embodiment of the present invention, $R^2$ is H
In another embodiment, $R^2$ is methyl.
In another embodiment of the present invention, $R^3$ is $C_{6-10}$aryl optionally substituted with 1-2 substituents independently selected from $C_{1-6}$alkyl, $C_{1-6}$alkyloxy and halogen.

In another embodiment, $R^3$ is a 5-10 membered heteroaryl ring system comprising one ring or two rings fused together at adjacent ring atoms and comprising 1-3 heteroatoms independently selected from O, S and N, said heteroaryl ring system being optionally substituted with 1-2 substituents independently selected from $C_{1-6}$alkyl, $C_{1-6}$alkyloxy, amino and halogen.

In another embodiment, $R^3$ is a pyrazole or an imidazole substituted with methyl or amino.

In another embodiment, $R^3$ is a 4-12 membered saturated or unsaturated heterocyclic ring system comprising one ring or two rings fused together at adjacent ring atoms or comprising two rings linked together at the same ring atom thereby forming a spirocyclic ring, said 4-12 membered heterocyclic ring system comprising a N atom and optionally comprising one or more further heteroatomic moiety independently selected from O, S and N$(R^{3a})_n$, wherein $R^{3a}$ is H or $C_{1-6}$alkyl and n is 0 or 1 and wherein said heterocyclic ring system is optionally substituted with 1-2 substituents independently selected from $C_{1-6}$alkyl optionally substituted with hydroxyl, $C_{1-6}$alkyloxy, amino, hydroxyl, halogen, NH$(C_{1-6}$alkyl), N$(C_{1-6}$alkyl$)_2$ or two substituents on the same carbon form together with said carbon a carbonyl.

In another embodiment, $R^3$ is a 4-7 membered monocyclic heterocyclic ring comprising a N atom and optionally comprising one or more further heteroatomic moiety independently selected from O, S and N$(R^{3a})_n$, wherein $R^{3a}$ is H or $C_{1-6}$alkyl and n is 0 or 1, said heterocyclic ring being optionally substituted with 1-2 substituents independently selected from $C_{1-6}$alkyl optionally substituted with hydroxyl, $C_{1-6}$alkyloxy, amino, hydroxyl, NH$(C_{1-6}$alkyl), N$(C_{1-6}$alkyl$)_2$ or two substituents on the same carbon form together with said carbon a carbonyl.

In another embodiment, $R^3$ is a 5-12 membered bicyclic heterocyclic ring system, fused together at two adjacent ring atoms and comprising a N atom and optionally comprising one or more further heteroatomic moiety independently selected from O, S and N$(R^{3a})_n$, wherein $R^{3a}$ is H or $C_{1-6}$alkyl and n is 0 or 1, said heterocyclic ring system being optionally substituted with 1-2 substituents independently selected from $C_{1-6}$alkyl optionally substituted with hydroxyl, $C_{1-6}$alkyloxy, amino, hydroxyl, NH$(C_{1-6}$alkyl), N$(C_{1-6}$alkyl$)_2$ or two substituents on the same carbon form together with said carbon a carbonyl.

In another embodiment, $R^3$ is a 6-12 membered heterocyclic ring system comprising two rings linked together at the same ring atom thereby forming a spirocyclic ring, said heterocyclic ring system comprising a N atom and optionally comprising one or more further heteroatomic moiety independently selected from O, S and N$(R^{3a})_n$, wherein $R^{3a}$ is H or $C_{1-6}$alkyl and n is 0 or 1, said heterocyclic ring system being optionally substituted with 1-2 substituents independently selected from $C_{1-6}$alkyl optionally substituted with hydroxyl, $C_{1-6}$alkyloxy, amino, hydroxyl, NH$(C_{1-6}$alkyl), N$(C_{1-6}$alkyl$)_2$ or two substituents on the same carbon form together with said carbon a carbonyl.

In another embodiment $R^3$ is

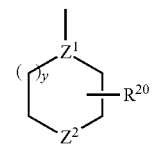

wherein,
$Z^1$ is CH or N and $Z^2$ is CHR$^{20a}$ or NR$^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, NH$(C_{1-6}$alkyl) and N$(C_{1-6}$alkyl$)_2$ and $R^{20a}$ is H or $C_{1-6}$alkyl.

In another embodiment, $R^3$ is piperazine optionally substituted with $C_{1-6}$alkyl optionally substituted with hydroxyl, $C_{1-6}$alkyloxy, amino, hydroxyl, NH$(C_{1-6}$alkyl) or N$(C_{1-6}$alkyl$)_2$.

In another embodiment, $R^3$ is

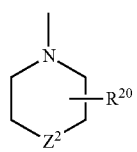

wherein,

Z² is CH₂ or NH and R²⁰ is 1-2 optional substituents independently selected from methyl, hydroxymethyl, methoxy, amino, hydroxyl, methylamino and dimethylamino.

In another embodiment, R³ is piperazine.

In another embodiment, R³ is selected from the group consisting of:

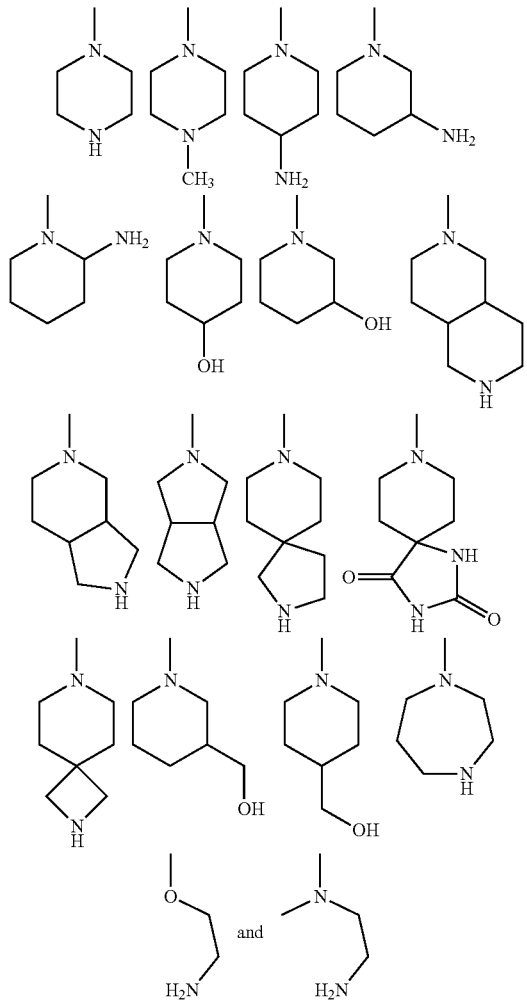

In another embodiment of the present invention X⁴ is C, i.e., the moiety

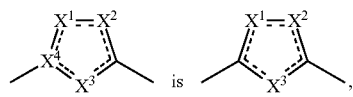

wherein X1, X2 and X3 have the previously defined meanings.

In another embodiment of the present invention, the moiety

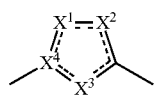

is an azolylene, i.e., at least one of X1, X2 and X3 is N(R¹¹)$_v$, X⁴ is C and any remaining X1, X2 and X3 are independently selected from O, S and CR¹¹ with the proviso that at least two of X1, X2 and X3 are not C and that no more than one of X1, X2 and X3 is O or S and when one of X1, X2 and X3 is N, X1, X2 and X3 cannot be S, wherein R¹¹ and v have the previously defined meanings or X4 is N and X1, X2 and X3 are independently selected from O, S, N(R¹¹)$_v$ and CR¹¹ with the proviso that at least two of X1, X2 and X3 are not C and that no more than one of X1, X2 and X3 is O or S and when one of X1, X2 and X3 is N, X1, X2 and X3 cannot be S, wherein R¹¹ and v have the previously defined meanings In another embodiment, the moiety

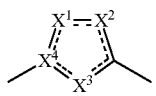

is an oxazolylene, i.e., one of X1, X2 and X3 is N(R¹¹)$_v$, one of X1, X2 and X3 is O one of X1, X2 and X3 is CR¹¹ and X⁴ is C, wherein R¹¹ and v have the previously defined meanings and wherein each R¹¹ is selected independently.

In another embodiment, two of X1, X2 and X3 are N(R¹¹)$_v$, one of X1, X2 and X3 is O, and X⁴ is C, wherein R¹¹ and v have the previously defined meanings.

In another embodiment, the moiety

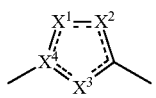

is an oxadiazylene, i.e., two of X1, X2 and X3 are N(R¹¹)$_v$, one of X1, X2 and X3 is O and X⁴ is C, wherein R¹¹ and v have the previously defined meanings and wherein each R¹¹ is selected independently.

In another embodiment, the moiety

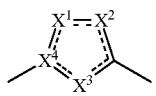

is a thiadiazylene, i.e., two of X1, X2 and X3 are N(R¹¹)$_v$, one of X1, X2 and X3 is S and X⁴ is C, wherein R¹¹ and v have the previously defined meanings and wherein each R¹¹ is selected independently.

In another embodiment, the moiety

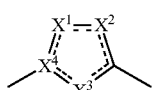

is a triazylene, i.e., all of X1, X2 and X3 are N(R¹¹)$_v$ and X⁴ is C or two of X1, X2 and X3 are N(R¹¹)$_v$, and the other X1, X2 and X3 is CR¹¹ and X⁴ is N, wherein R¹¹ and v have the previously defined meanings and wherein each R¹¹ is selected independently.

In another embodiment, the moiety

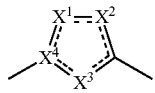

is an imidazolylene, i.e., $X^1$ and $X^3$ are $N(R^{11})_v$ or $X^2$ and $X^3$ are $N(R^{11})_v$, the other X1, X2 and X3 is $CR^{11}$ and $X^4$ is C or $X^2$ is $N(R^{11})_v$, $X^1$ and $X^3$ are $CR^{11}$ and $X^4$ is N wherein $R^{11}$ and v have the previously defined meanings and wherein each $R^{11}$ is selected independently.

In another embodiment, the moiety

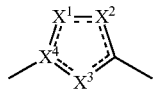

is a pyrazolylene, i.e., $X^1$ and $X^2$ are $N(R^{11})_v$, X3 is $CR^{11}$ and $X^4$ is C or one of $X^1$ and $X^3$ is $N(R^{11})_v$, the other two $X^1$, $X^2$ and $X^3$ are $CR^{11}$ and $X^4$ is N, wherein $R^{11}$ and v have the previously defined meanings and wherein each $R^{11}$ is selected independently.

In another embodiment, the moiety

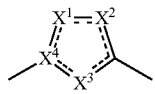

is a furanylene, i.e., $X^1$ and $X^2$ are $CR^{11}$, $X^3$ is O and $X^4$ is C, wherein $R^{11}$ has the previously defined meanings and wherein each $R^{11}$ is selected independently.

In another embodiment, the moiety

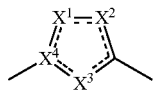

is a thienylene, i.e., $X^1$ and $X^2$ are $CR^{11}$, $X^3$ is S and $X^4$ is C, wherein $R^{11}$ has the previously defined meanings and wherein each $R^{11}$ is selected independently.

In another embodiment the moiety

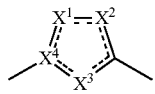

is selected from the group consisting of:

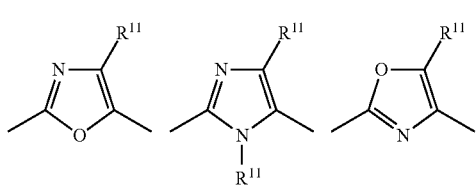

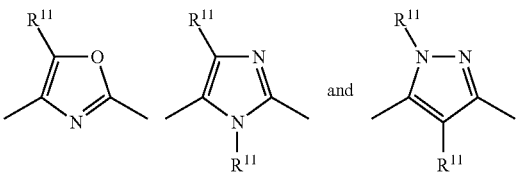

wherein $R^{11}$ has the previously defined meanings and each $R^{11}$ is selected independently.

In another embodiment, the moiety

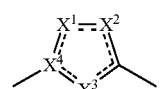

is selected from the group consisting of:

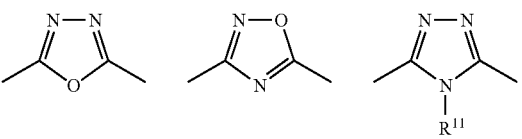

wherein $R^{11}$ has the previously defined meanings.

In another embodiment, the moiety

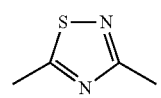

is selected from the group consisting of:

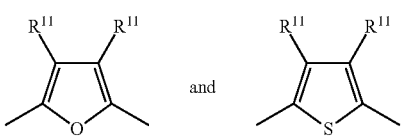

in another embodiment of the present invention, the moiety

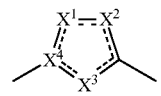

is selected from the group consisting of:

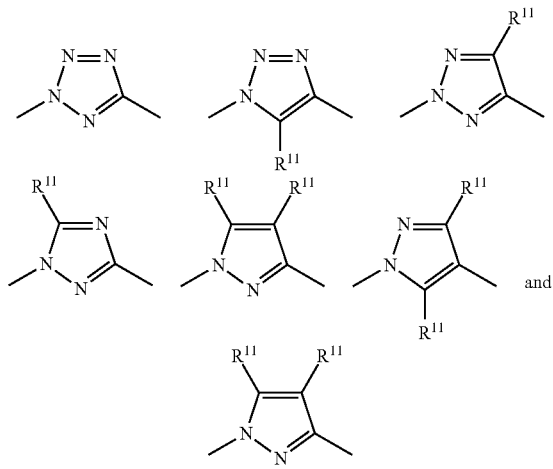

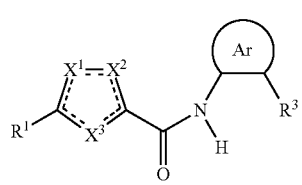

wherein $R^{11}$ has the previously defined meanings.

In another embodiment of the present invention, $R^{11}$ is H, $C_{1-6}$alkyl or halogen.

In another embodiment, $R^{11}$ is H, methyl or chloro.

In another embodiment of the present invention, Y is O.

in another embodiment, Y is S.

In another embodiment, Y is $NR^{12}$, wherein $R^{12}$ has the previously defined meanings.

In another embodiment, Y is NRH

In another embodiment, Y is $NRCH_3$.

In another embodiment of the present invention is a heterocyclic amide derivative of formula (II)

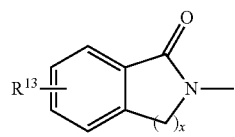

Formula (II)

wherein,

Ar is phenylene or pyridylene, being joined to NH and $R^3$ via any two adjacent ring carbons, said phenylene or pyridylene being optionally substituted with one or more substituent independently selected from $C_{1-6}$alkyl, $C_{1-6}$alkyloxy and halogen.

$R^1$ is

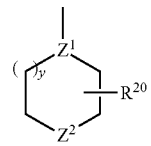

wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O— and x is an integer from 1-3.

$R^3$ is

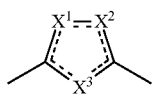

wherein, $Z^1$ is CH or N and $Z^2$ is $CHR^{20a}$ or $NR^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}$alkyl$)$ and $N(C_{1-6}$alkyl$)_2$ and $R^{20a}$ is H or $C_{1-6}$alkyl and the moiety is azolylene, i.e., at least one of X1, X2 and X3 is $N(R^{11})_v$ and the others are independently $CR^{11}$, O or S, wherein $R^{11}$ is H, $C_{1-6}$alkyl or halogen and v is 0 or 1, with the proviso that at least two of X1, X2 and X3 are not C and that no more than one of X1, X2 and X3 is O or S and when one of X1, X2 and X3 is N, X1, X2 and X3 cannot be S or a pharmaceutically acceptable salt, solvate, ester or prodrug thereof.

In another embodiment of the present invention is a heterocyclic amide derivative of formula (III)

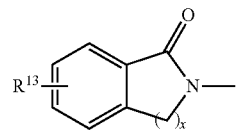

Formula (III)

wherein,

Ar is phenylene or pyridylene, being joined to NH and $R^3$ via any two adjacent ring carbons on said phenylene or pyridylene, said phenylene or pyridylene being optionally substituted with one or more substituent independently selected from $C_{1-6}$alkyl, $C_{1-6}$alkyloxy and halogen;

$R^1$ is wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O— and x is an integer from 1-3;

$R^3$ is

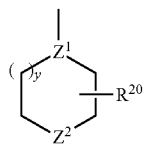

wherein, $Z^1$ is CH or N and $Z^2$ is $CHR^{20a}$ or $NR^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}alkyl)$ and $N(C_{1-6}alkyl)_2$ and $R^{20a}$ is H or $C_{1-6}$alkyl and the moiety

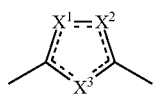

is azolylene, wherein at least two of X1, X2 and X3 are $N(R^{11})_v$ and the other is $CR^{11}$, O or S, wherein $R^{11}$ is H, $C_{1-6}$alkyl or halogen and v is 0 or 1, or a pharmaceutically acceptable salt, solvate, ester or prodrug thereof.

In another embodiment of the present invention is a heterocyclic amide derivative of formula (IV)

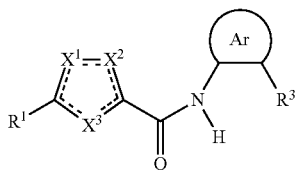

Formula (IV)

wherein,

Ar is phenylene or pyridylene being joined to NH and $R^3$ via any two adjacent ring carbons, said phenylene or pyridylene being optionally substituted with one or more substituents independently selected from $C_{1-6}$alkyl, $C_{1-6}$alkyloxy and halogen.

$R^1$ is

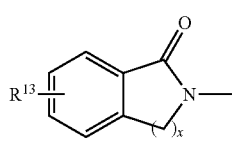

wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}alkyl)_2$-N—$C_{1-2}$alkylene-O— and x is an integer from 1-3.

$R^3$ is

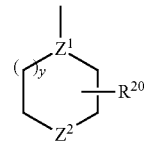

wherein, $Z^1$ is CH or N and $Z^2$ is $CHR^{20a}$ or $NR^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}alkyl)$ and $N(C_{1-6}alkyl)_2$ and $R^{18a}$ is H or $C_{1-6}$alkyl and the moiety

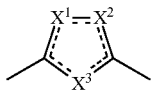

is selected from the group consisting of

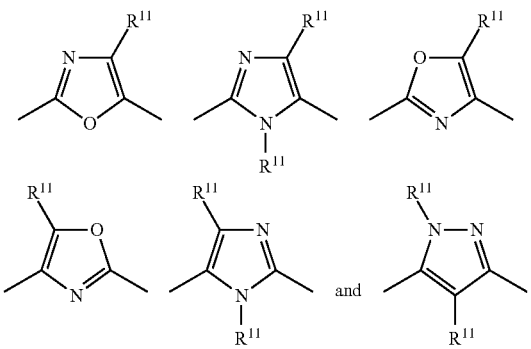

and wherein $R^{11}$ is H, $C_{1-6}$alkyl or halogen, or a pharmaceutically acceptable salt, solvate, ester or prodrug thereof.

In another embodiment of the present invention is a heterocyclic amide derivative of formula (V)

Formula (V)

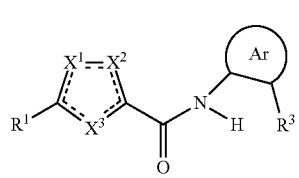

wherein,

Ar is phenylene or pyridylene, being joined to NH and $R^3$ via any two adjacent ring carbons, said phenylene or pyridylene being optionally substituted with one or more substituents independently selected from $C_{1-6}$alkyl, $C_{1-6}$alkyloxy and halogen.

$R^1$ is

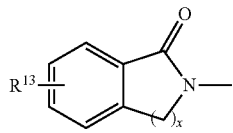

wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O— and x is an integer from 1-3.

$R^3$ is

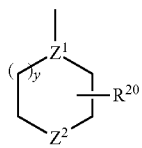

wherein,
$Z^1$ is CH or N and $Z^2$ is $CHR^{20a}$ or $NR^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}$alkyl$)$ and $N(C_{1-6}$alkyl$)_2$ and $R^{20a}$ is H or $C_{1-6}$alkyl and the moiety

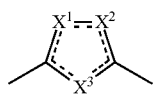

is selected from the group consisting of:

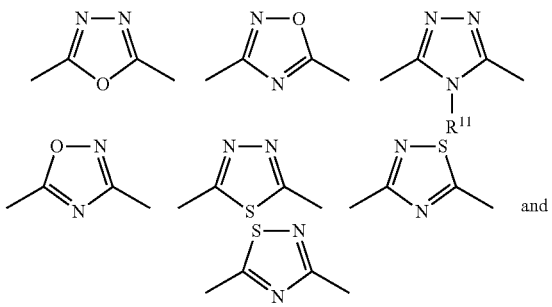

wherein $R^{11}$ is H, $C_{1-6}$alkyl or halogen,
or a pharmaceutically acceptable salt, solvate, ester or prodrug thereof.

In another embodiment of the present invention is a heterocyclic amide derivative of formula (VI)

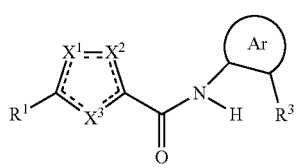

Formula (VI)

wherein,
Ar is pyridylene, being joined to NH and $R^3$ via any two adjacent ring carbons, said pyridylene being optionally substituted with one or more substituents independently selected from $C_{1-6}$alkyl, $C_{1-6}$ alkyloxy and halogen.

$R^1$ is

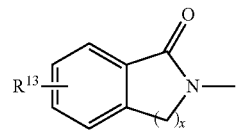

wherein $R^{13}$ is one or more optional substituent independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O— and $(C_{1-6}$alkyl$)_2$-N—$C_{1-2}$alkylene-O— and x is an integer from 1-3.

$R^3$ is

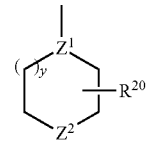

wherein,
$Z^1$ is CH or N and $Z^2$ is $CHR^{20a}$ or $NR^{20a}$; y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}$alkyl$)$ and $N(C_{1-6}$alkyl$)_2$ and $R^{20a}$ is H or $C_{1-6}$alkyl and the moiety

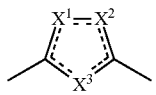

is selected from

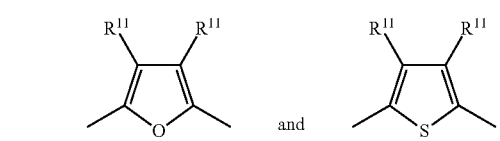

wherein $R^{11}$ is H, $C_{1-6}$alkyl or halogen,
or a pharmaceutically acceptable salt, solvate, ester or prodrug thereof.

In another embodiment of the present invention is a heterocyclic amide derivative of formula (VII)

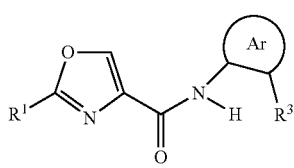

Formula (VII)

wherein,

Ar is pyridylene, being joined to NH and $R^3$ via any two adjacent ring carbons and being optionally substituted with one or more substituents independently selected from methyl, methoxy, chloro and fluoro.

$R^1$ is

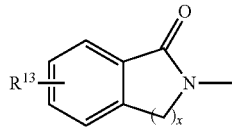

wherein $R^{13}$ is one or more optional substituent independently selected from methoxy, ethoxy, methyl, amino, halogen and $H_3C$—$(CH_2)_2$—O— and x is an integer from 1-2 and $R^3$ is

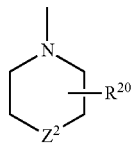

wherein,

Z is $CH_2$ or NH and $R^{20}$ is 1-2 optional substituents independently selected from methyl, hydroxymethyl, methoxy, amino, hydroxyl, methylamino and dimethylamino or a pharmaceutically acceptable salt, solvate, ester or prodrug thereof.

In another embodiment of the present invention is a heterocyclic amide derivative of formula (VIII)

Formula (VIII)

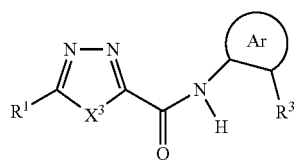

wherein,

Ar is pyridylene, being joined to NH and $R^3$ via any two adjacent ring carbons and being optionally substituted with one or more substituents independently selected from methyl, methoxy, chloro and fluoro.

$R^1$ is

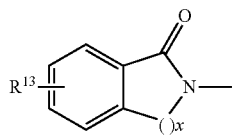

wherein $R^{13}$ is one or more optional substituent independently selected from methoxy, ethoxy, methyl, amino, halogen and $H_3C$—$(CH_2)_2$—O— and x is an integer from 1-2;

$R^3$ is

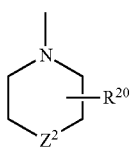

wherein,

Z is $CH_2$ or NH and $R^{20}$ is 1-2 optional substituents independently selected from methyl, hydroxymethyl, methoxy, amino, hydroxyl, methylamino and dimethylamino and $X^3$ is O, S or NH or a pharmaceutically acceptable salt, solvate, ester or prodrug thereof.

In another embodiment of the present invention is a heterocyclic amide derivative of formula (IX)

Formula (IX)

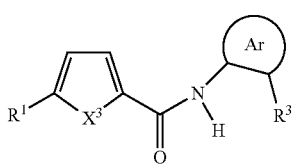

wherein,

Ar is pyridylene, being joined to NH and $R^3$ via any two adjacent ring carbons and being optionally substituted with one or more substituents independently selected from methyl, methoxy, chloro and fluoro.

$R^1$ is

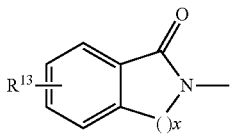

wherein $R^{13}$ is one or more optional substituent independently selected from methoxy, ethoxy, methyl, amino, halogen and $H_3C$—$(CH_2)_2$—O— and x is an integer from 1-2;

$R^3$ is

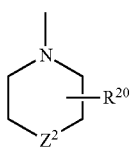

wherein,

Z is $CH_2$ or NH and $R^{20}$ is 1-2 optional substituents independently selected from methyl, hydroxymethyl, methoxy, amino, hydroxyl, methylamino and dimethylamino and $X^3$ is O or S or a pharmaceutically acceptable salt, solvate, ester or prodrug thereof.

In another embodiment of the present invention is a heterocyclic amide derivative selected from the group consisting of:

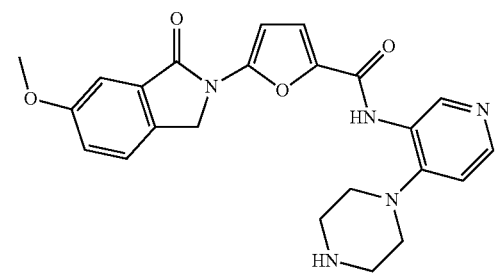
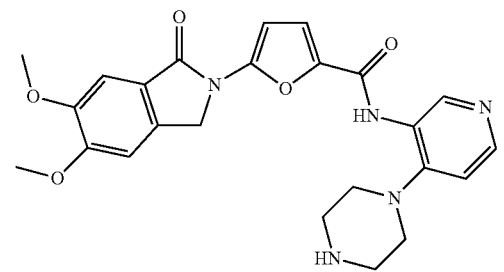
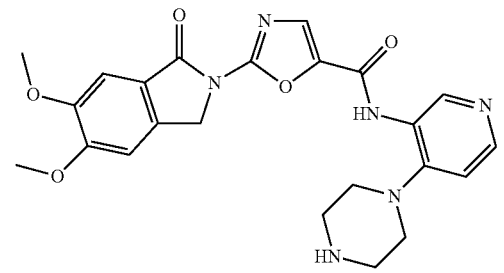
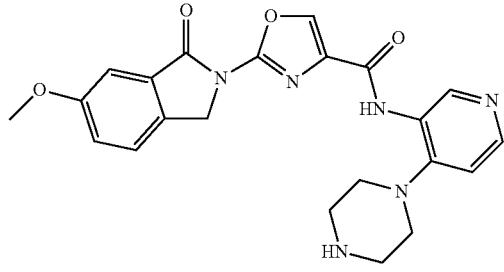
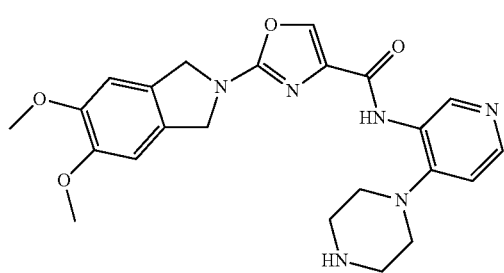
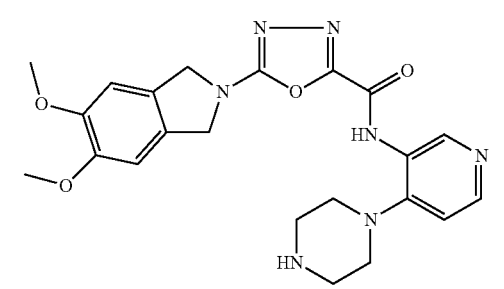
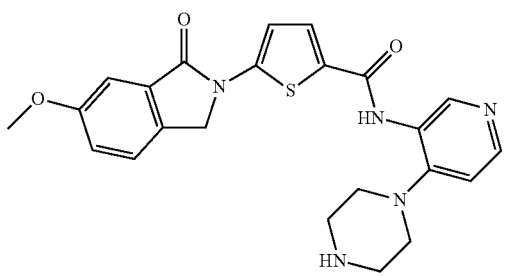
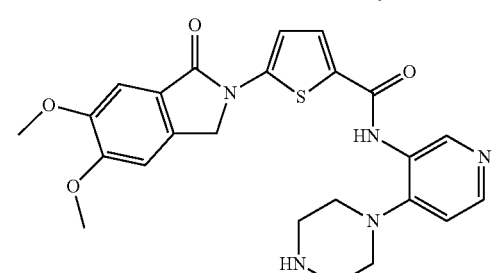
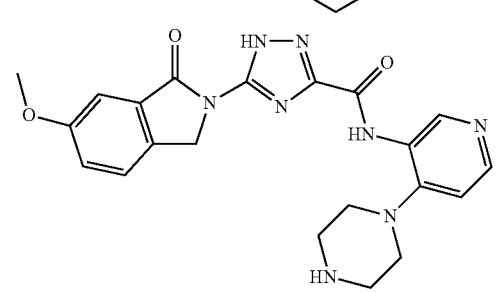
or a pharmaceutically acceptable salt, solvate, ester or prodrug thereof.
In another embodiment of the present invention is a heterocyclic amide derivative selected from the group consisting of:
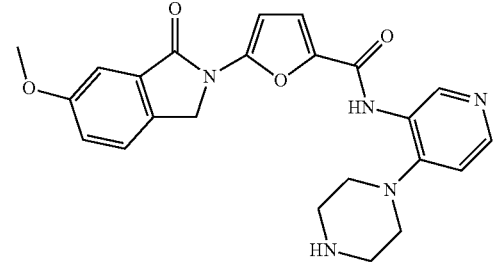
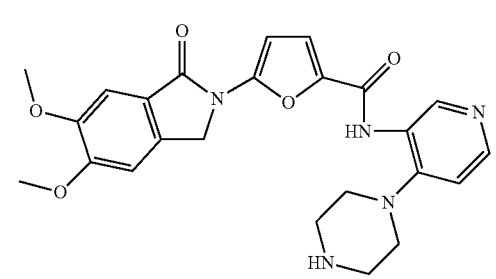

47
-continued
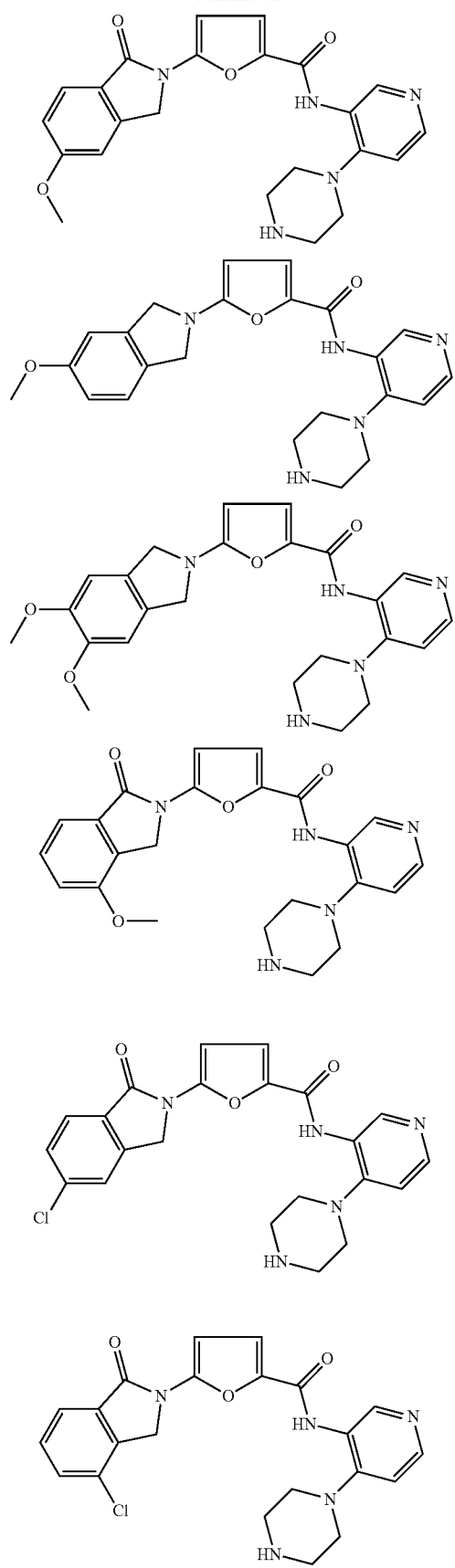
48
-continued
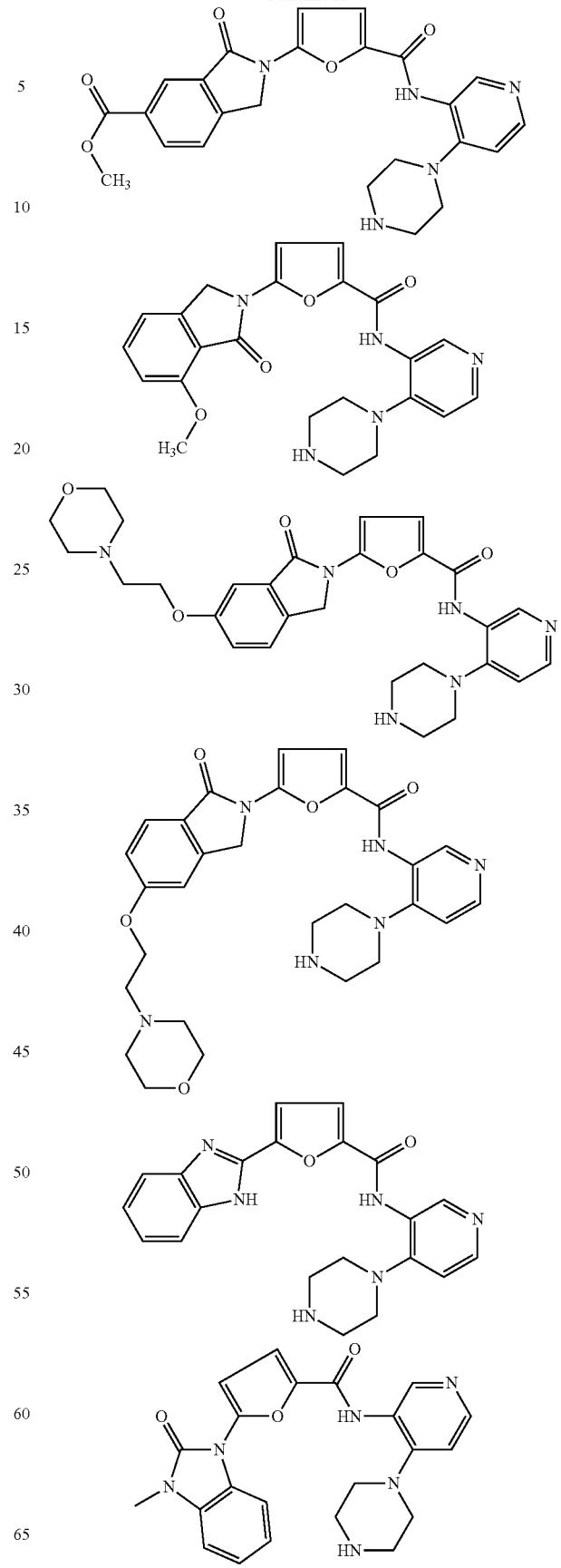

49
-continued
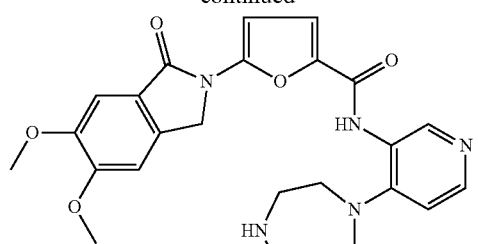
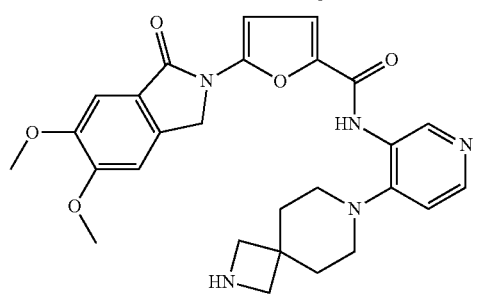
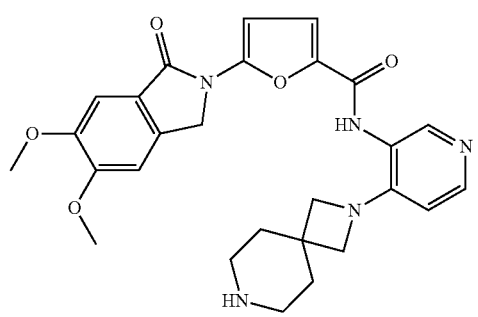
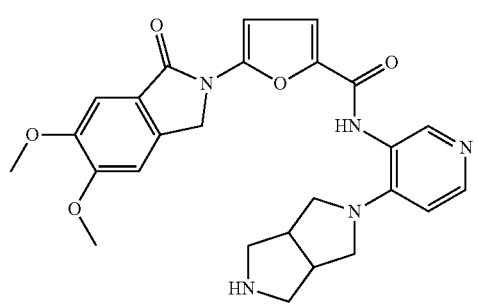
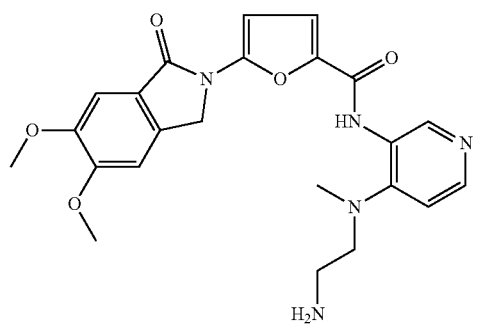
50
-continued
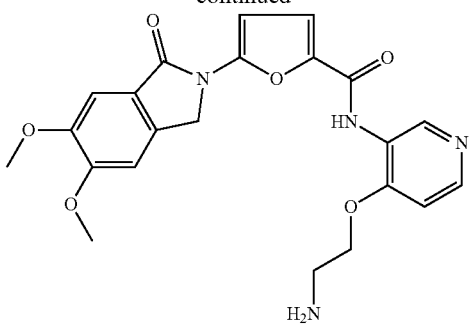
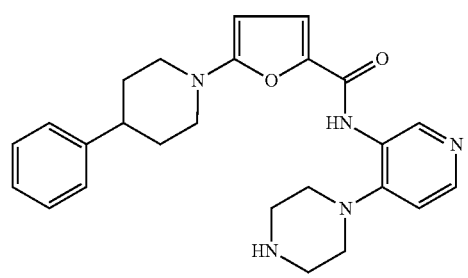
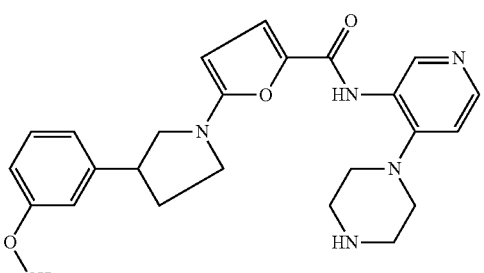
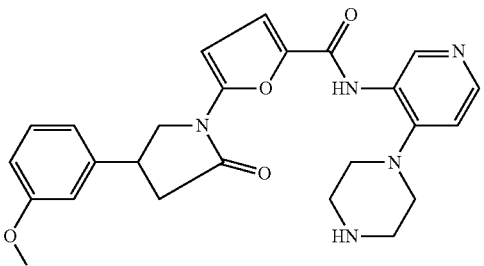
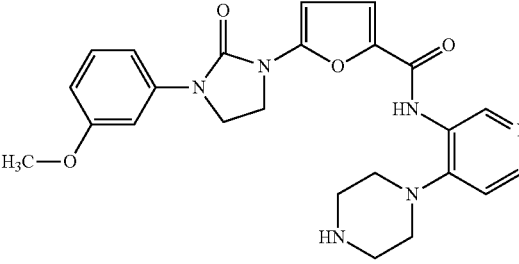
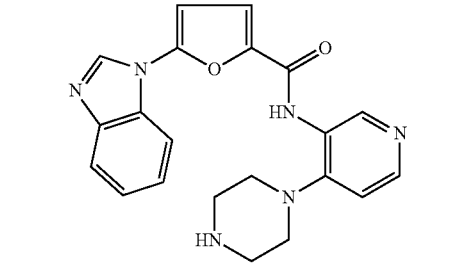

51
-continued
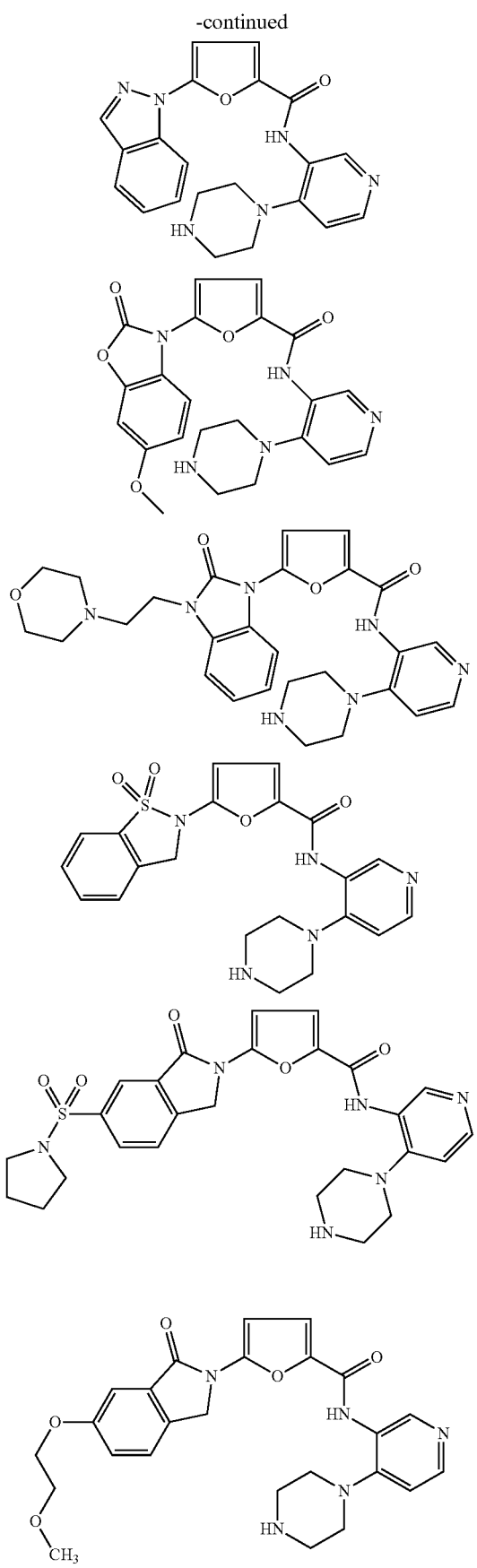
52
-continued
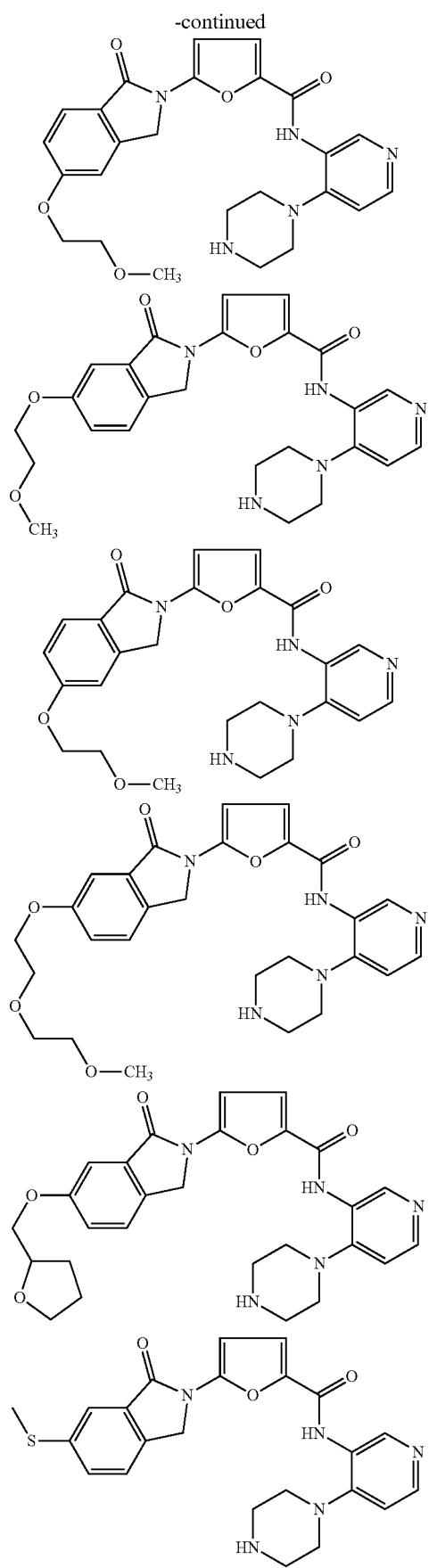

-continued
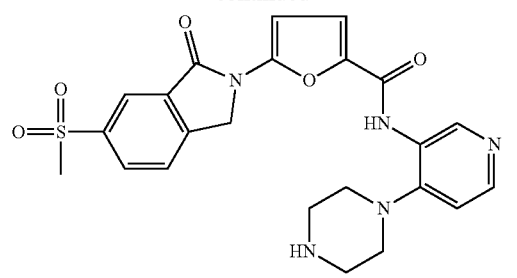
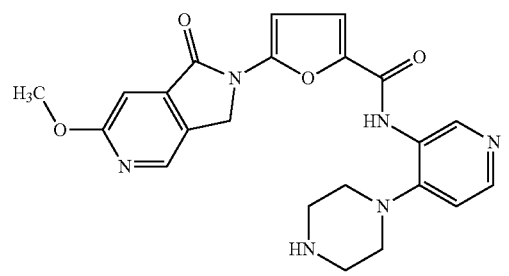
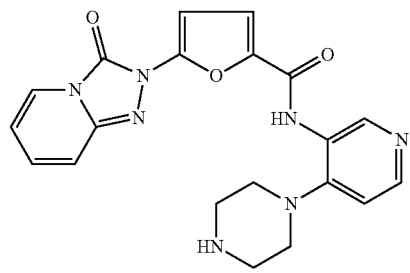
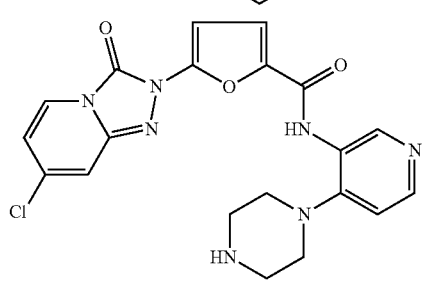
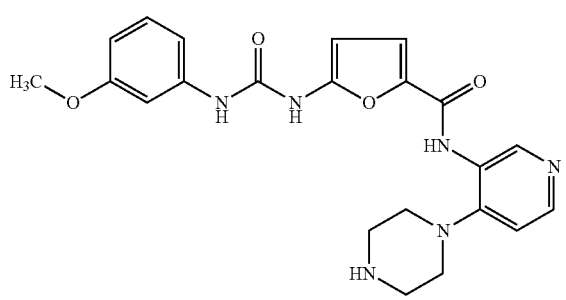
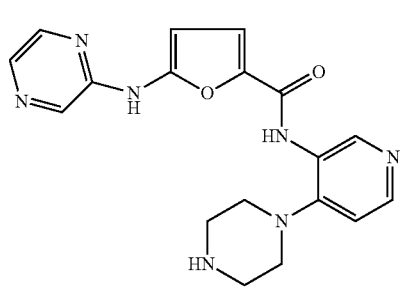
-continued
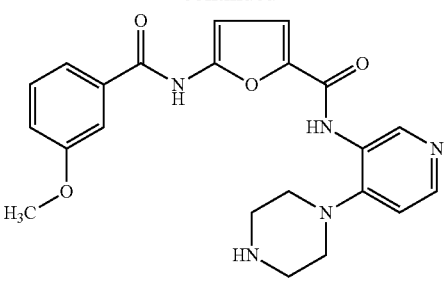
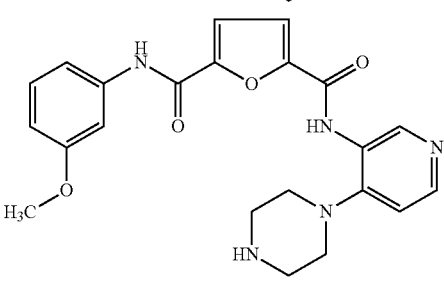
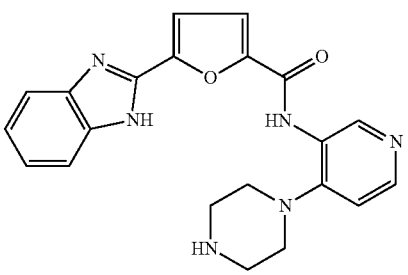
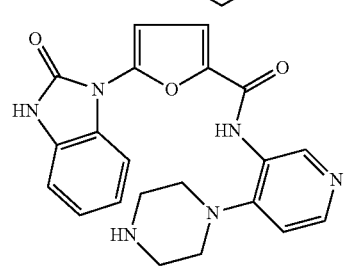
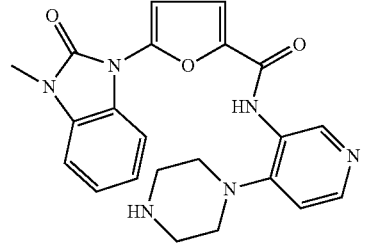
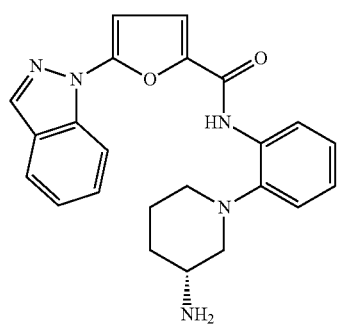

55
-continued
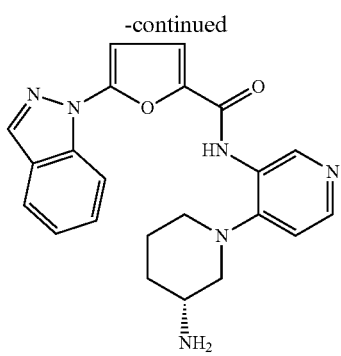
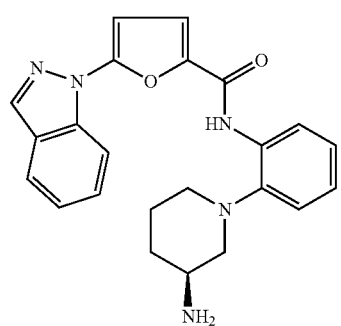
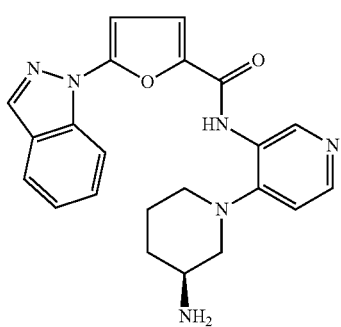
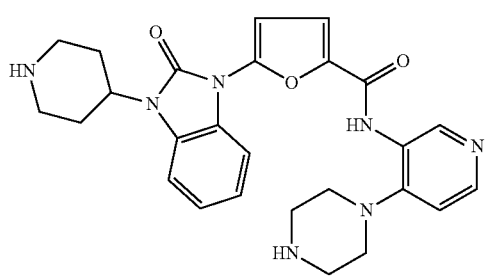
56
-continued
or a pharmaceutically acceptable salt, solvate, ester or prodrug thereof.
In another embodiment of the present invention is a heterocyclic amide derivative selected from the group consisting of:

-continued
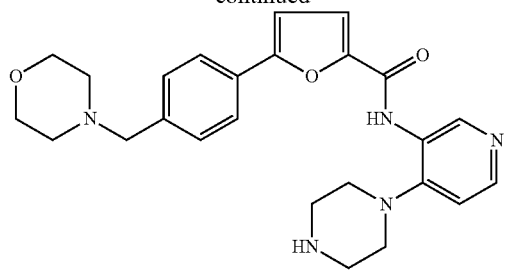
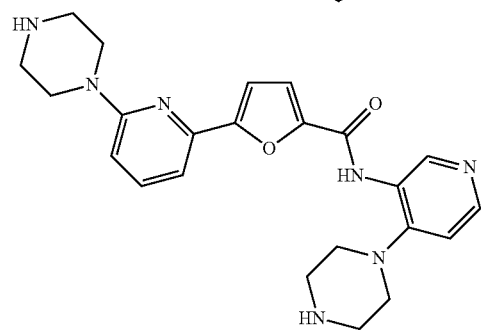
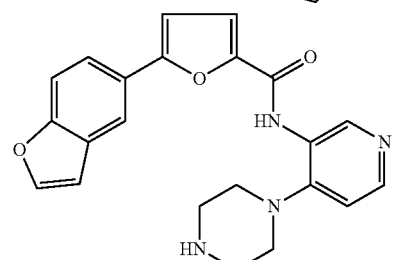
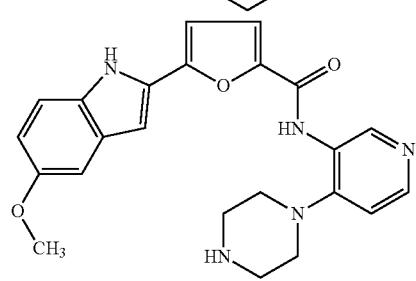
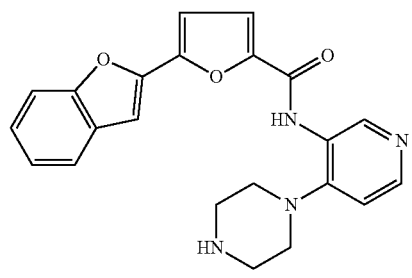
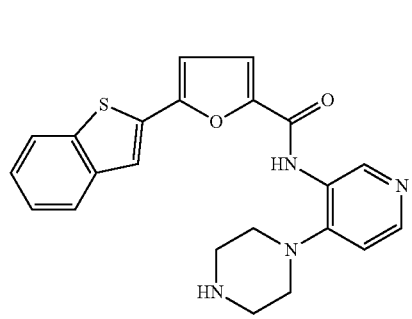
-continued
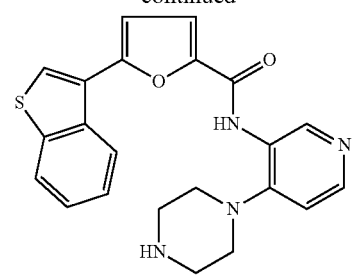
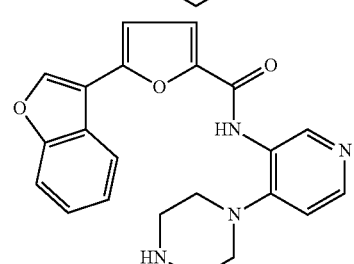
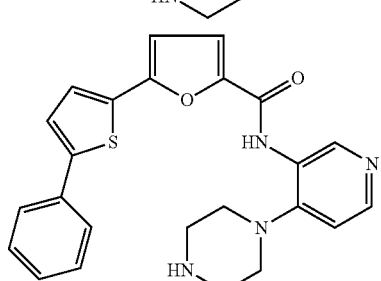
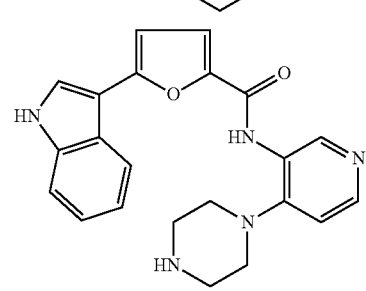
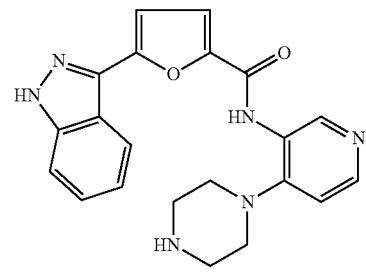
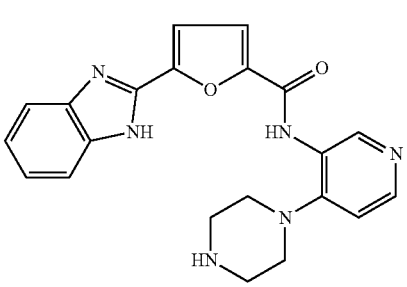

-continued
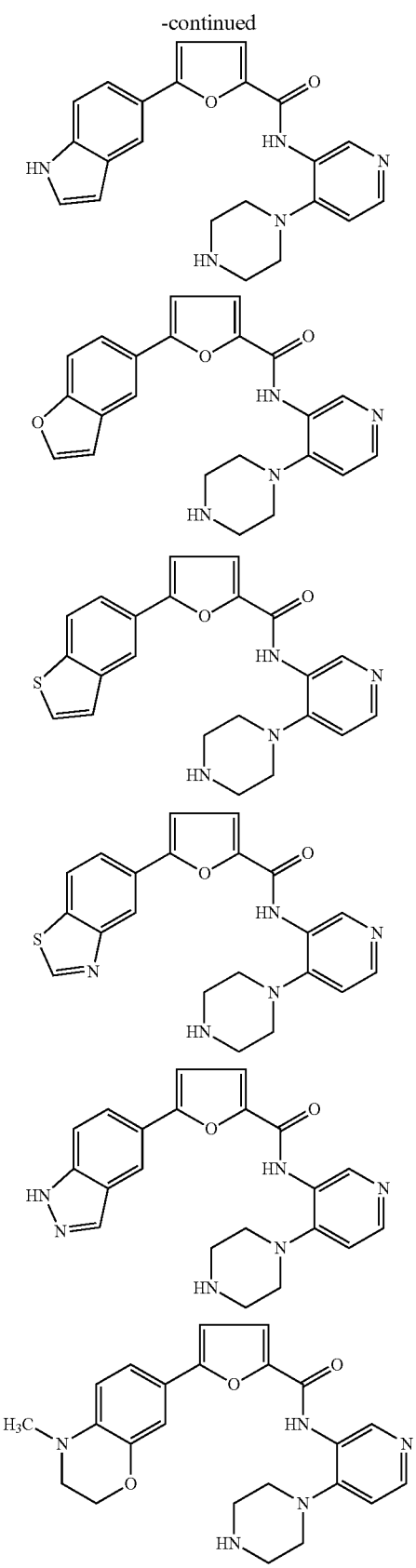
or a pharmaceutically acceptable salt, solvate, ester or prodrug thereof.
In another embodiment of the present invention is a heterocyclic amide derivative selected from the group consisting of:
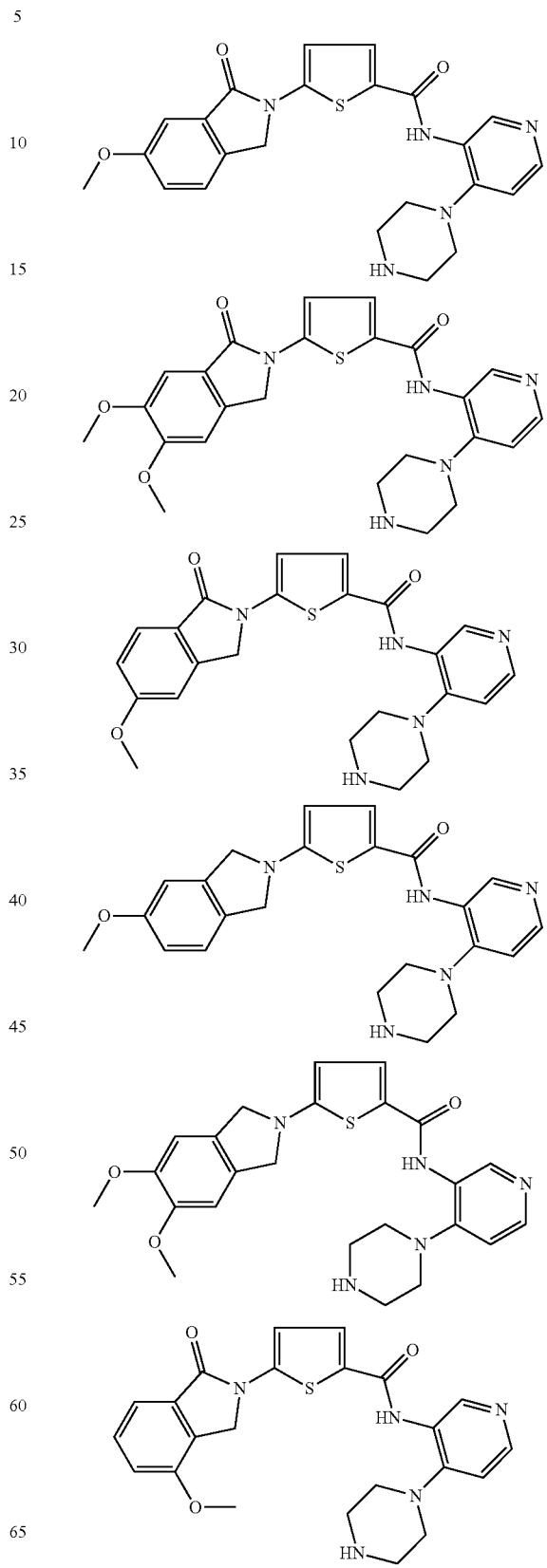

61
-continued
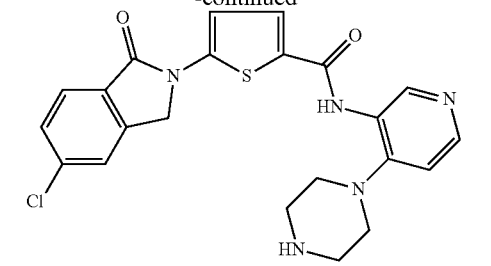
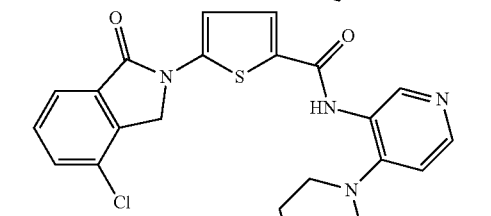
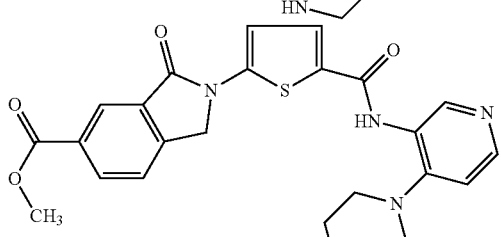
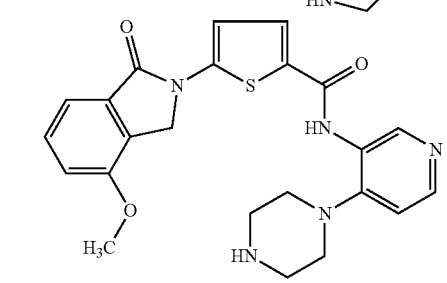
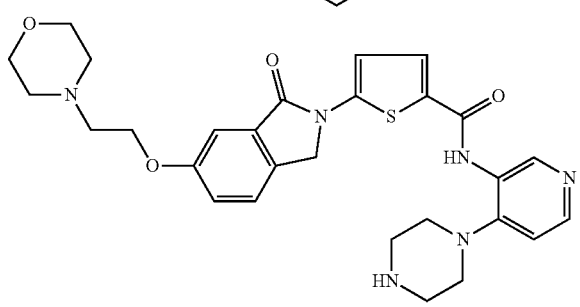
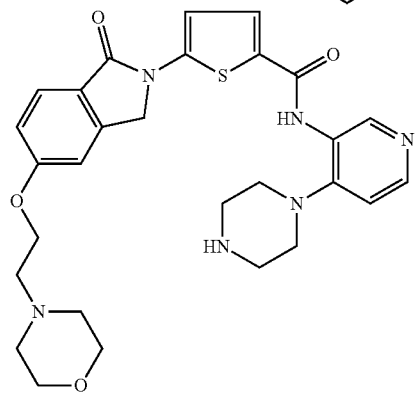
62
-continued
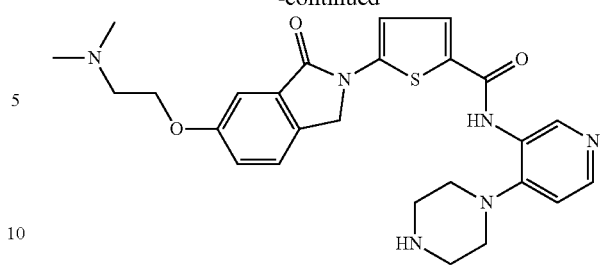
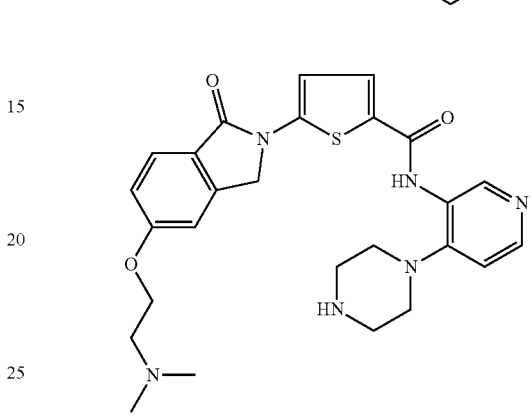
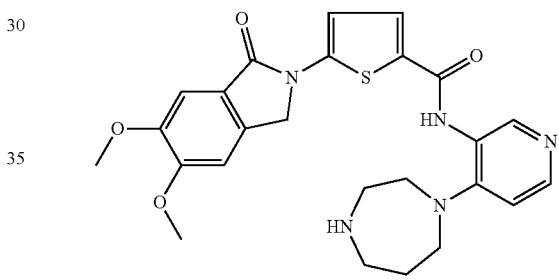
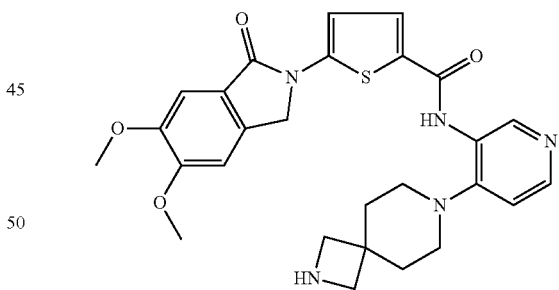
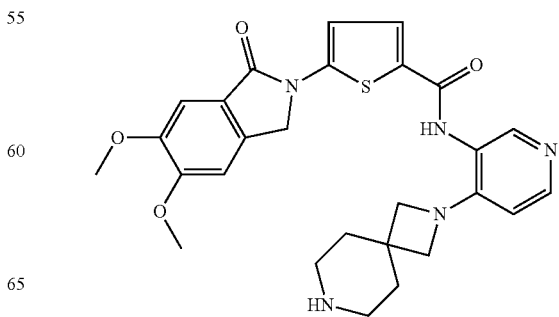

-continued
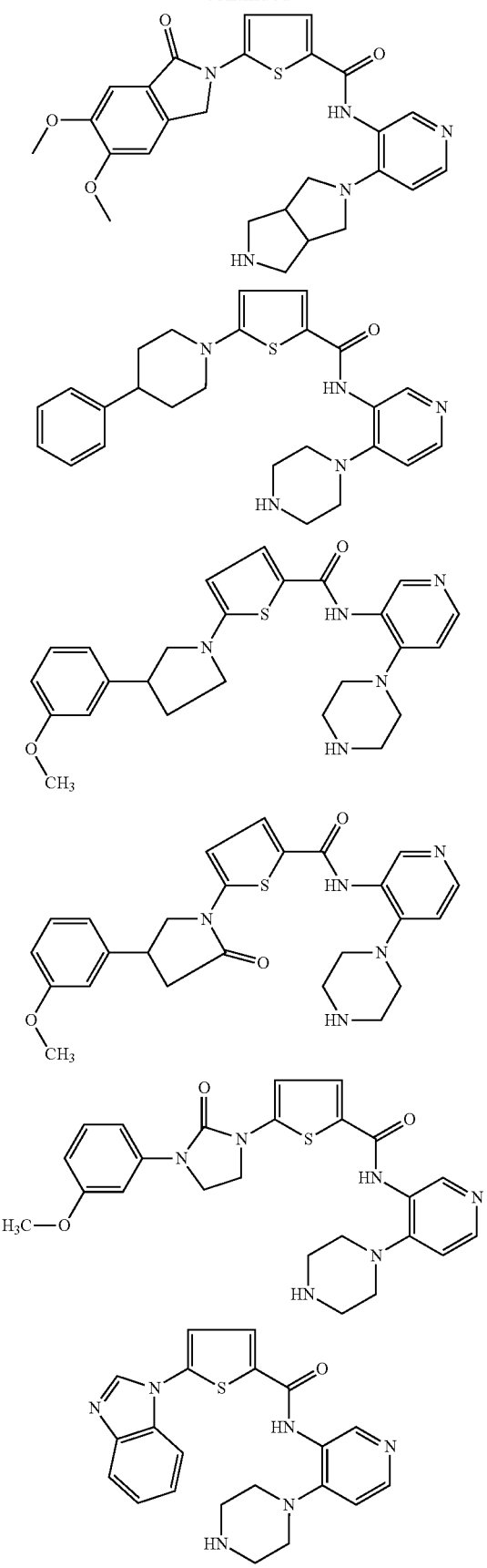
-continued
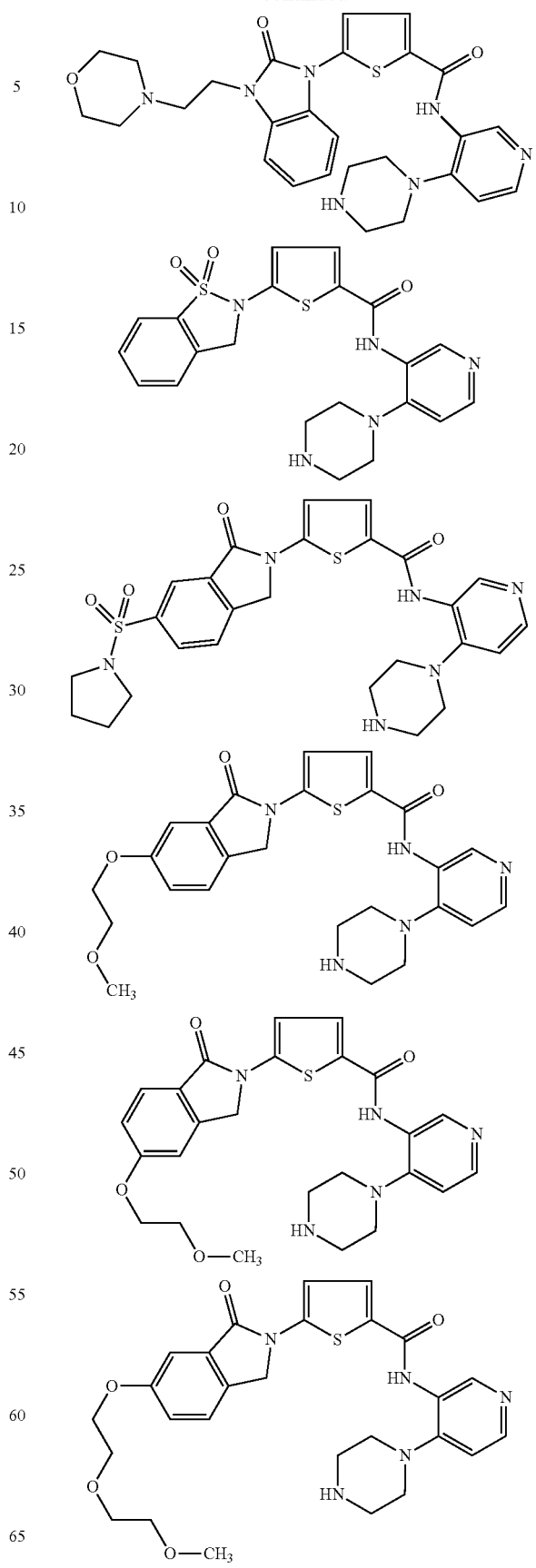

65
-continued
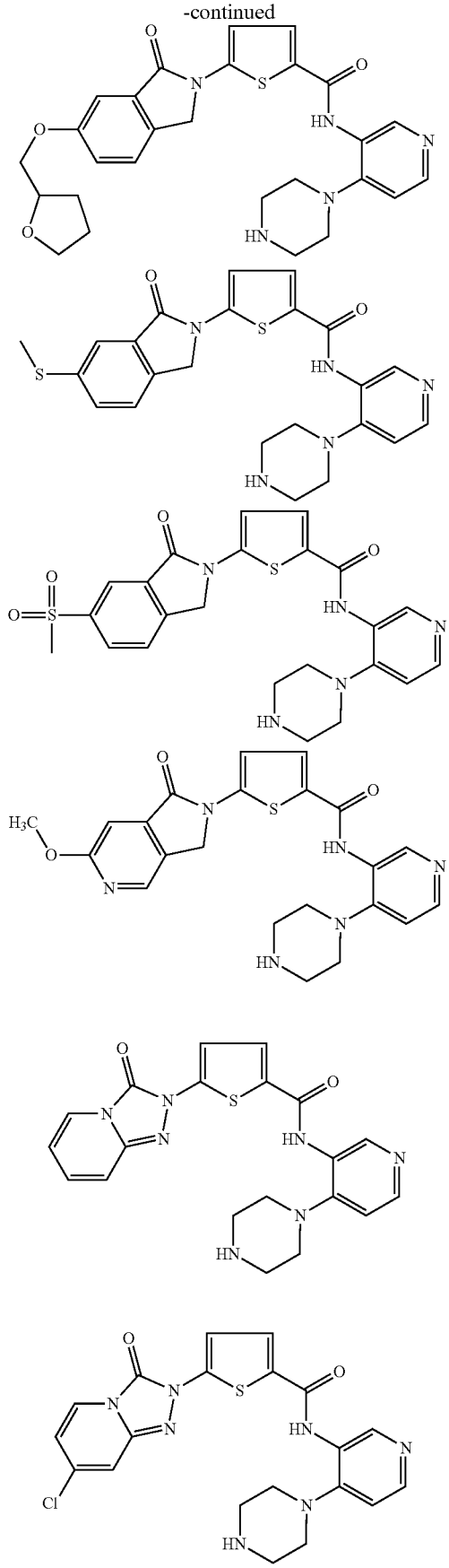
66
-continued
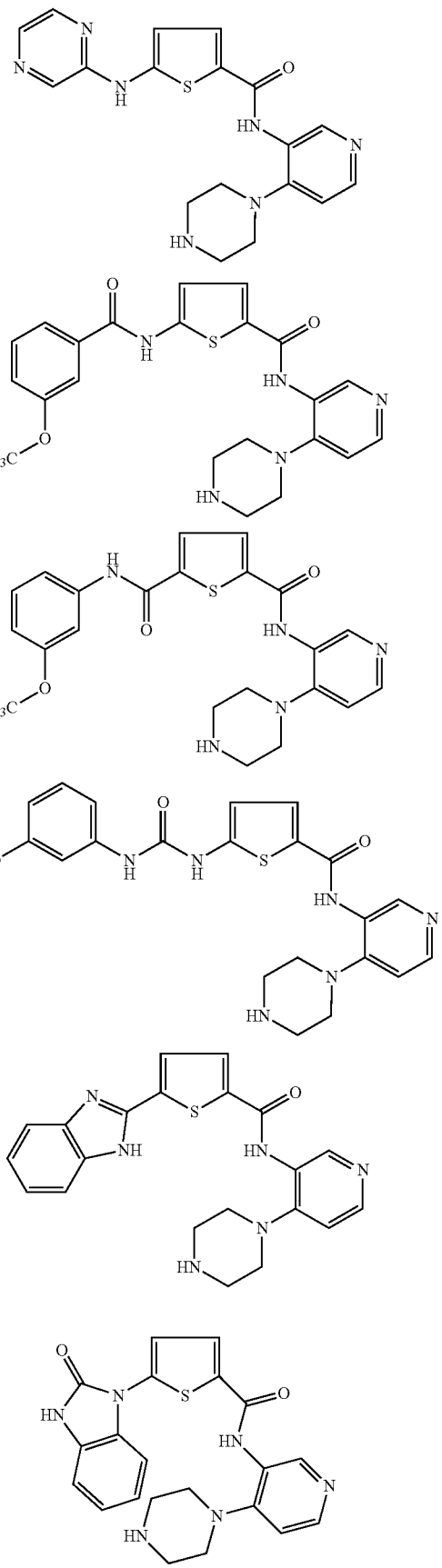

67
-continued
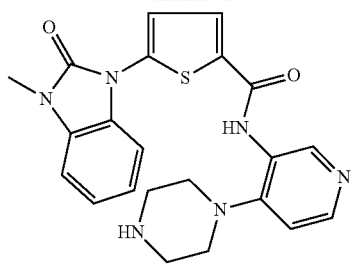
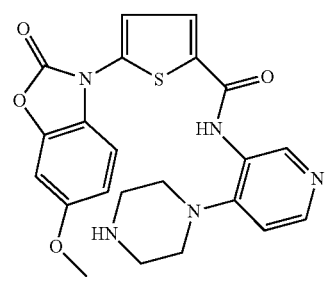
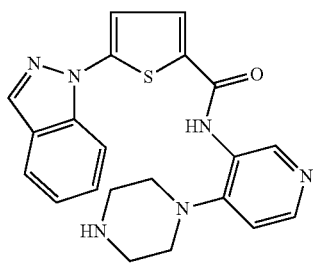
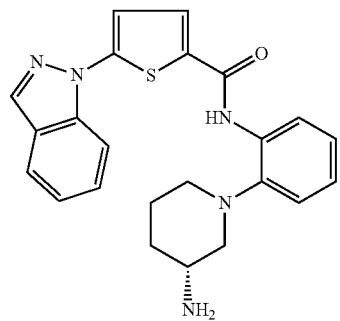
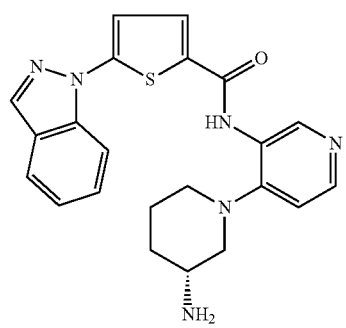
68
-continued
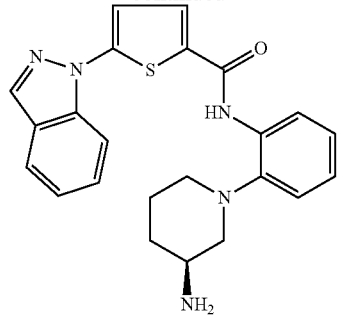
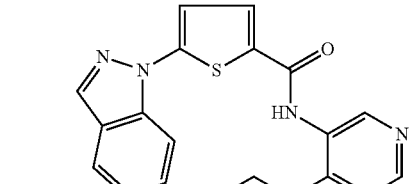
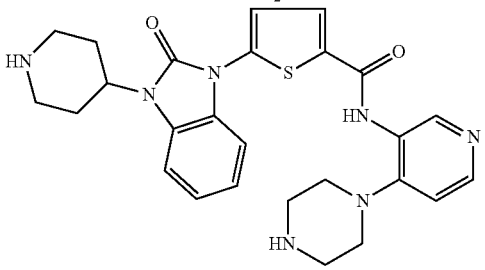
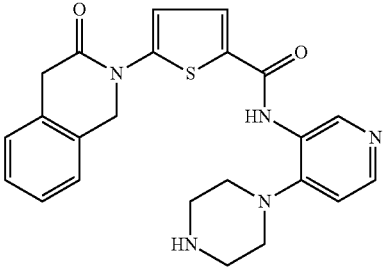
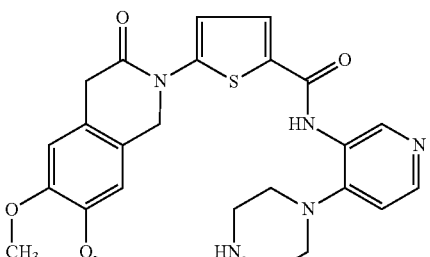
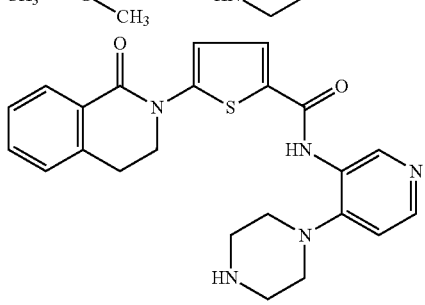

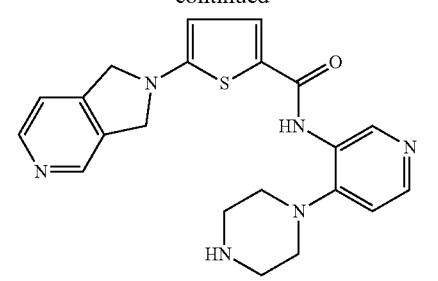
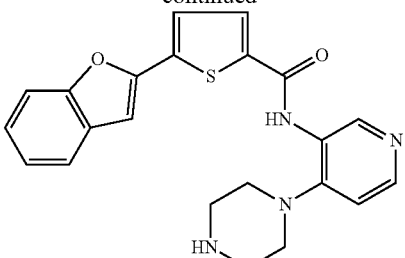
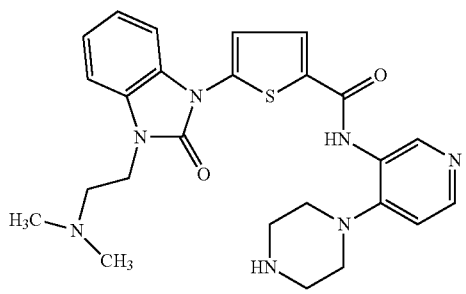
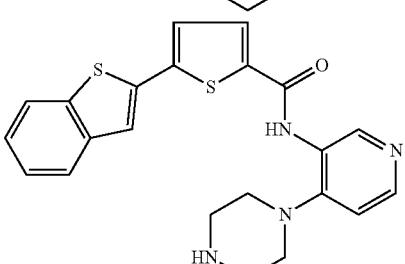
or a pharmaceutically acceptable salt, solvate, ester or prodrug thereof.
In another embodiment of the present invention is a heterocyclic amide derivative selected from the group consisting of:
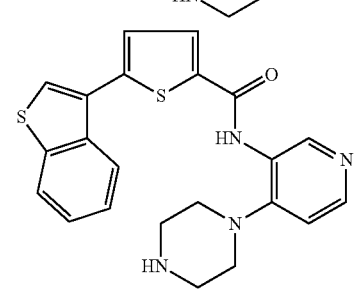
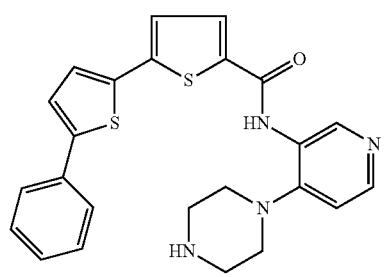
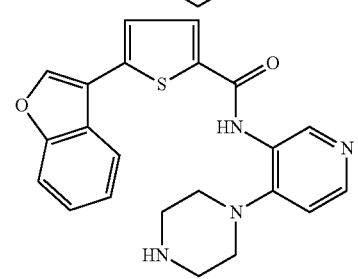
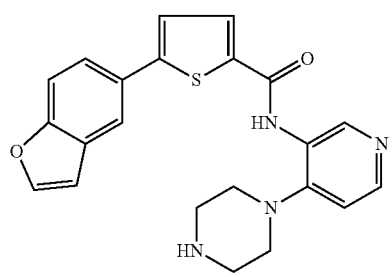
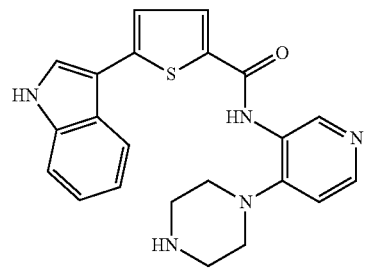
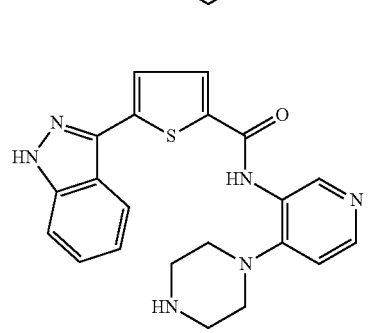

-continued
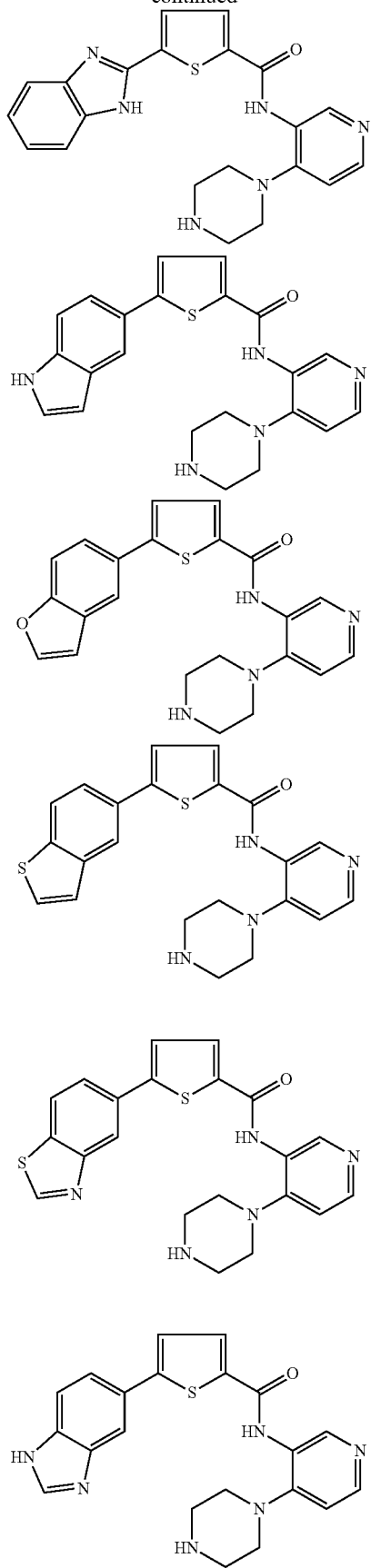
-continued
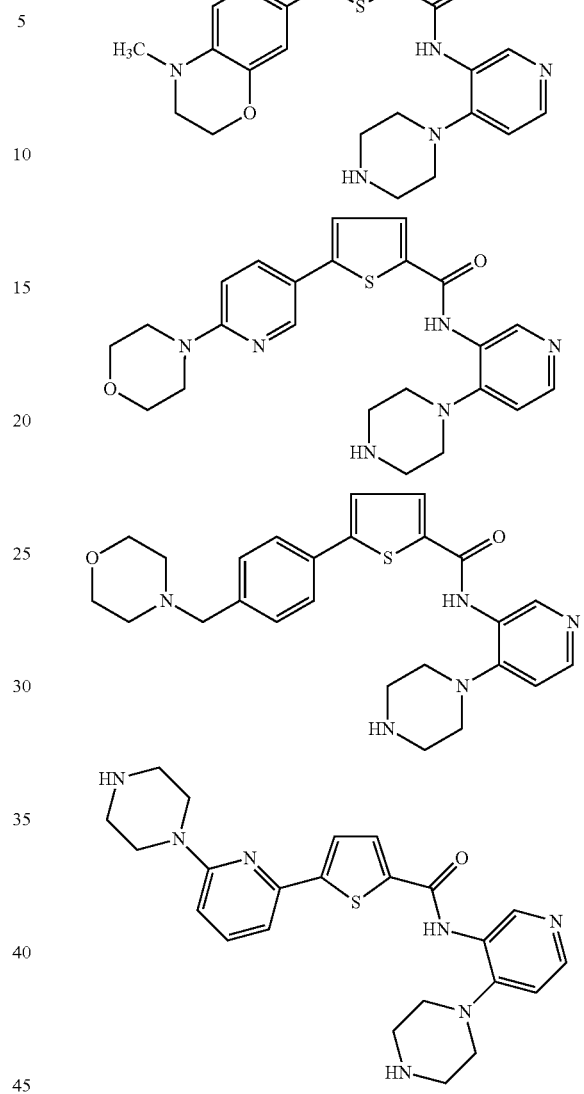
or a pharmaceutically acceptable salt, solvate, ester or prodrug thereof.
In another embodiment of the present invention is a heterocyclic amide derivative selected from the group consisting of:
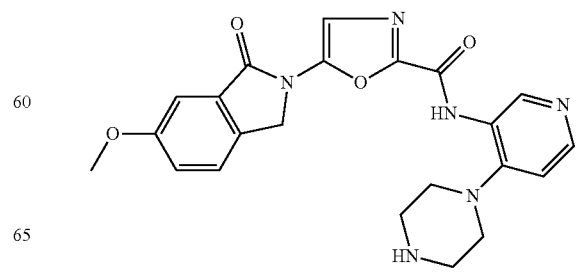

73
-continued
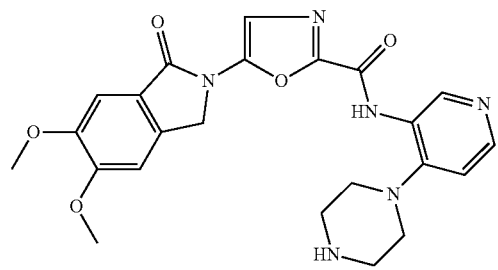
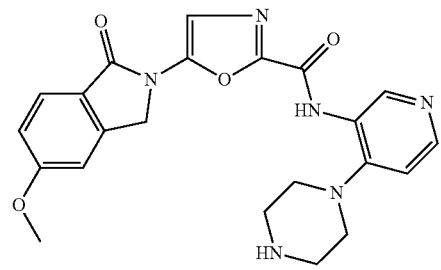
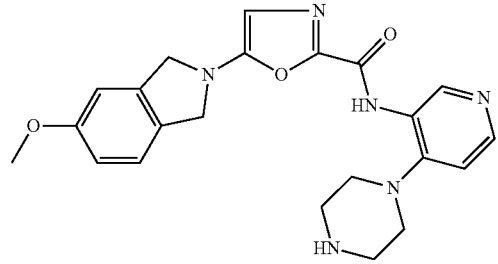
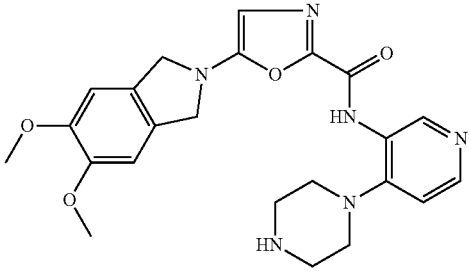
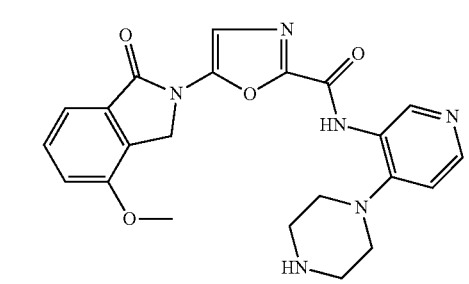
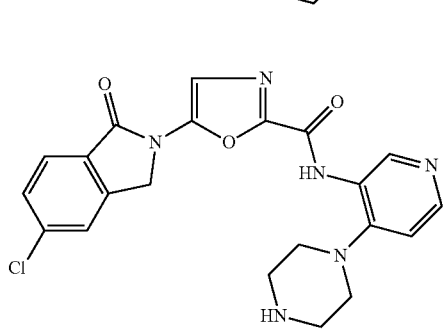
74
-continued
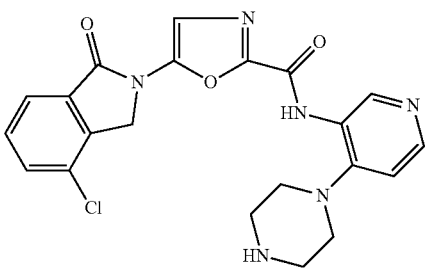
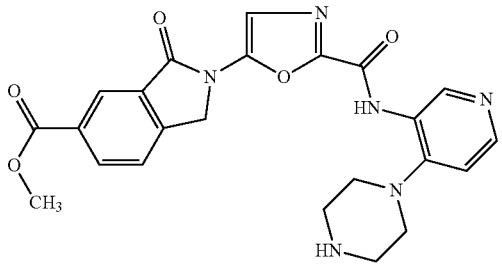
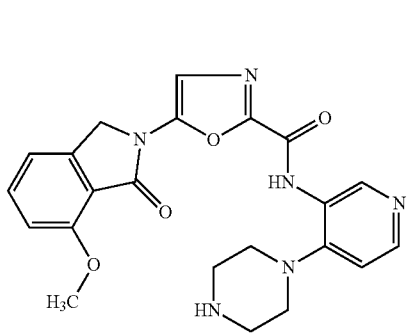
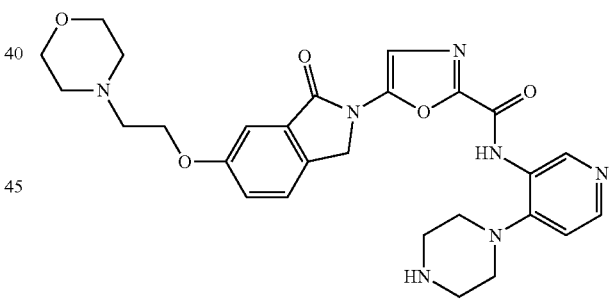
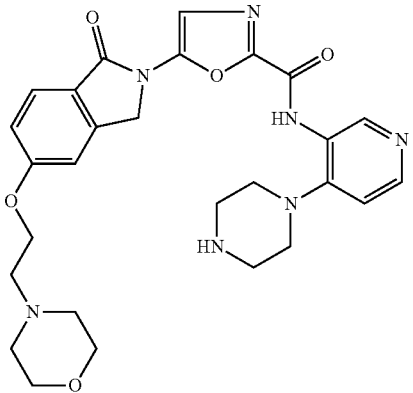

75
-continued
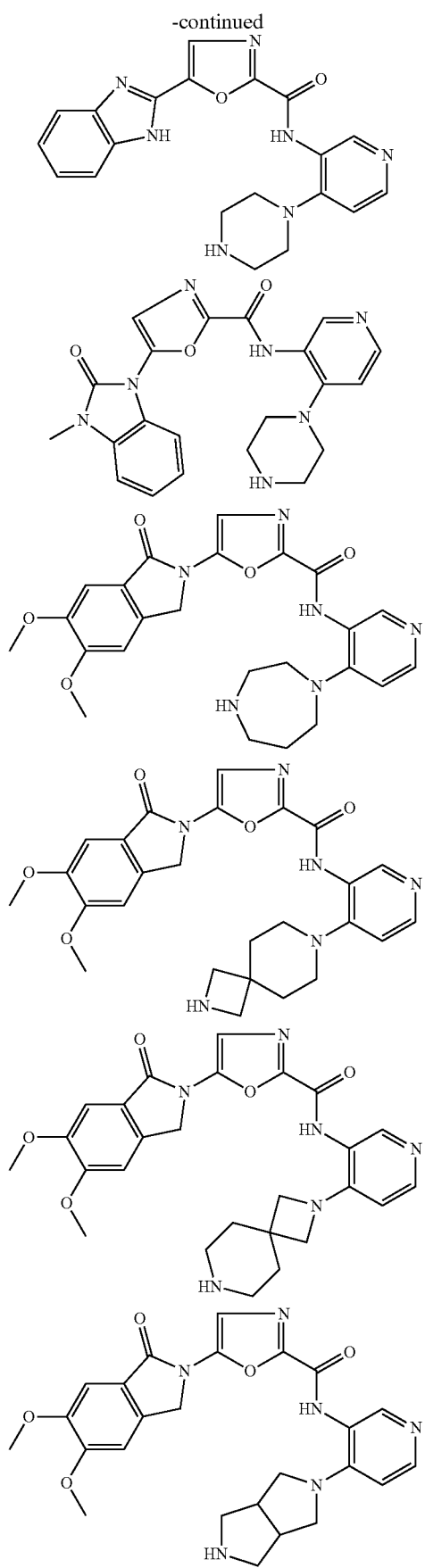
76
-continued
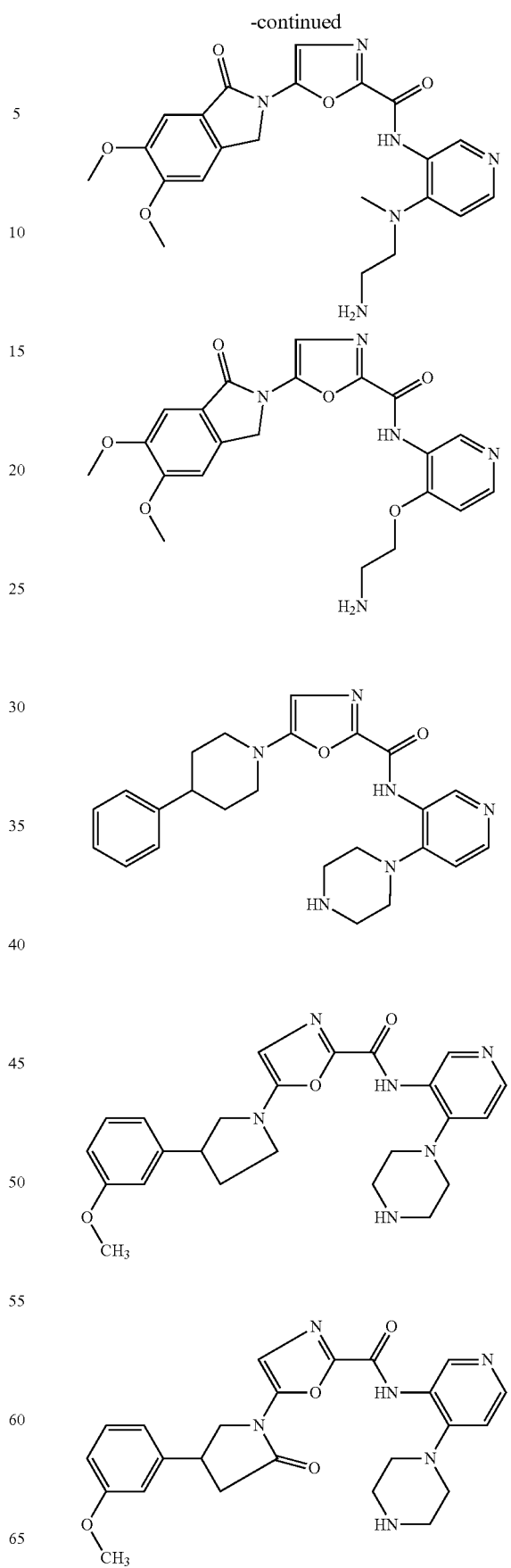

77
-continued
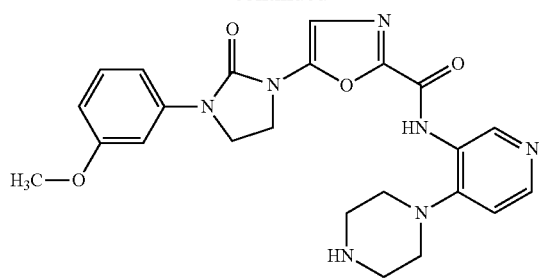
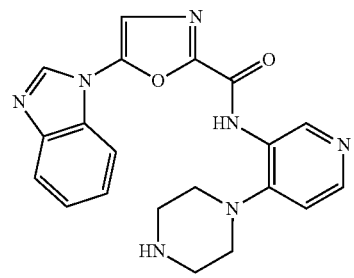
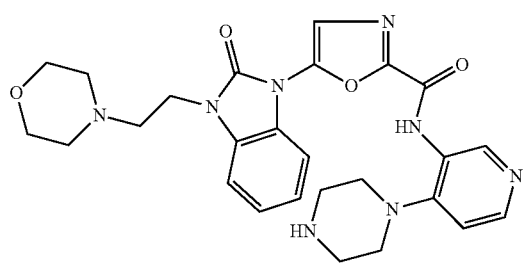
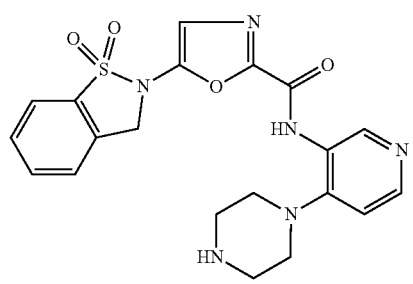
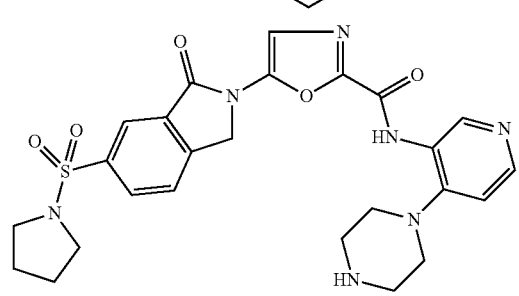
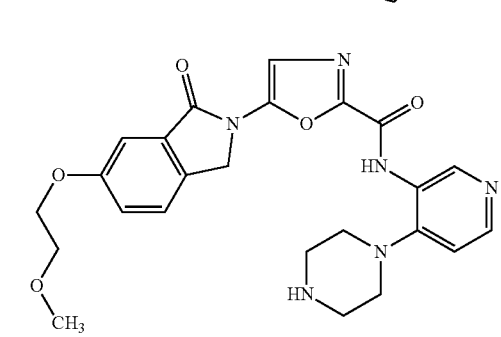
78
-continued
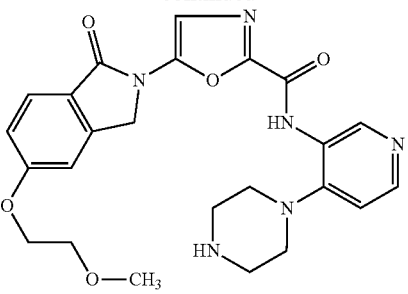
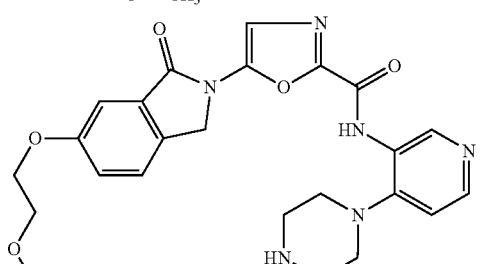
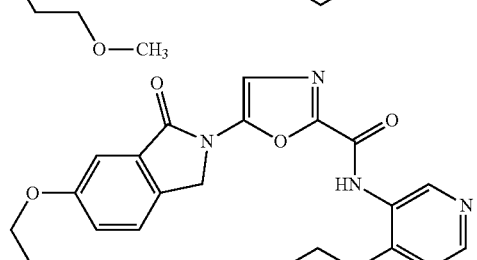
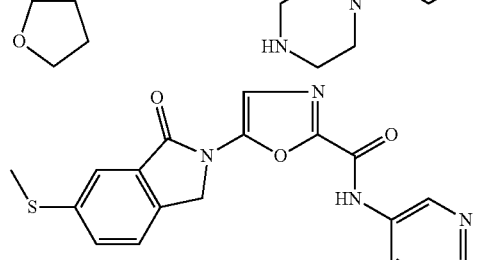
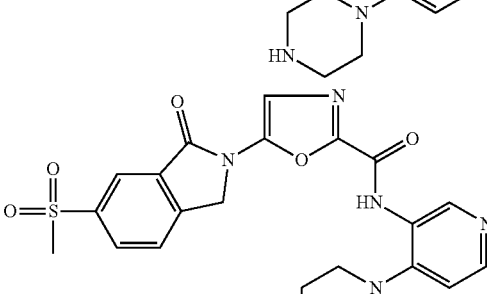
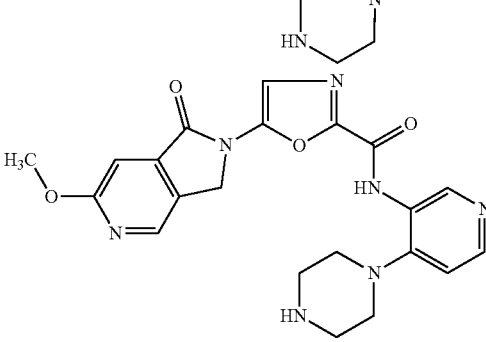

-continued
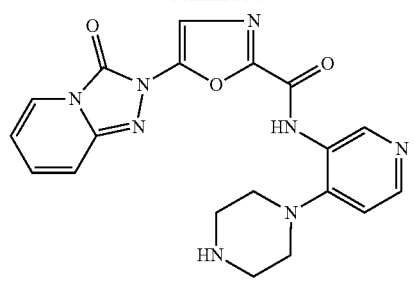
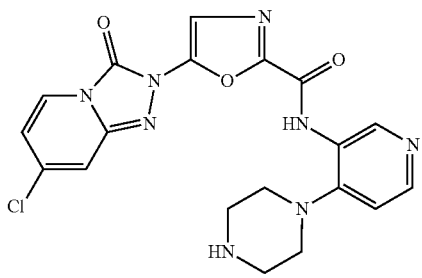
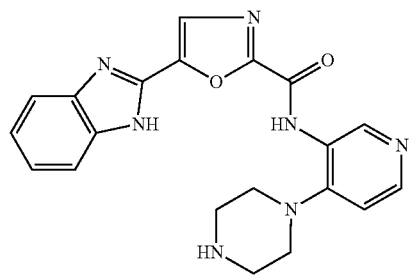
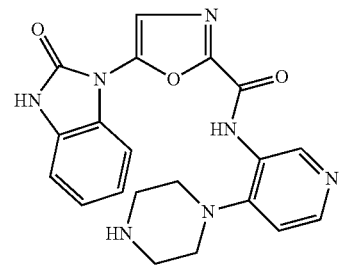
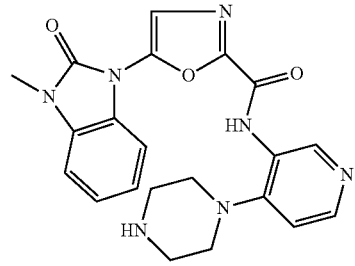
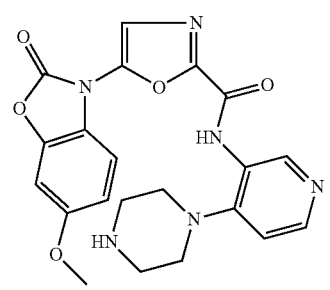
-continued
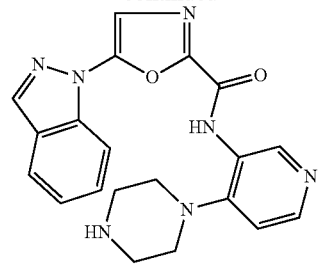
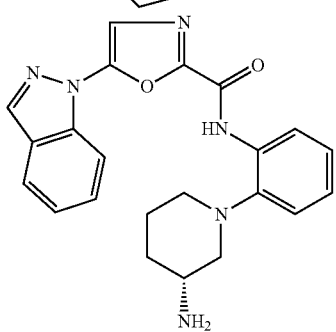
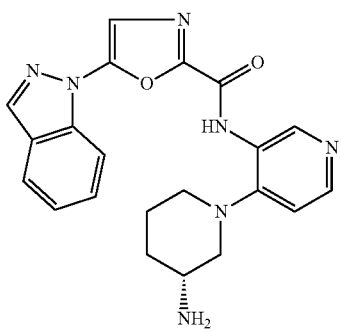
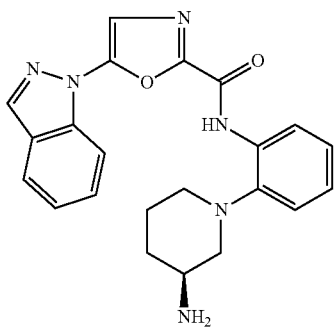
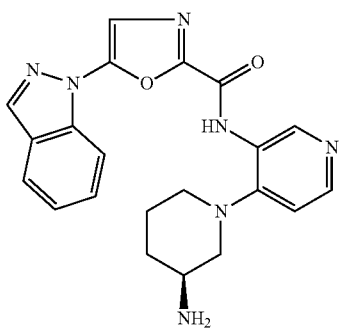

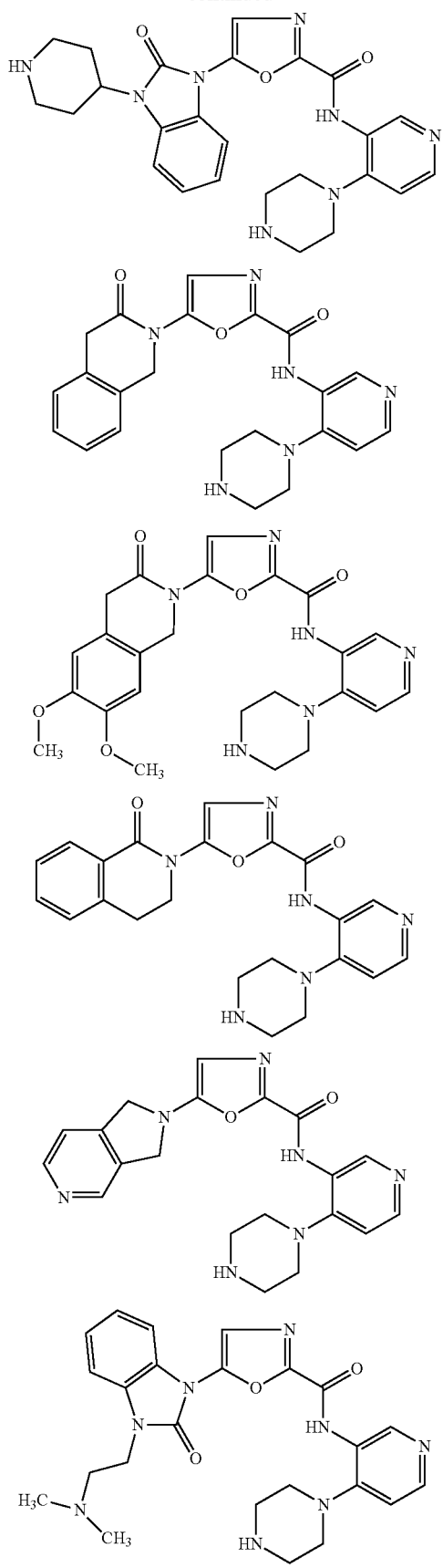
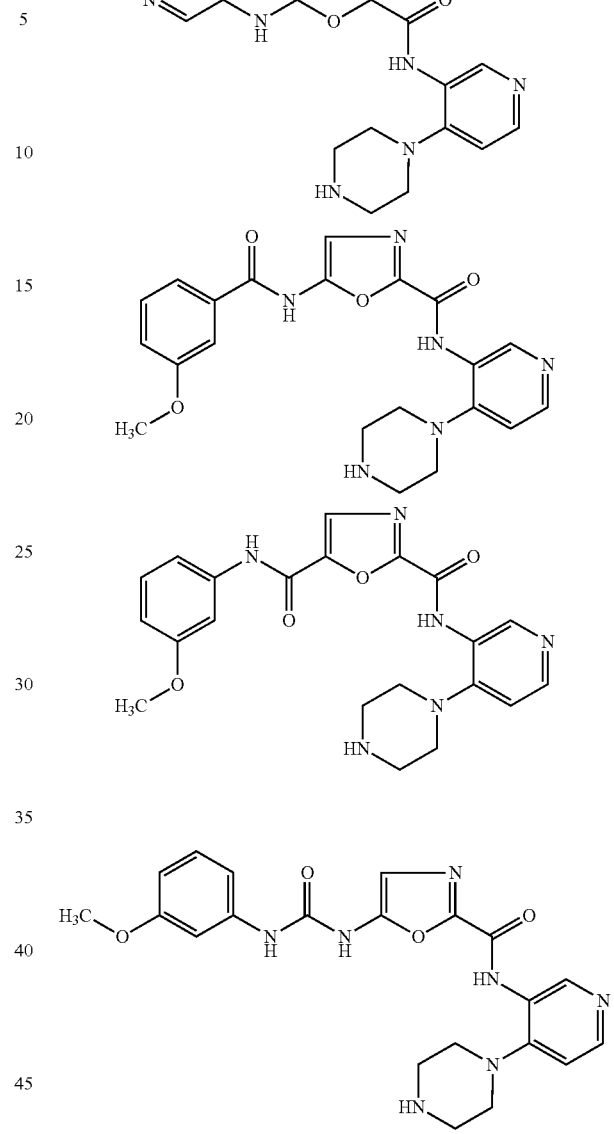
or a pharmaceutically acceptable salt, solvate, ester or prodrug thereof.
In another embodiment of the present invention is a heterocyclic amide derivative selected from the group consisting of:
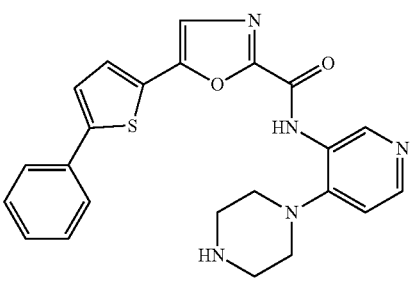

-continued
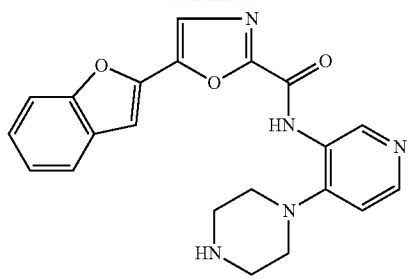
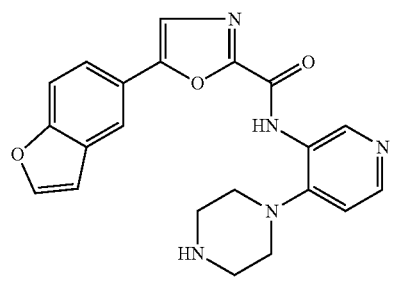
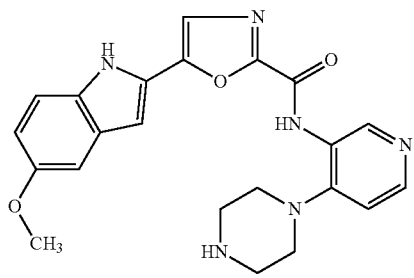
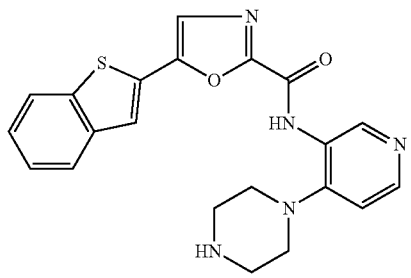
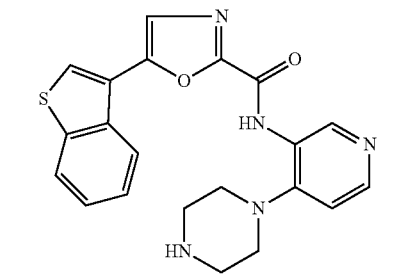
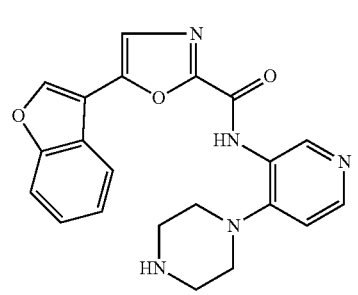
-continued
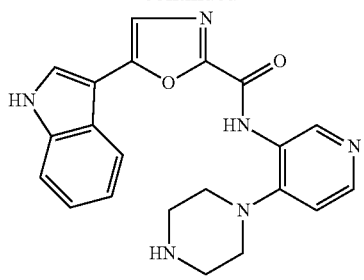
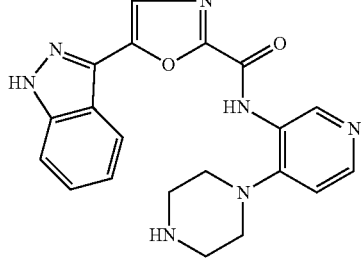
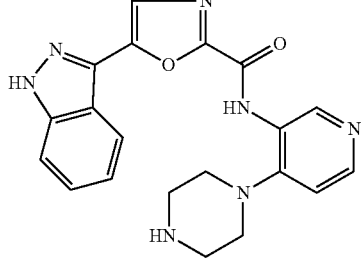
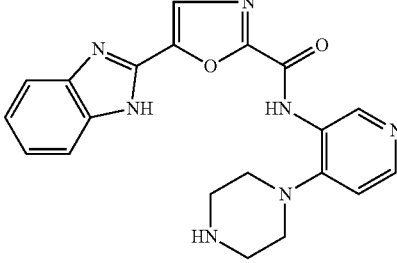
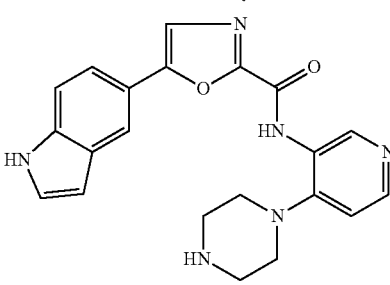
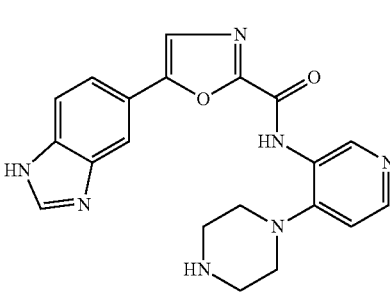

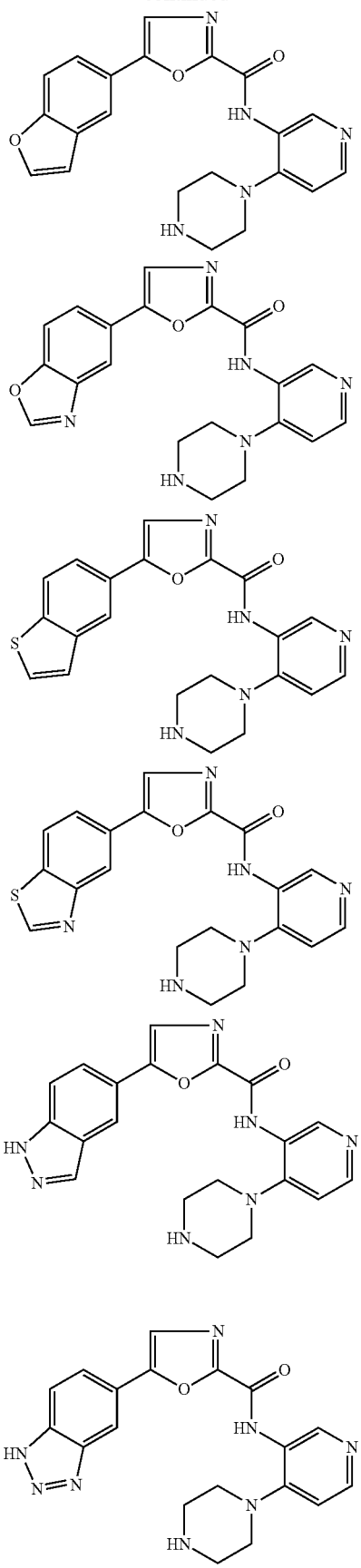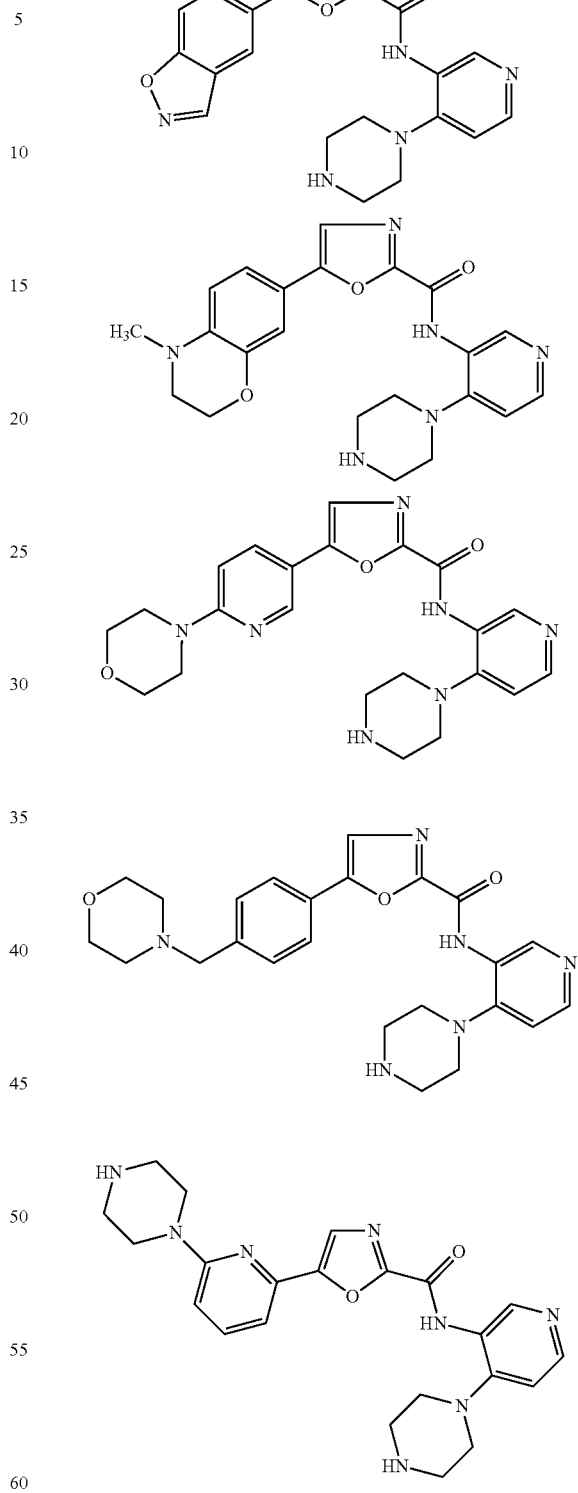
or a pharmaceutically acceptable salt, solvate, ester or prodrug thereof.
In another embodiment of the present invention is a heterocyclic amide derivative selected from the group consisting of:

87
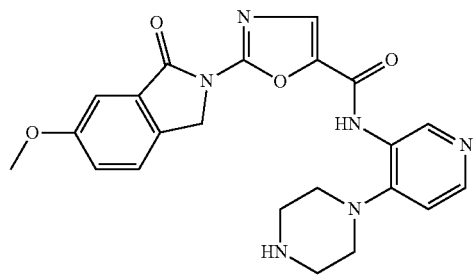
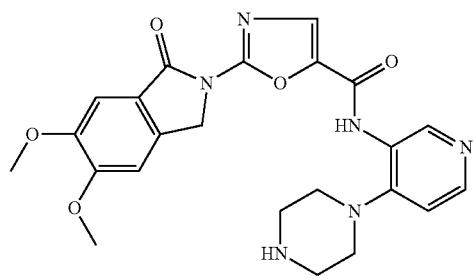
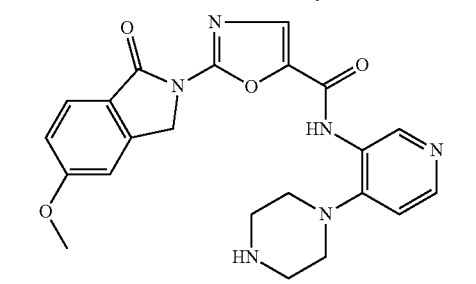
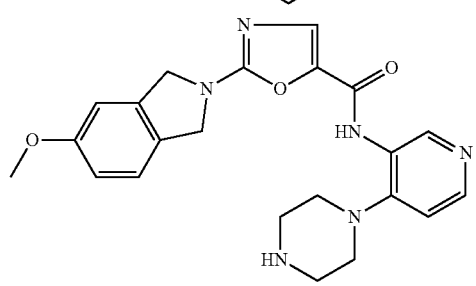
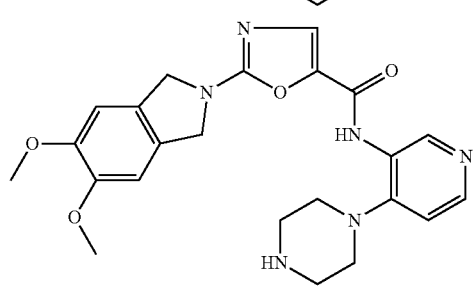
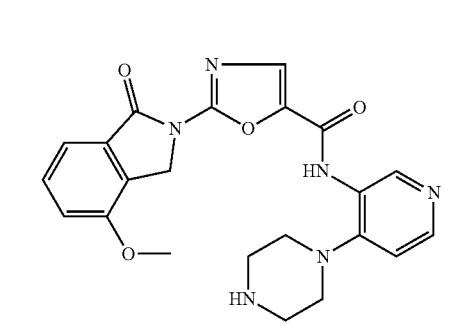
88
-continued
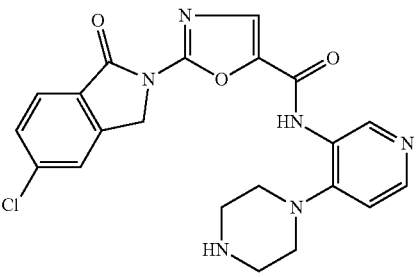
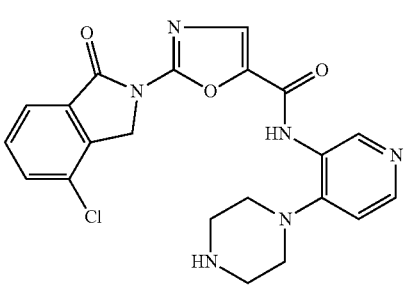
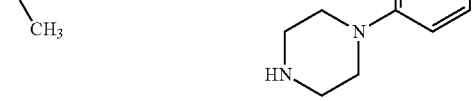
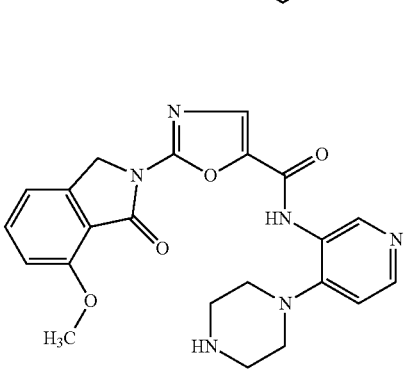
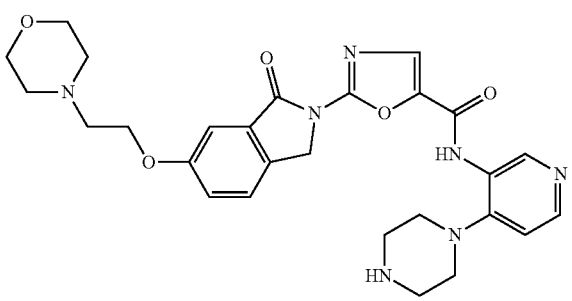

89
-continued
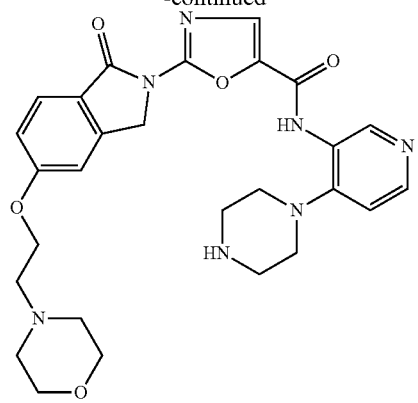
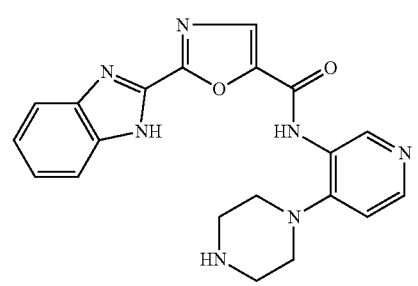
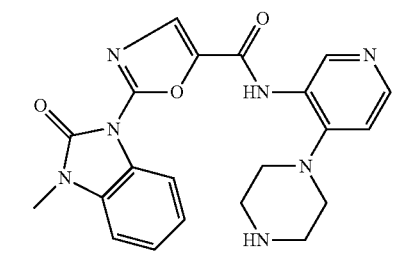
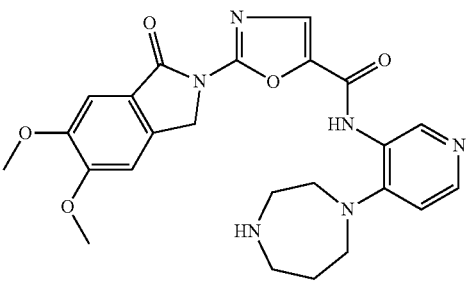
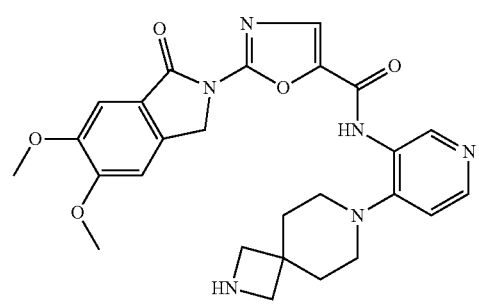
90
-continued
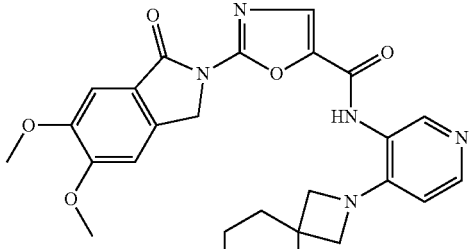
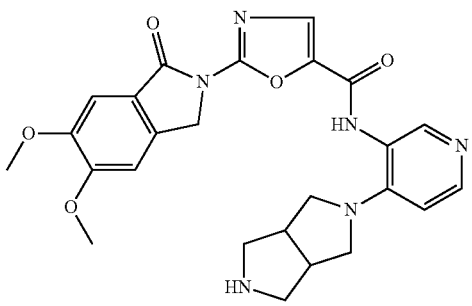
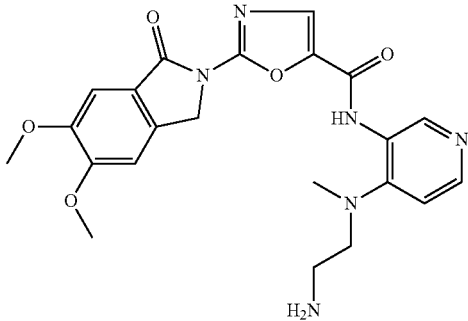
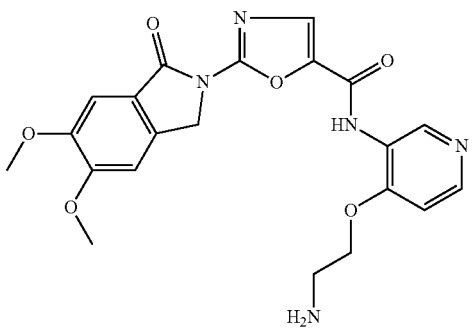
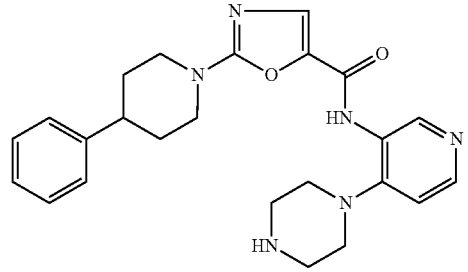

-continued
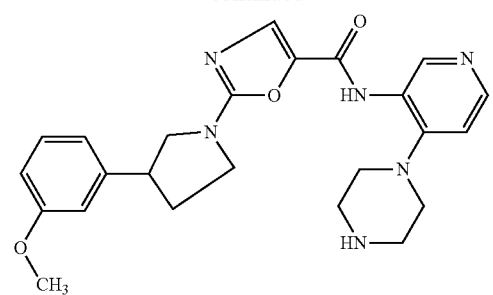
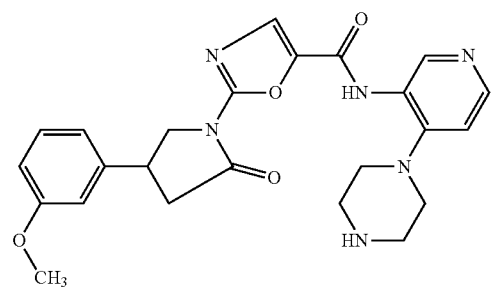
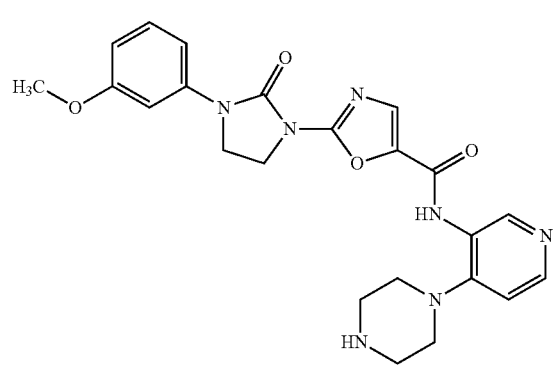
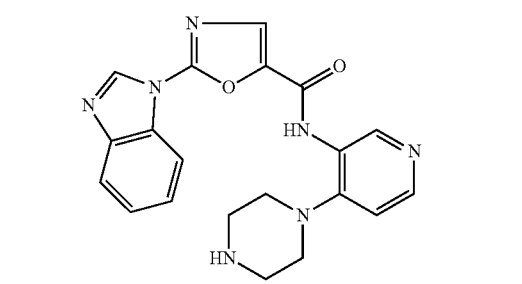
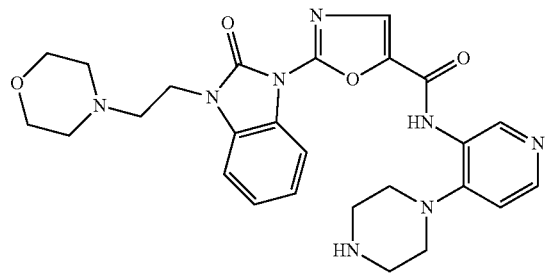
-continued
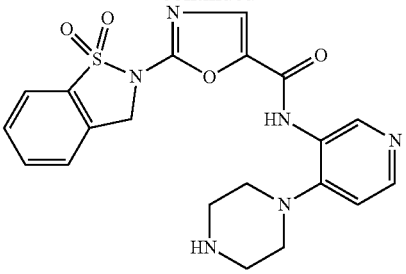
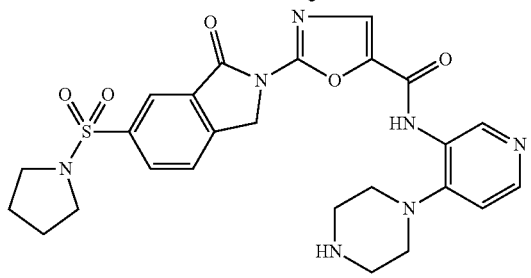
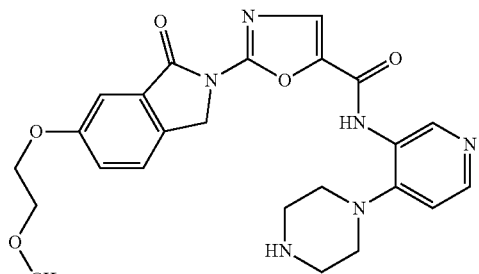
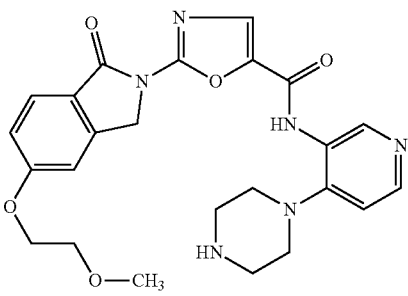
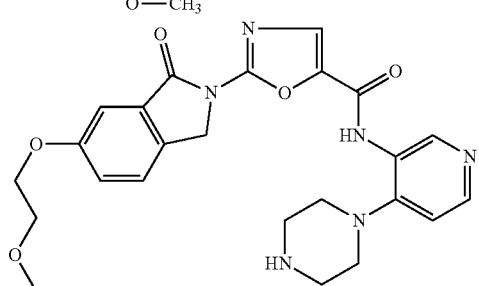
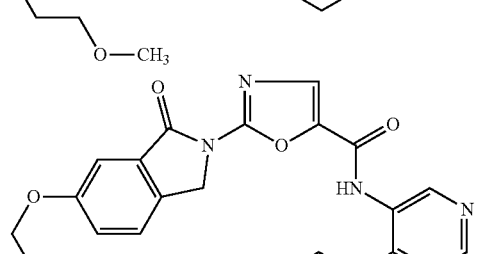

93
-continued
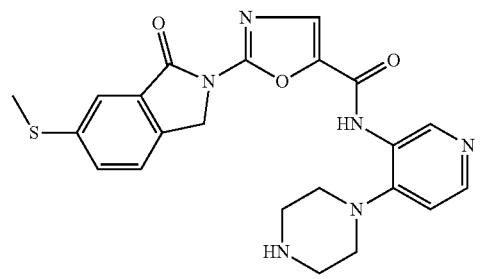
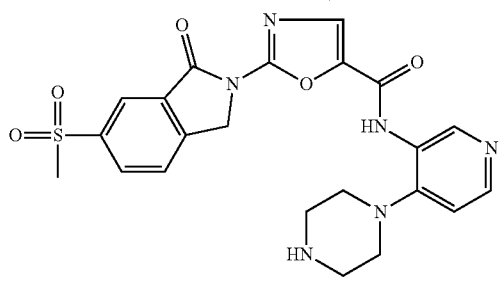
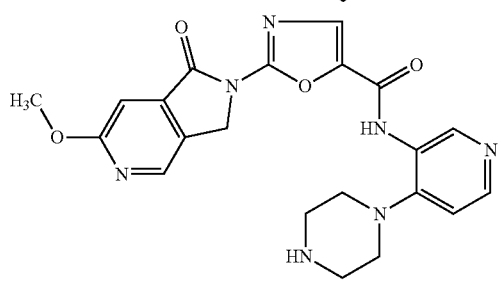
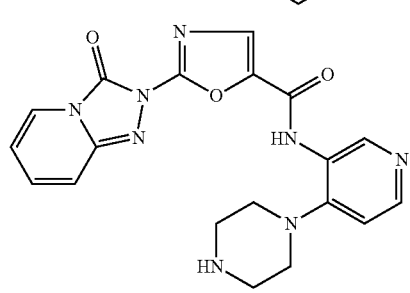
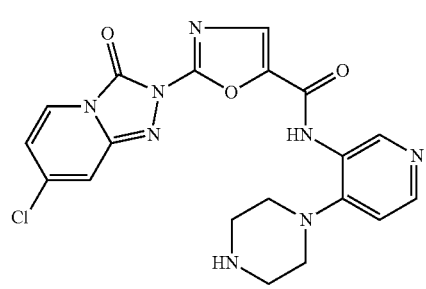
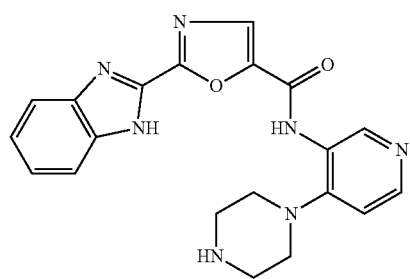
94
-continued
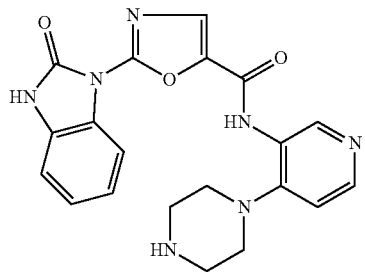
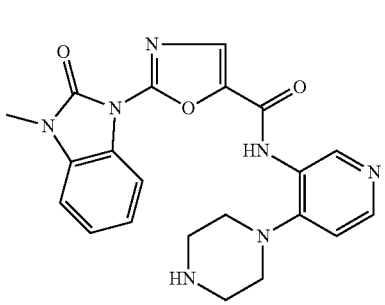
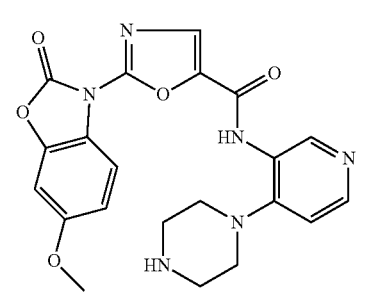
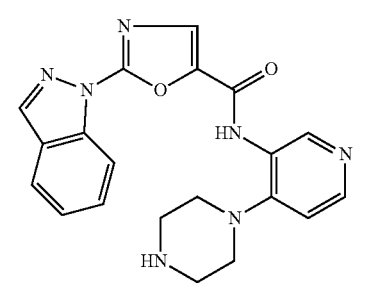
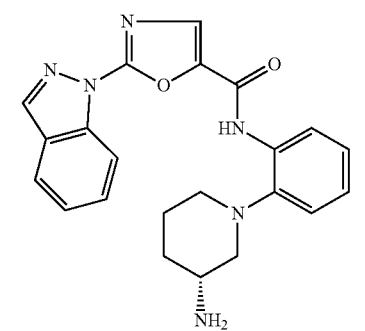

95
-continued
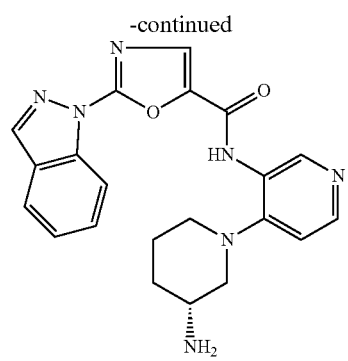
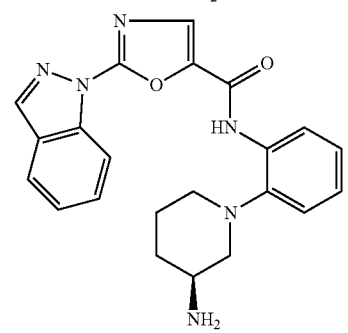
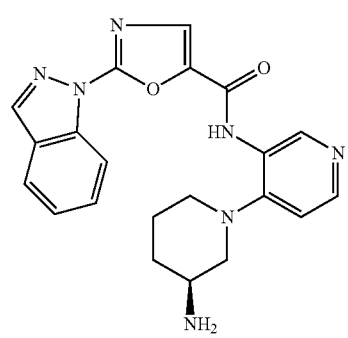
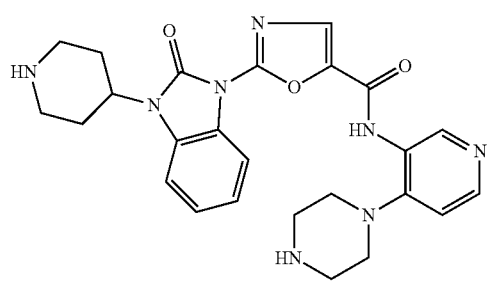
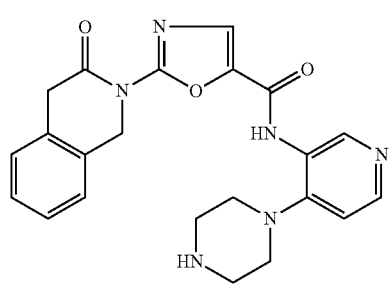
96
-continued
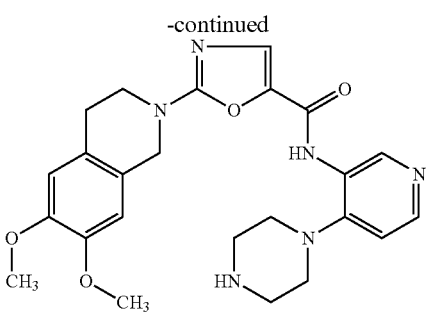
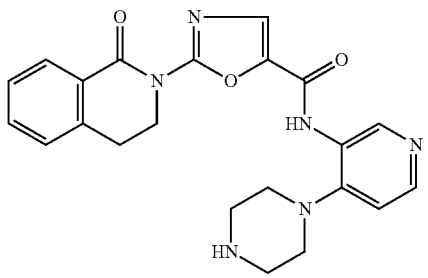
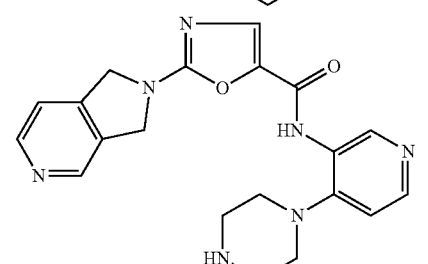
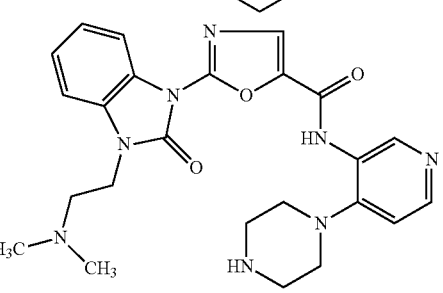
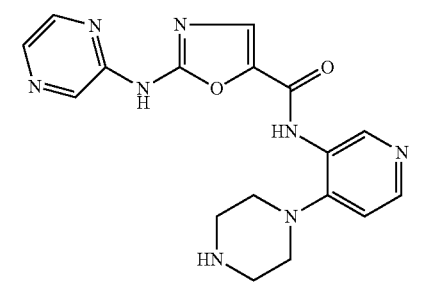
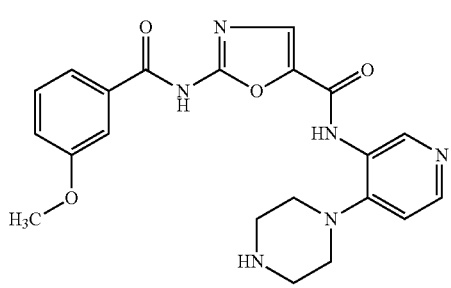

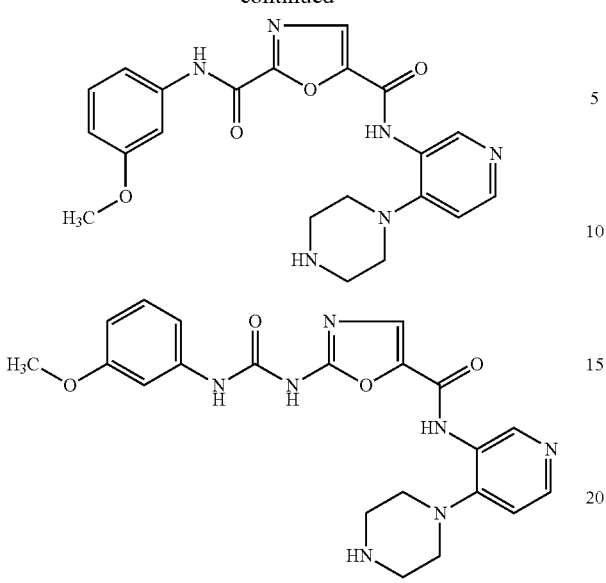
or a pharmaceutically acceptable salt, solvate, ester or prodrug thereof.
In another embodiment of the present invention is a heterocyclic amide derivative selected from the group consisting of:
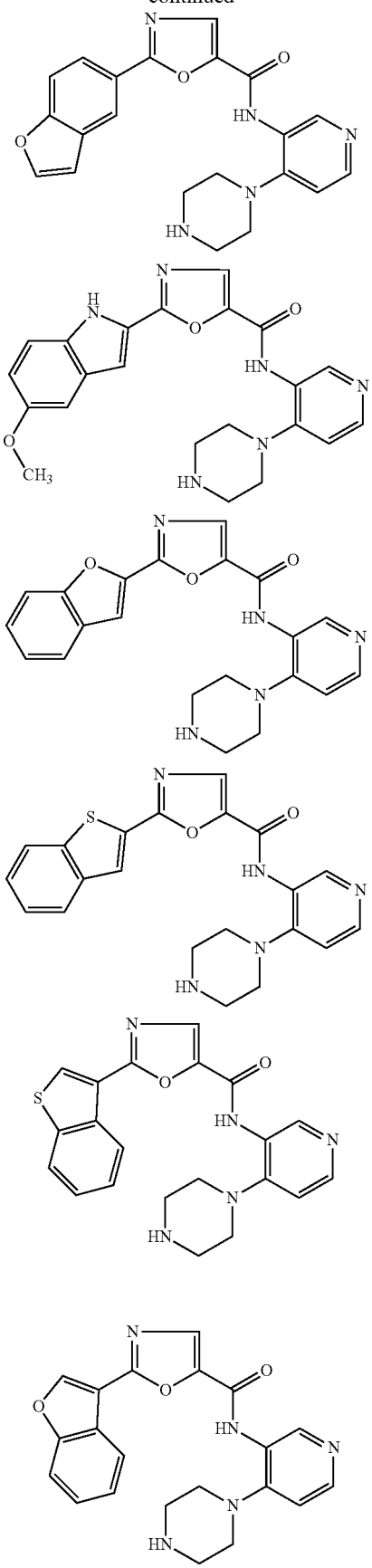

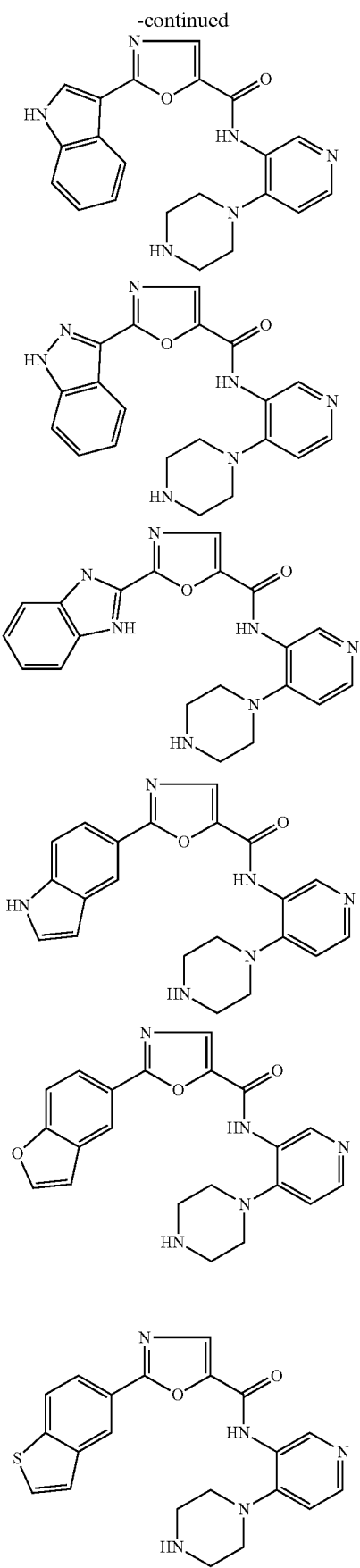
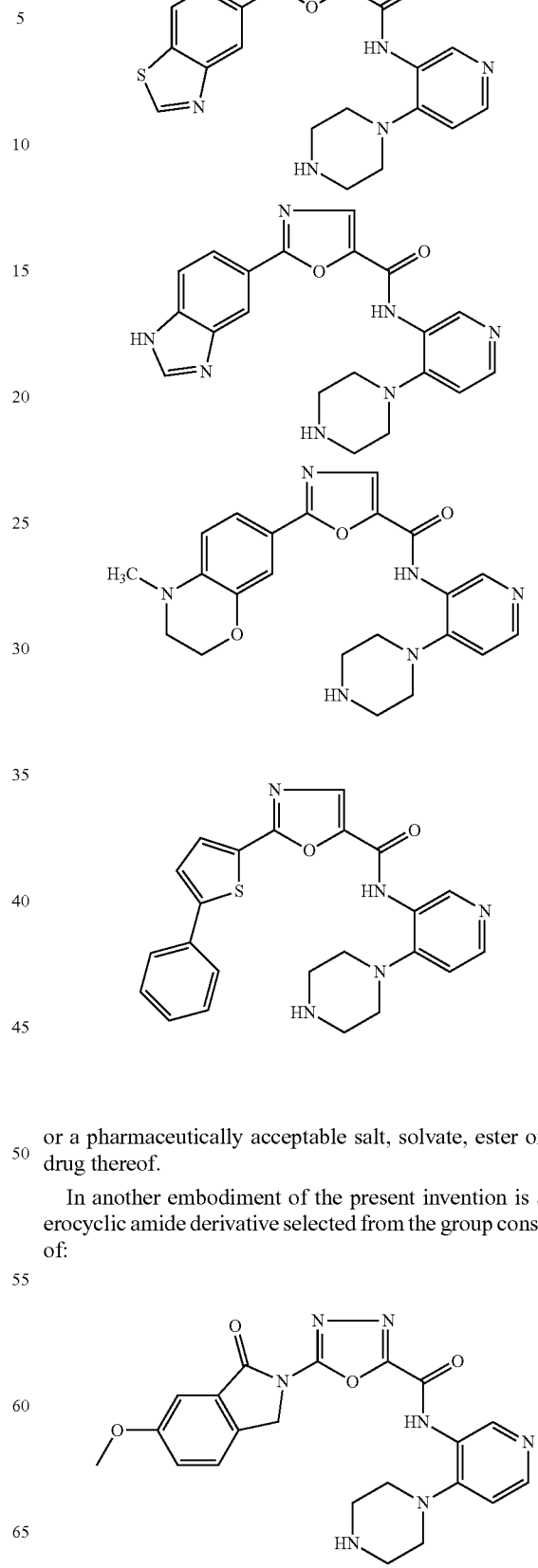
or a pharmaceutically acceptable salt, solvate, ester or prodrug thereof.
In another embodiment of the present invention is a heterocyclic amide derivative selected from the group consisting of:
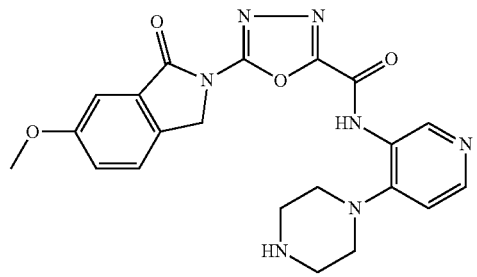

101
-continued
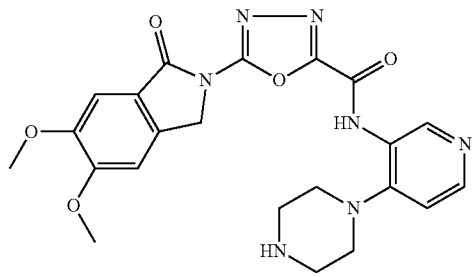
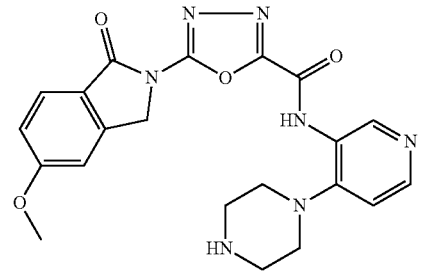
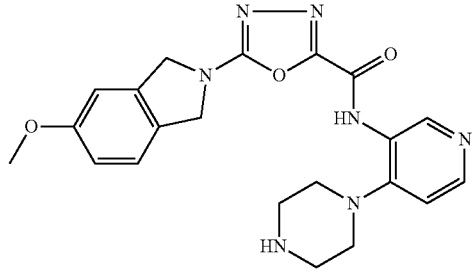
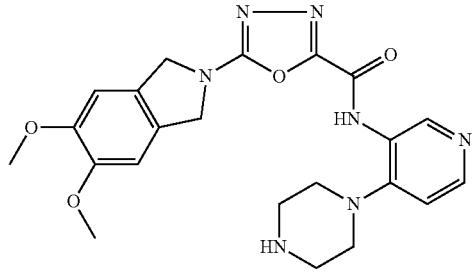
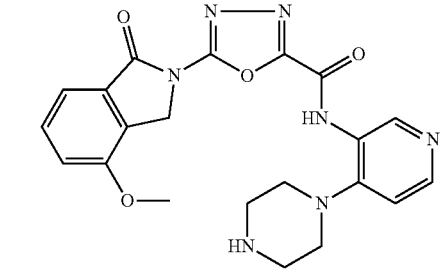
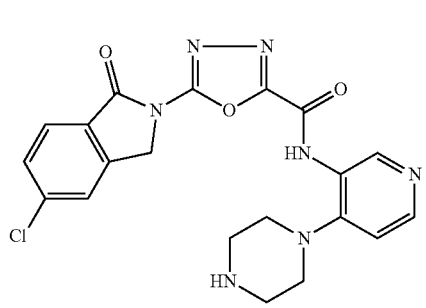
102
-continued
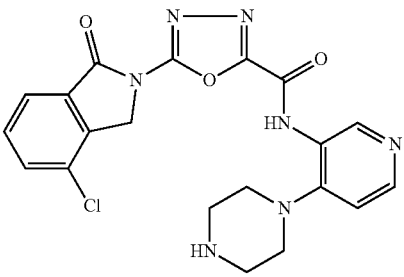
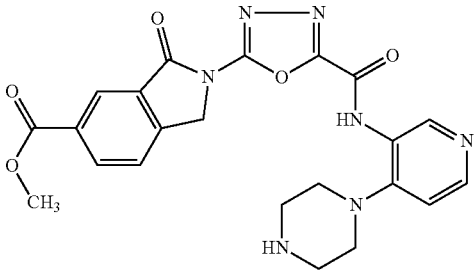
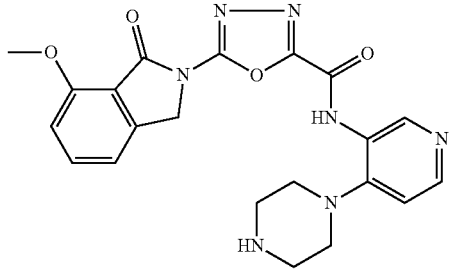
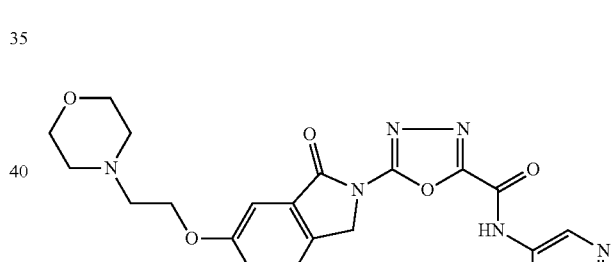
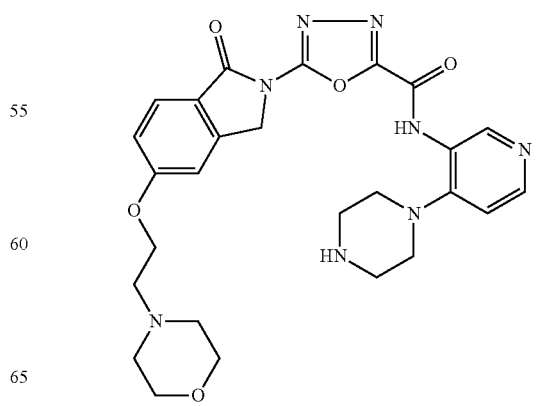

103
-continued
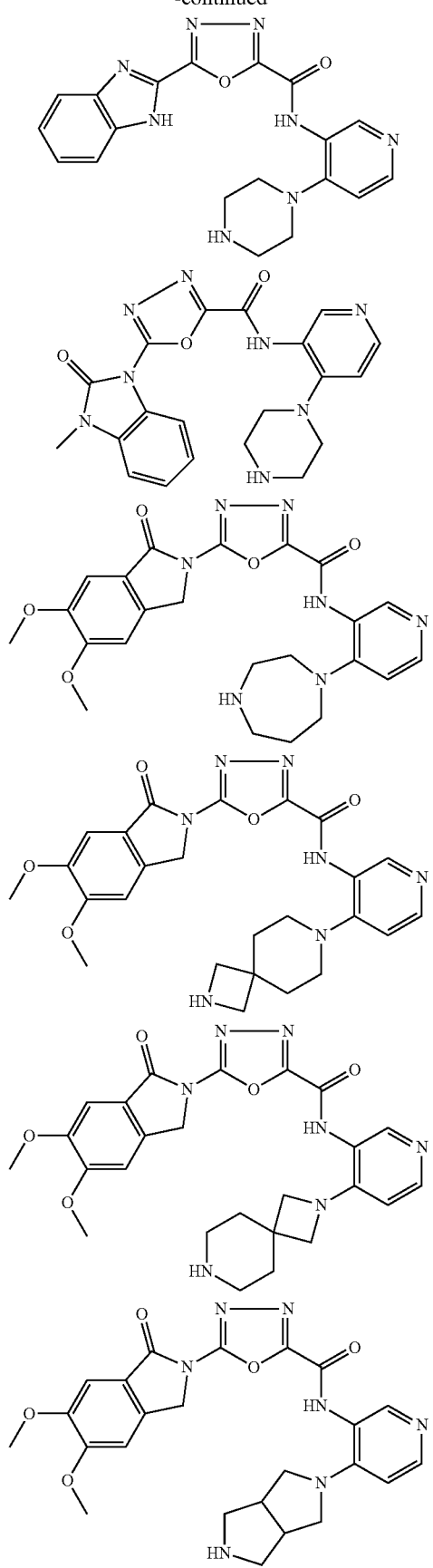
104
-continued
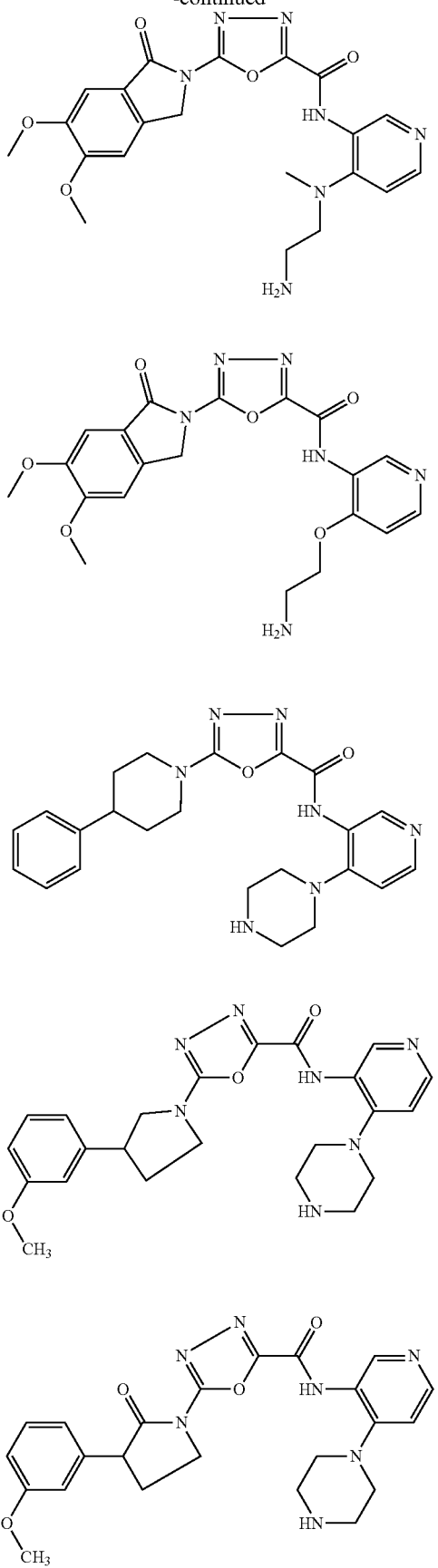

105
-continued
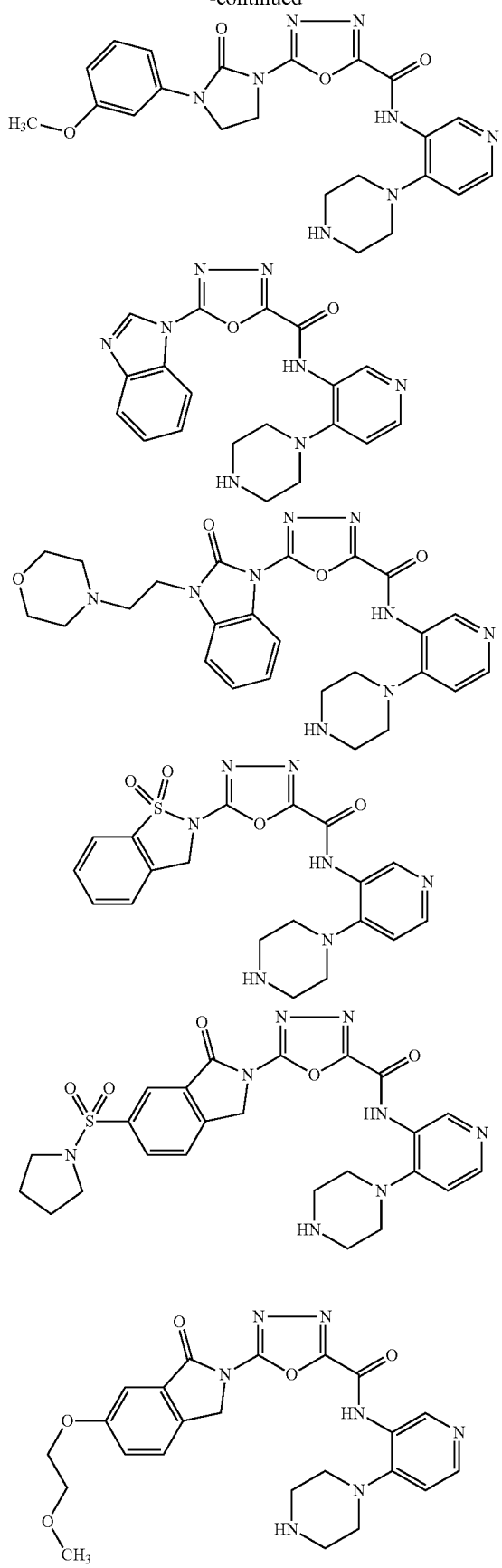
106
-continued
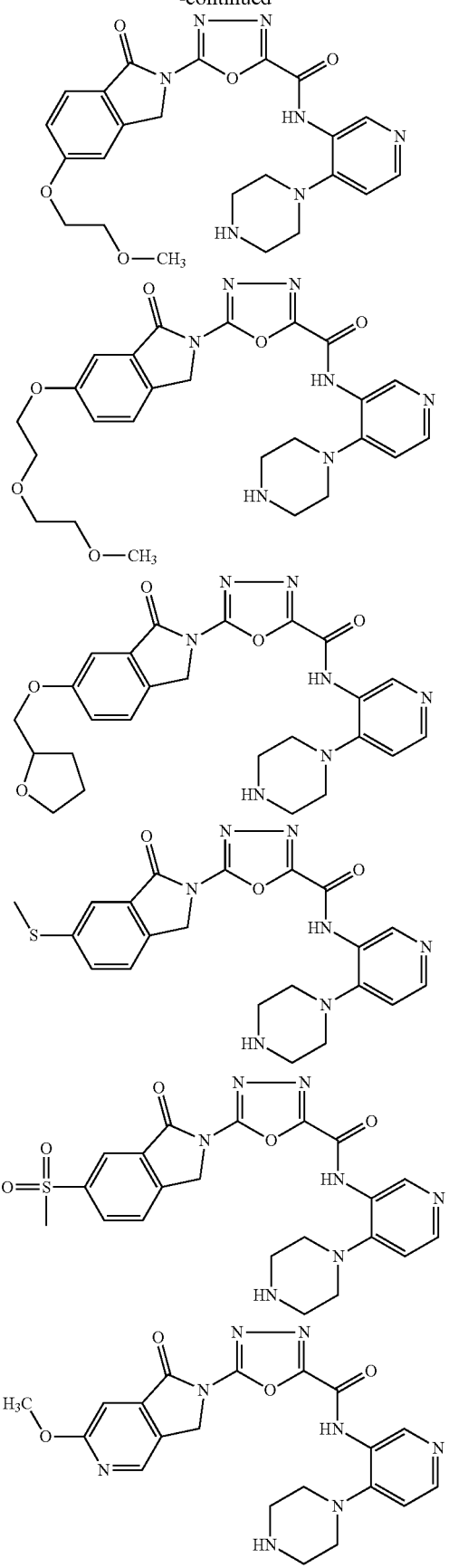

107
-continued
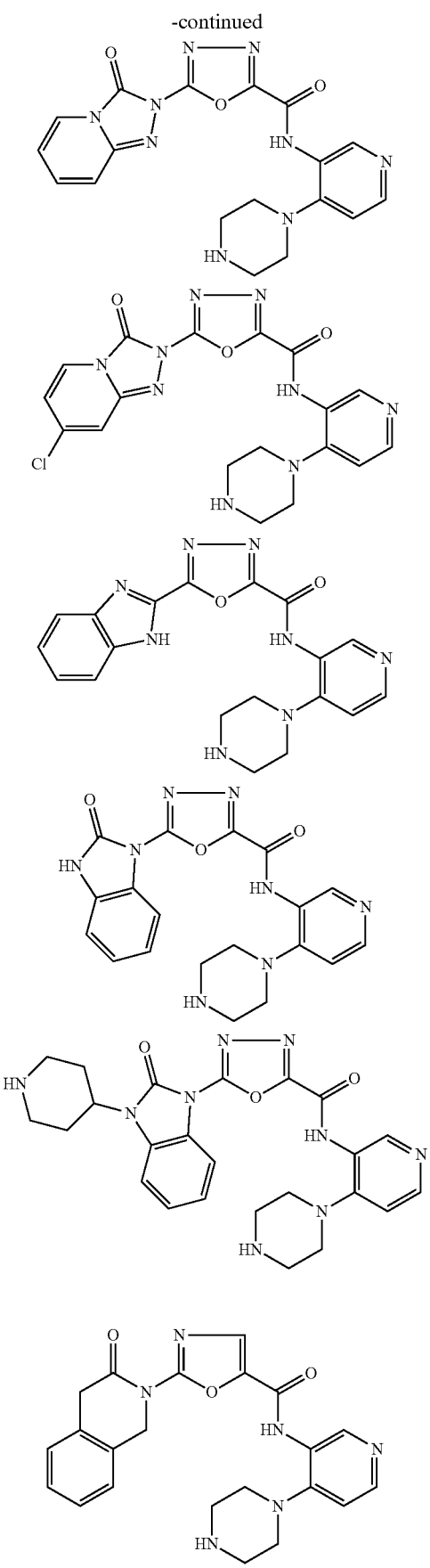
108
-continued
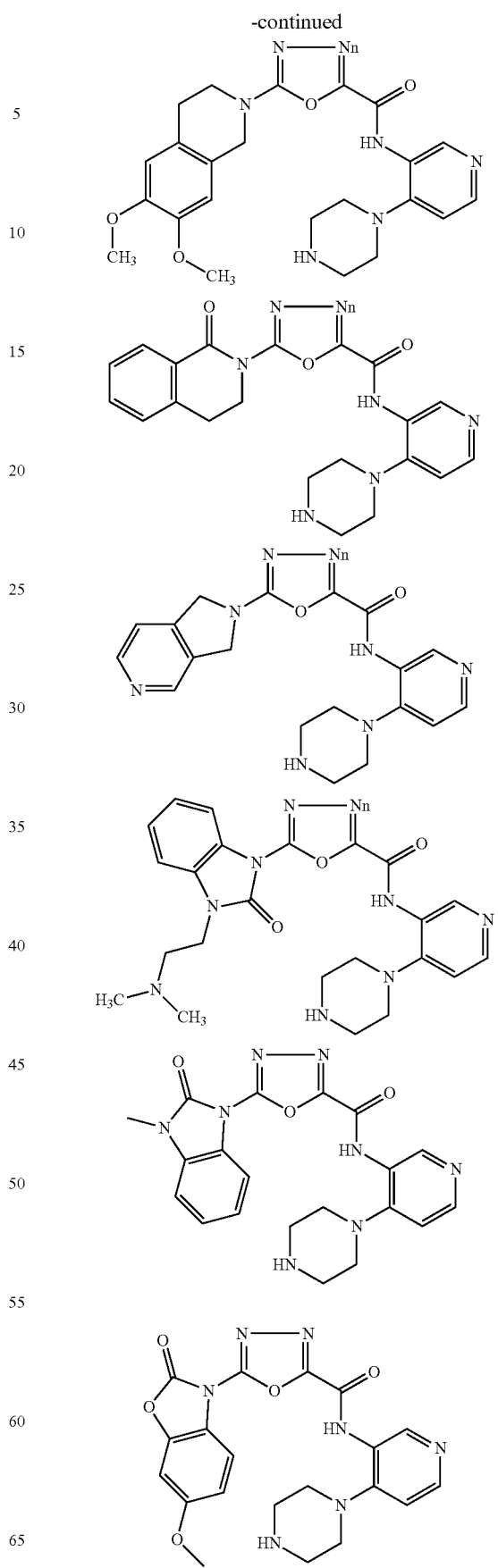

109
-continued
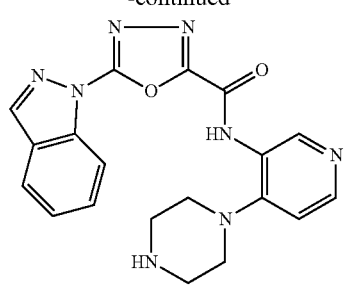
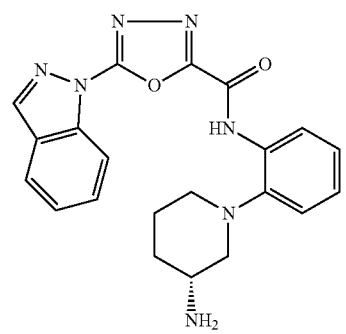
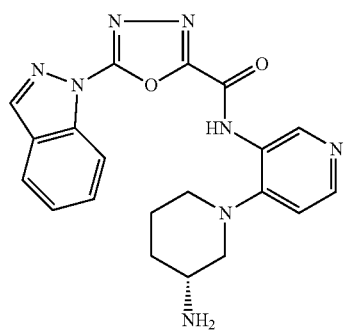
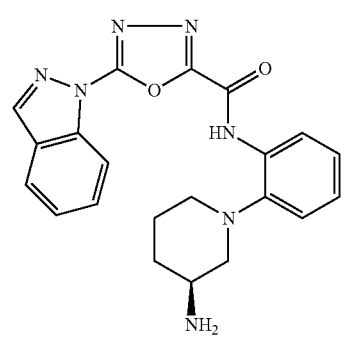
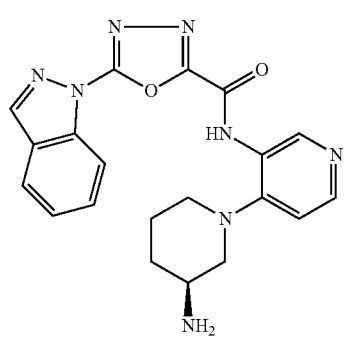
110
-continued
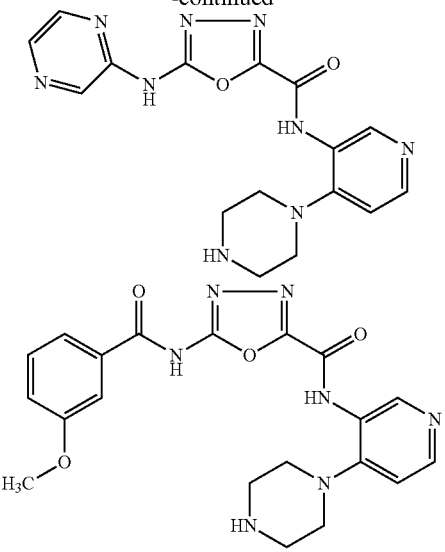
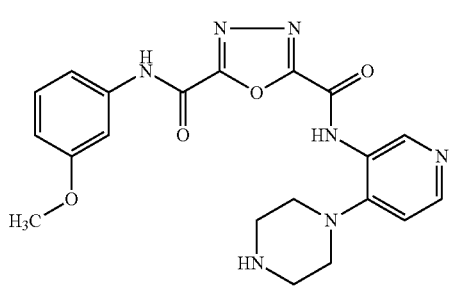
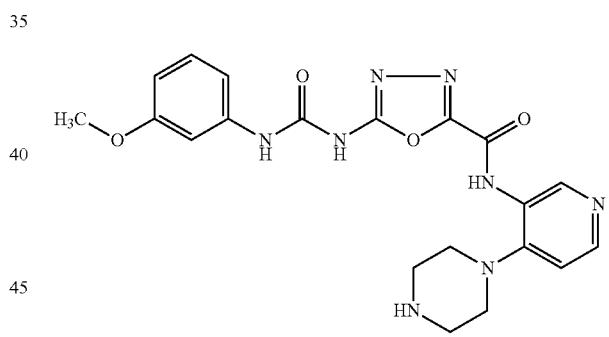
or a pharmaceutically acceptable salt, solvate, ester or prodrug thereof.
In another embodiment of the present invention is a heterocyclic amide derivative selected from the group consisting of:
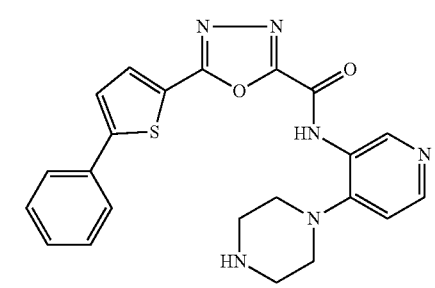

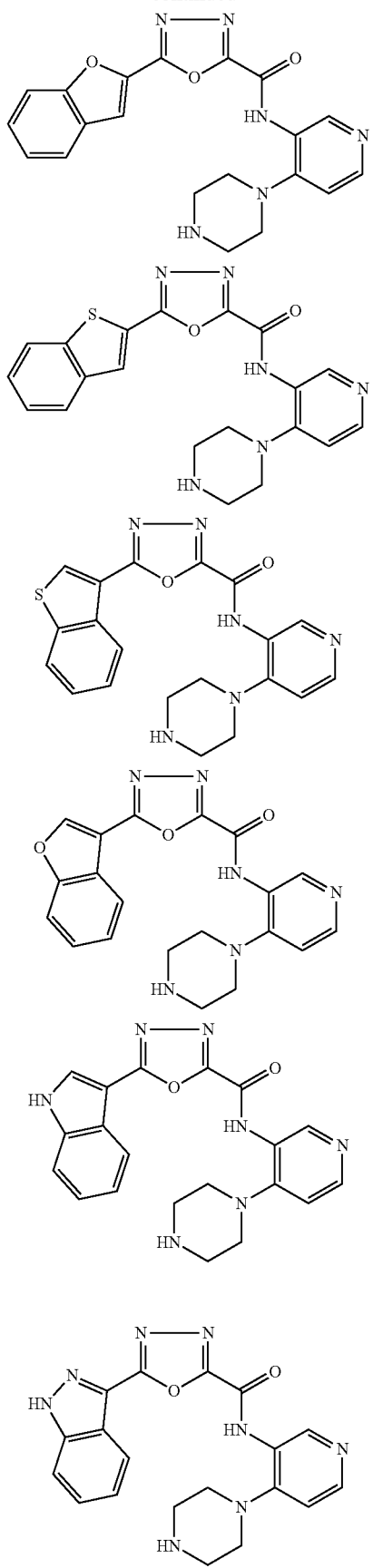
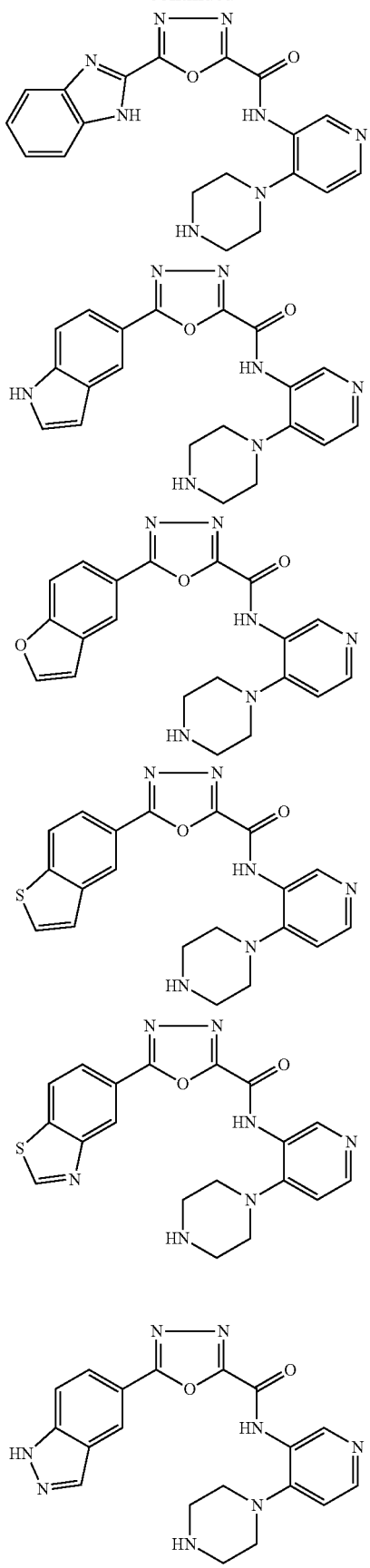

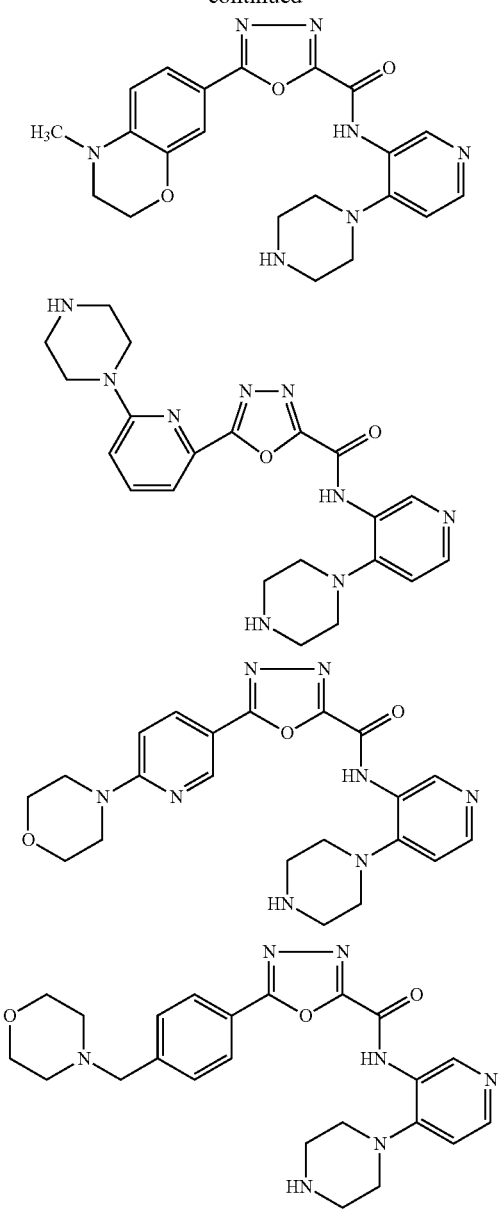
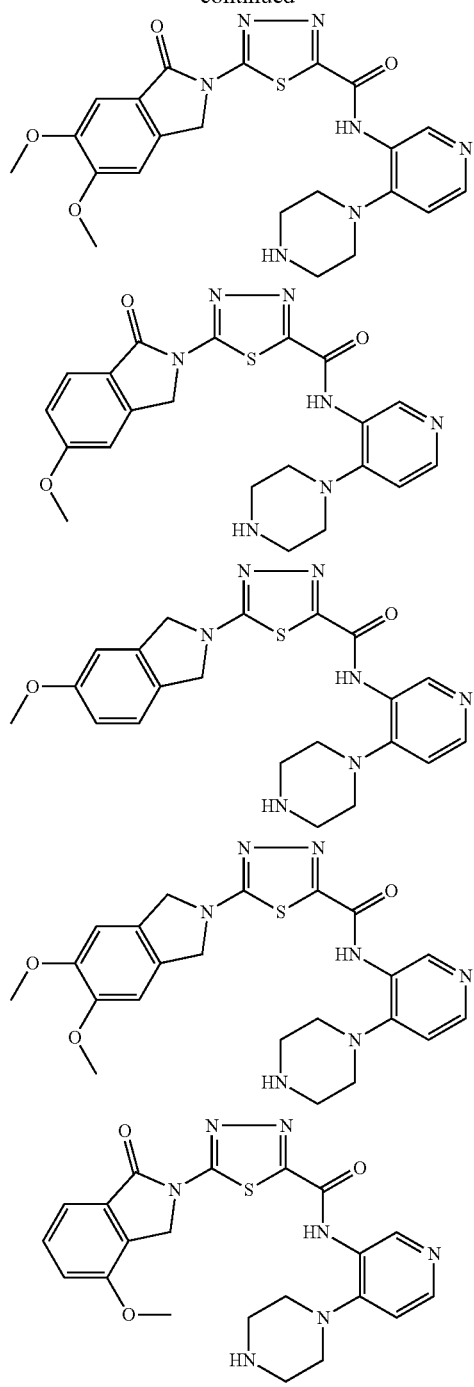
or a pharmaceutically acceptable salt, solvate, ester or prodrug thereof.
In another embodiment of the present invention is a heterocyclic amide derivative selected from the group consisting of:
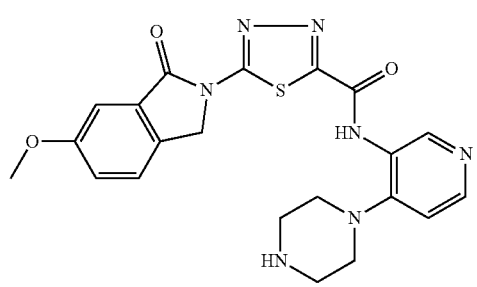
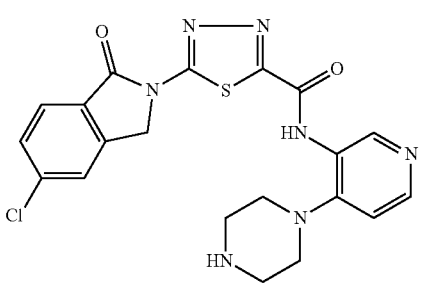

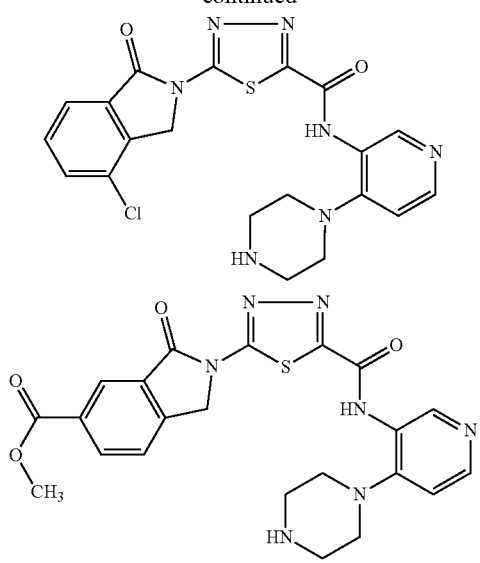
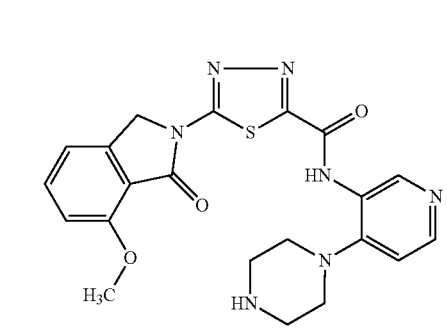
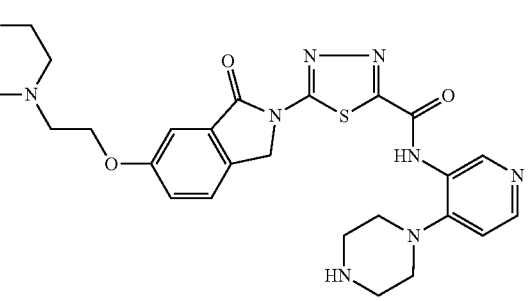
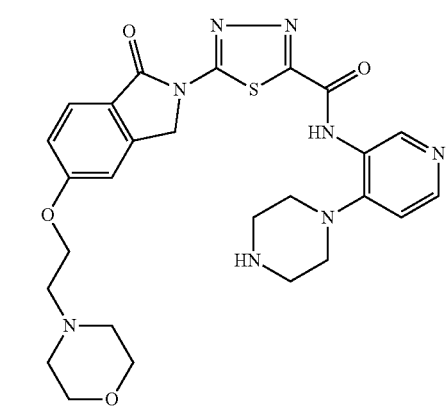
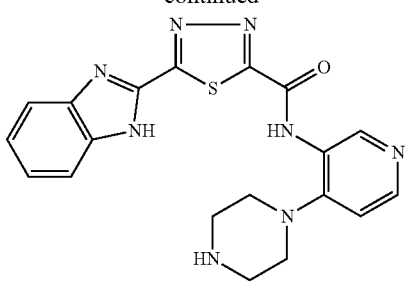
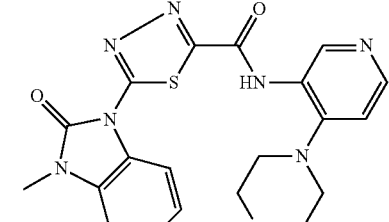
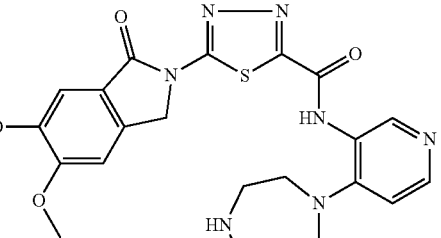
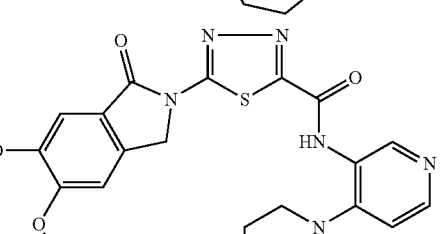
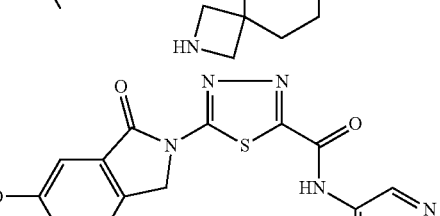
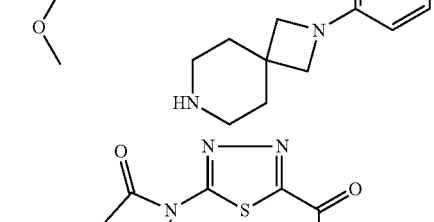
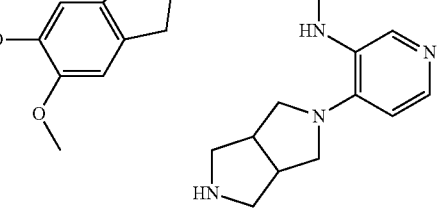

117
-continued
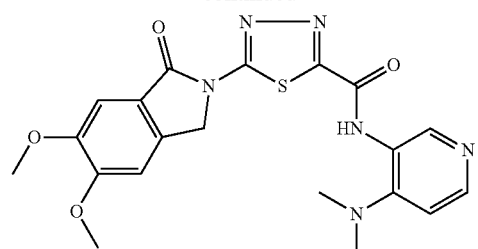
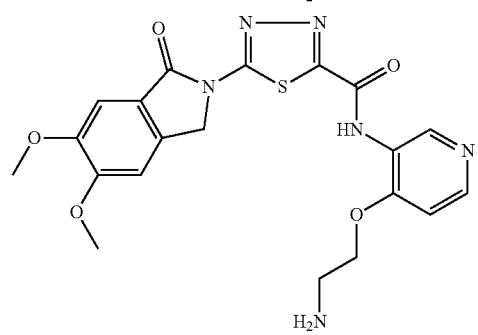
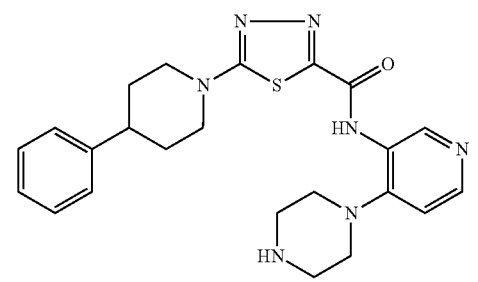
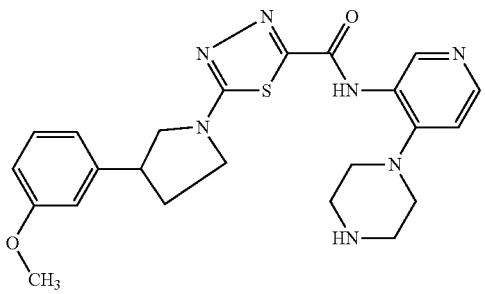
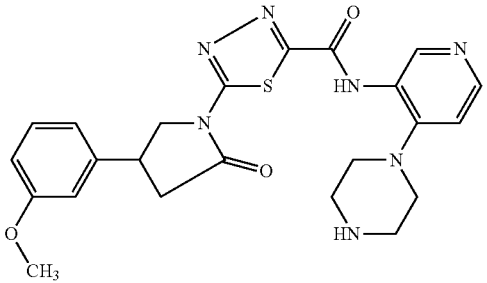
118
-continued
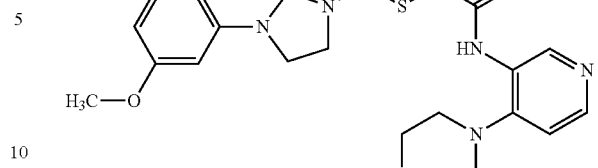
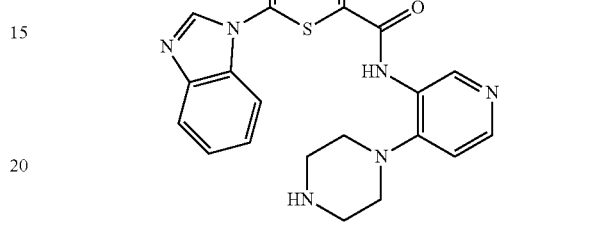
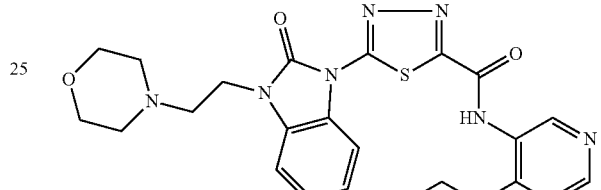
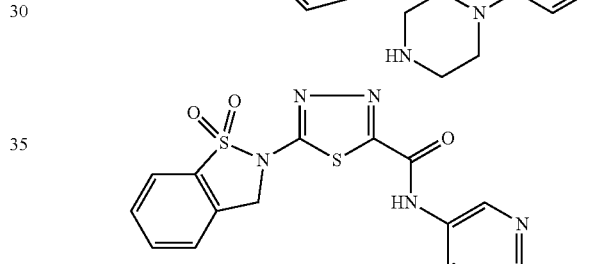
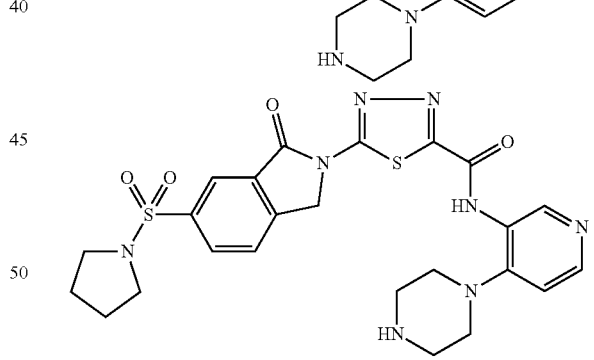
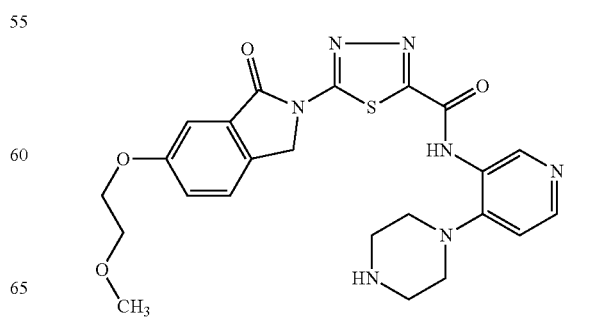

119
-continued
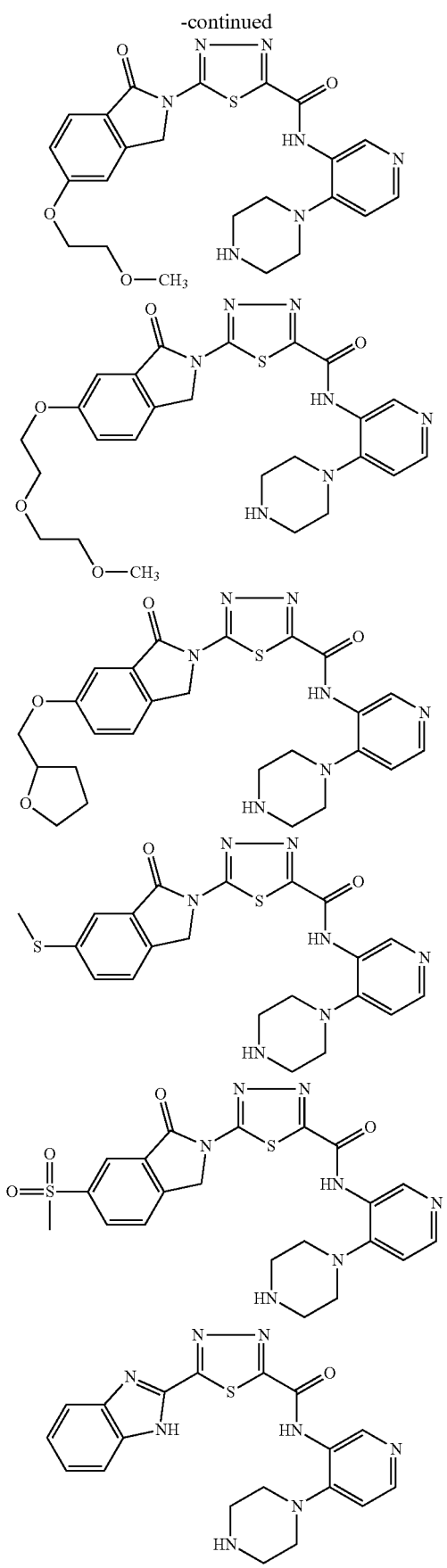
120
-continued
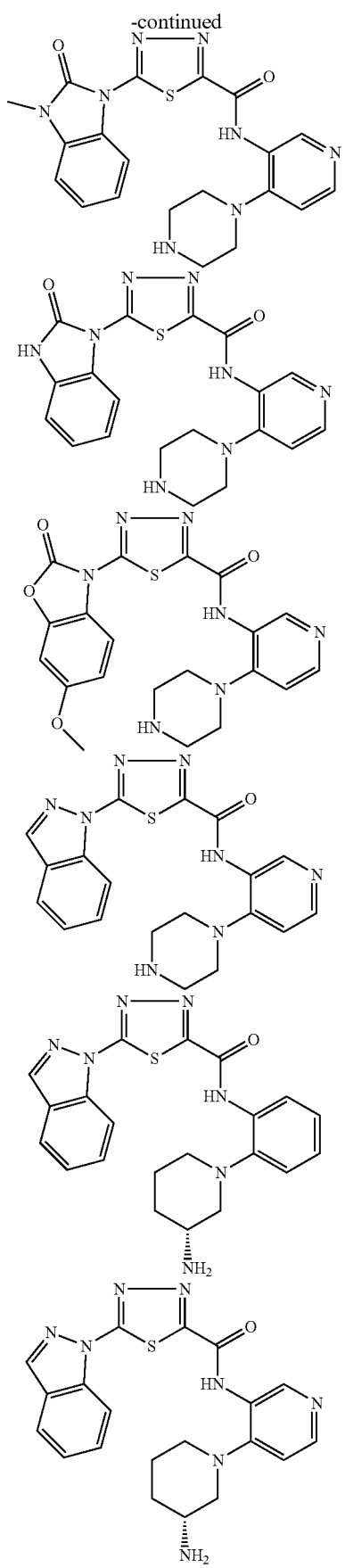

121
-continued
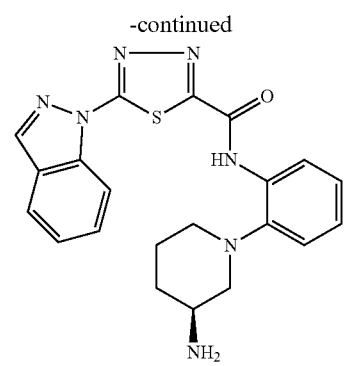
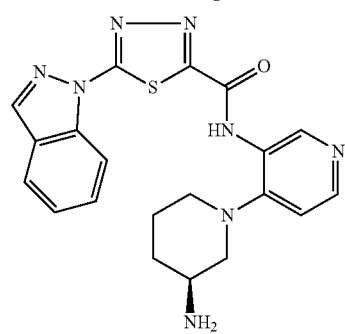
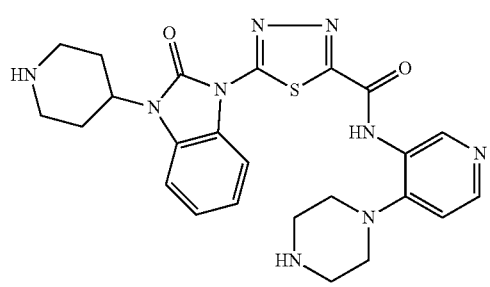
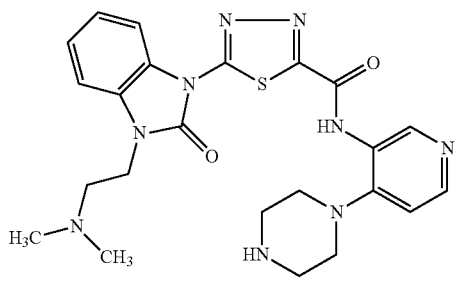
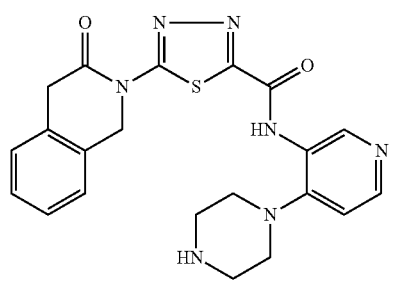
122
-continued
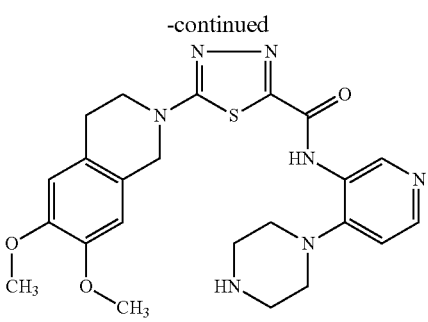
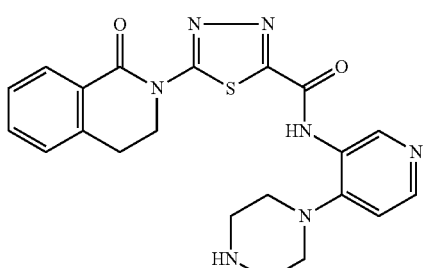
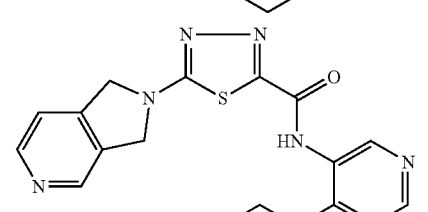
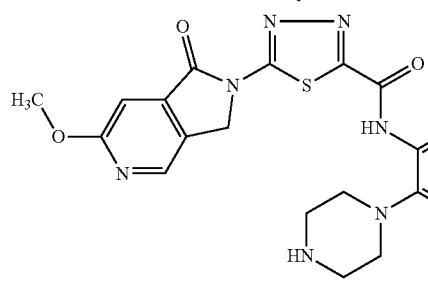
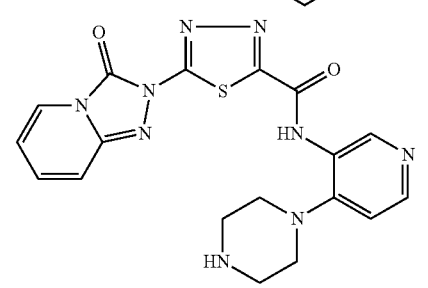
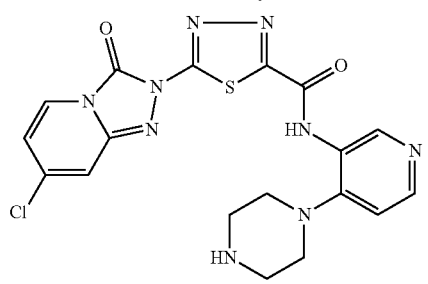

123
-continued
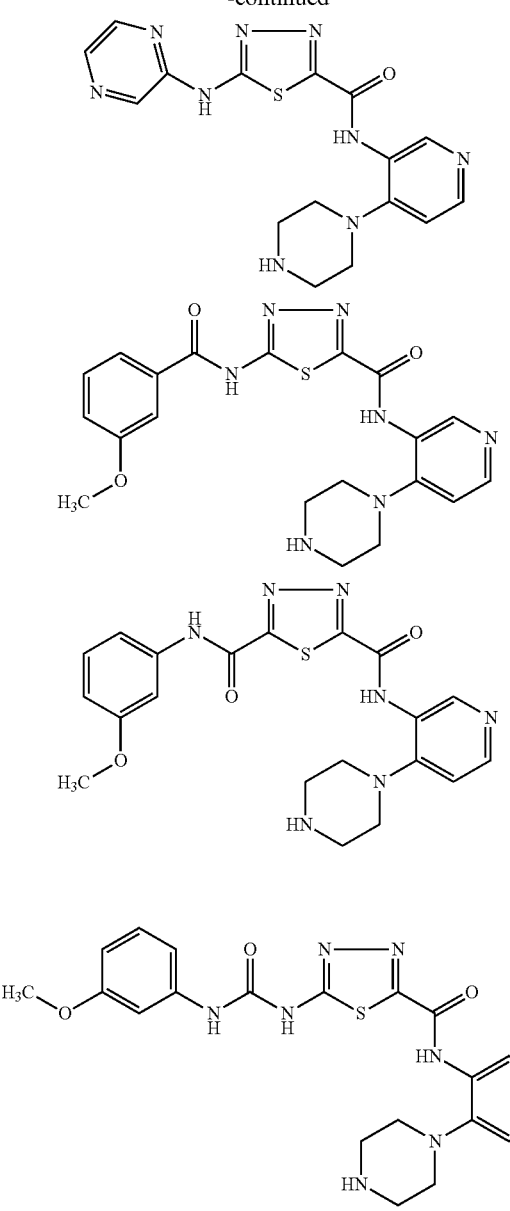
or a pharmaceutically acceptable salt, solvate, ester or prodrug thereof.
In another embodiment of the present invention is a heterocyclic amide derivative selected from the group consisting of:
124
-continued
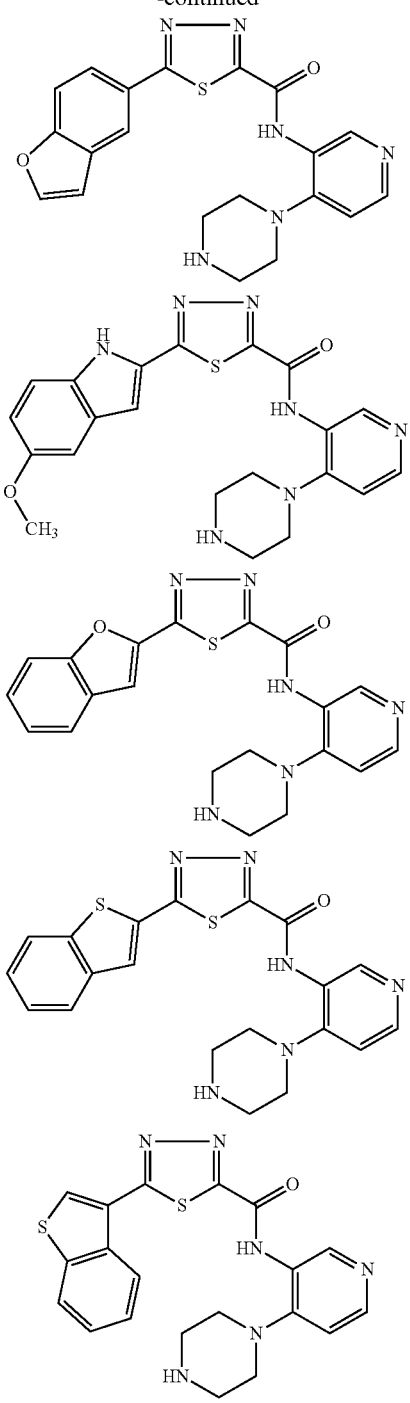
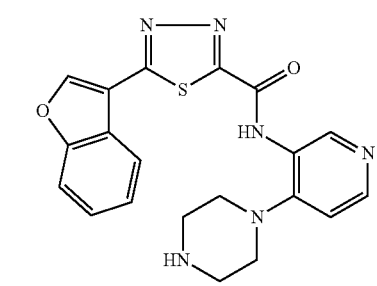

-continued
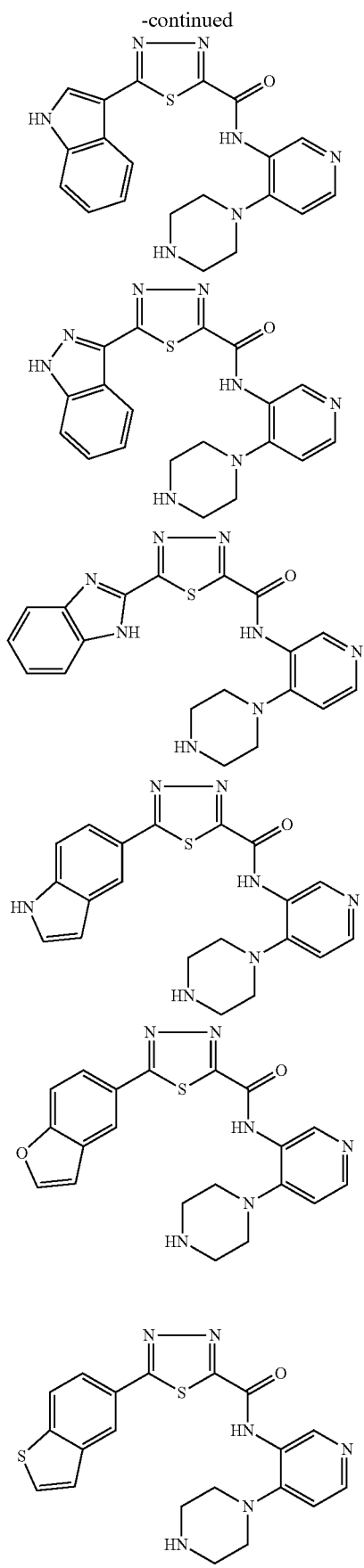
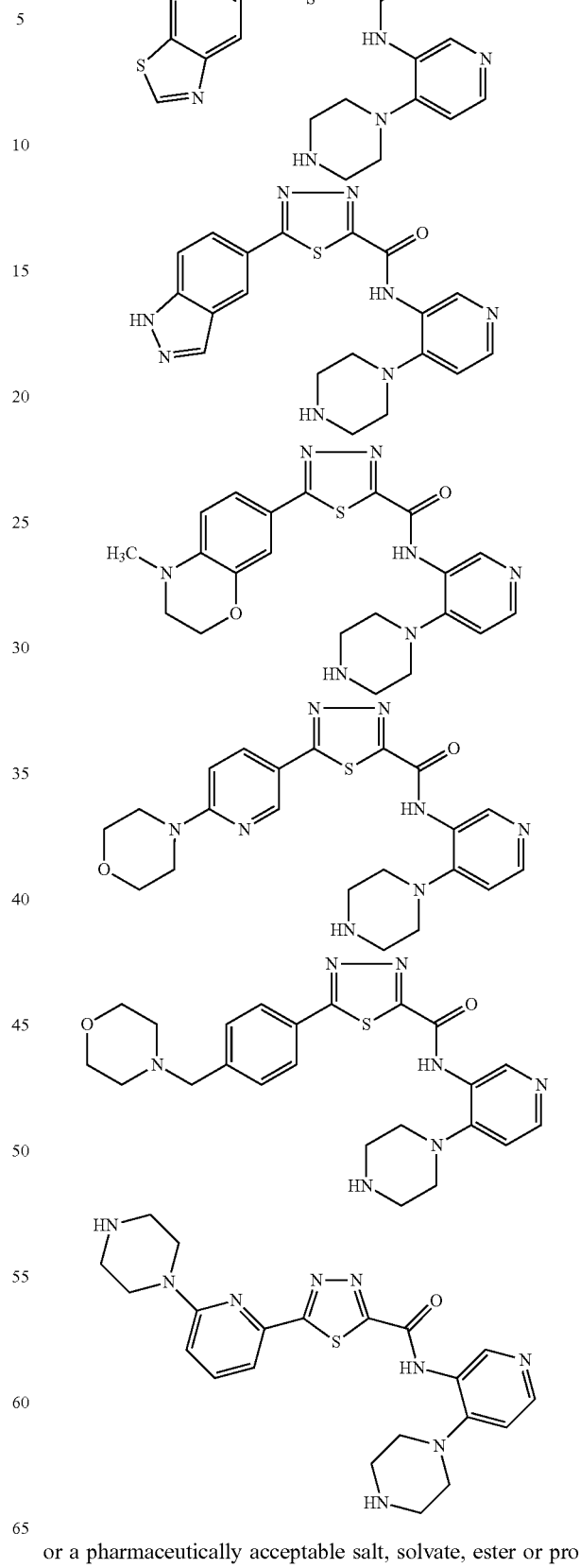
or a pharmaceutically acceptable salt, solvate, ester or prodrug thereof.

In another embodiment of the present invention is a heterocyclic amide derivative selected from the group consisting of:
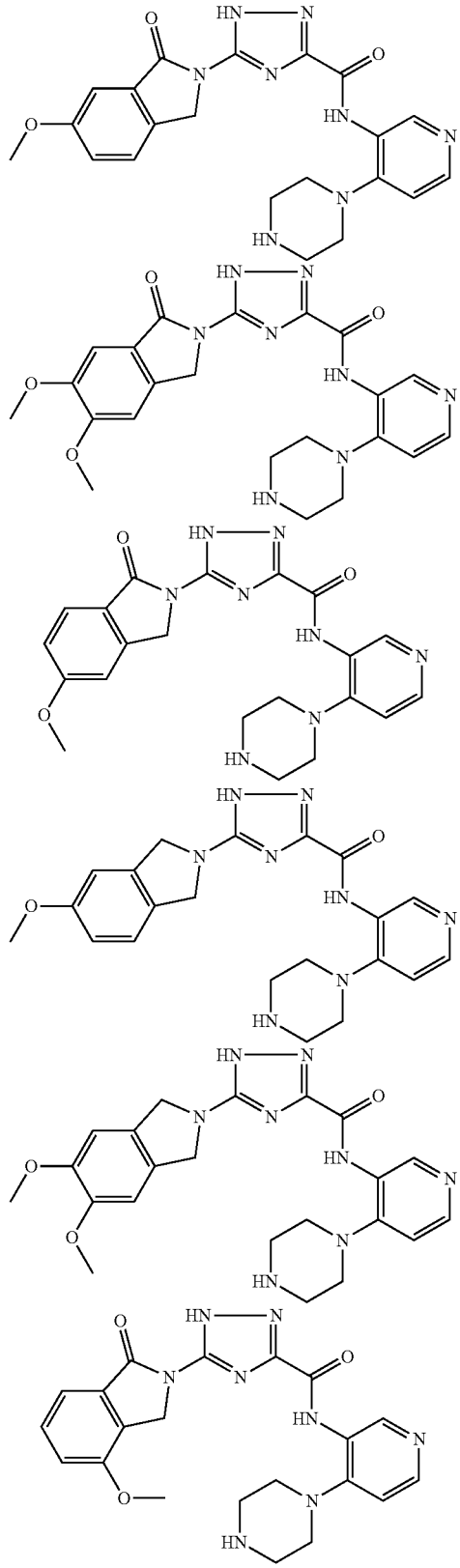
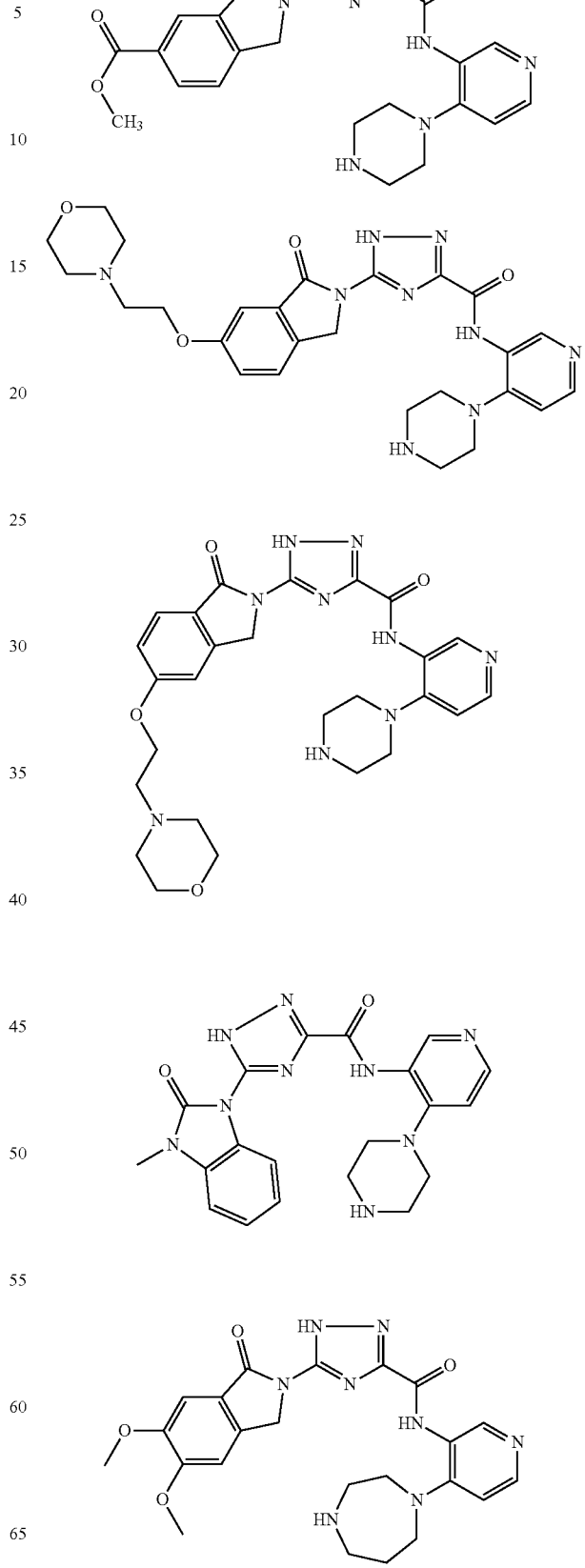

-continued
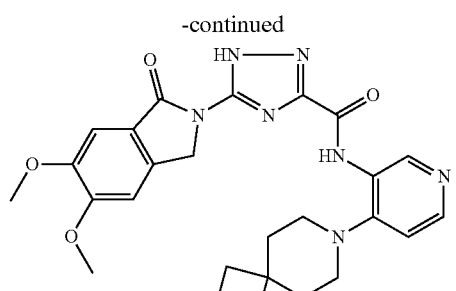
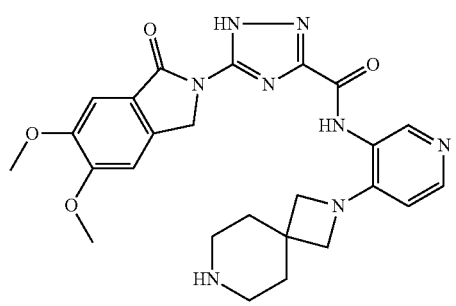
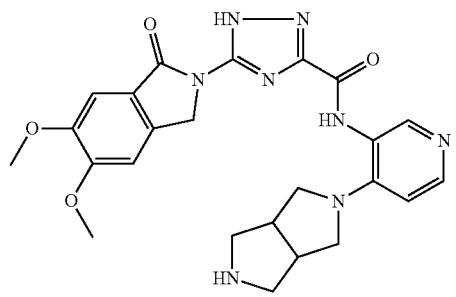
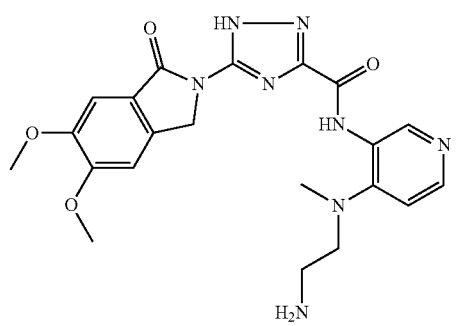
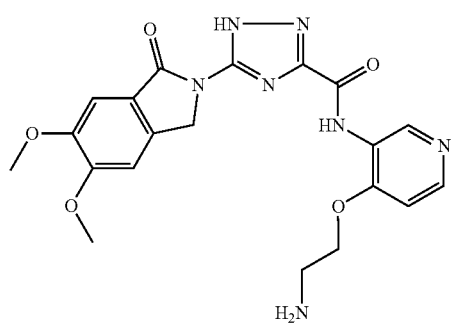
-continued
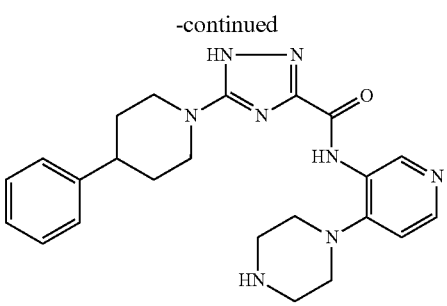
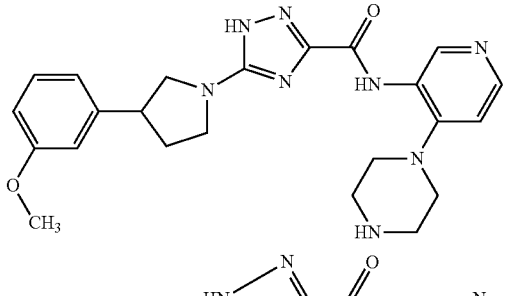
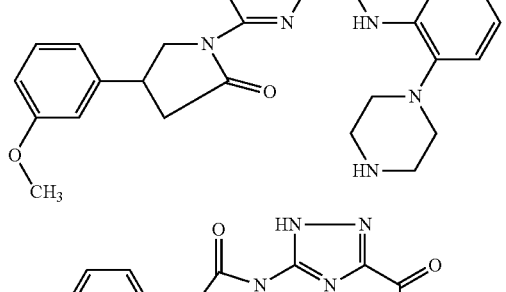
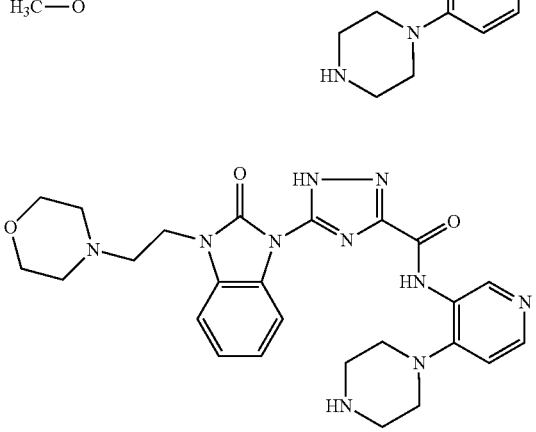
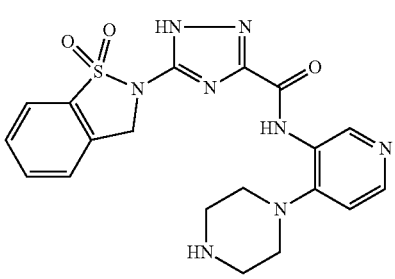

131
-continued
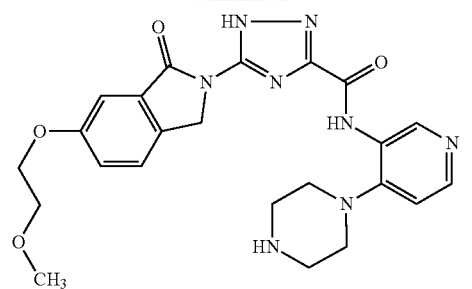
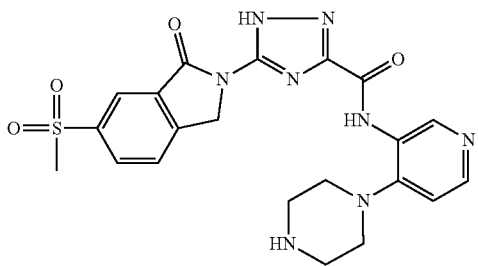
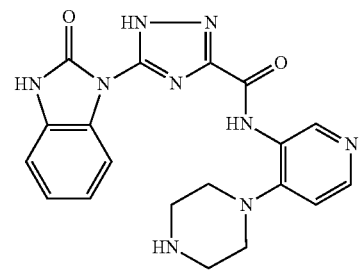
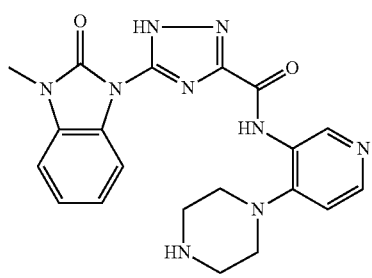
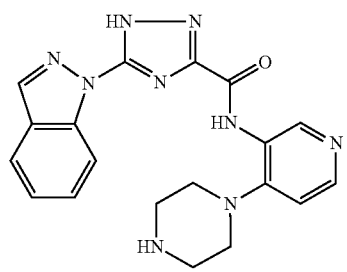
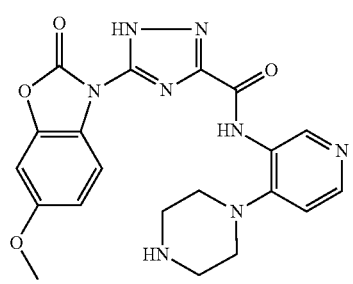
132
-continued
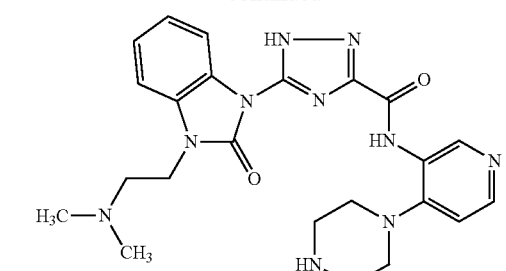
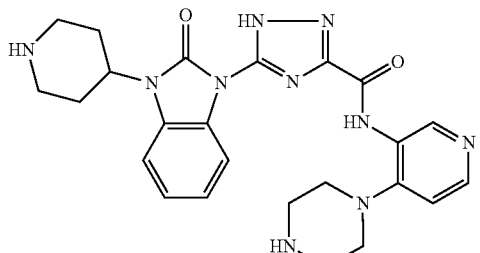
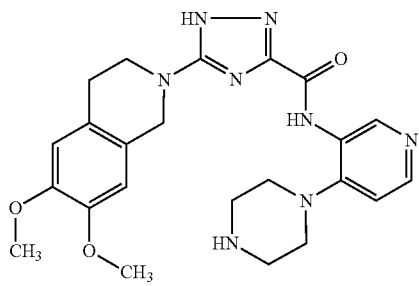
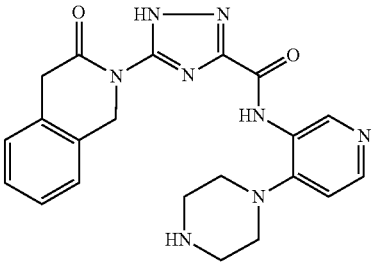
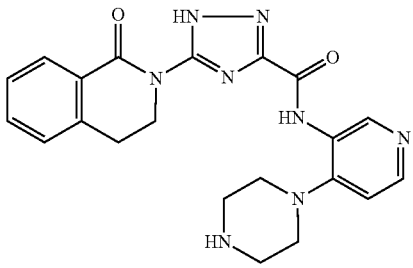
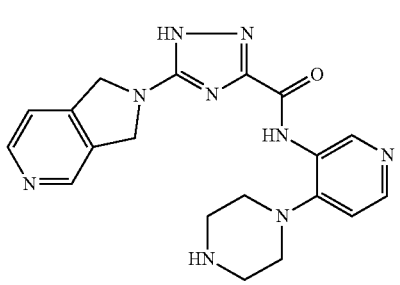

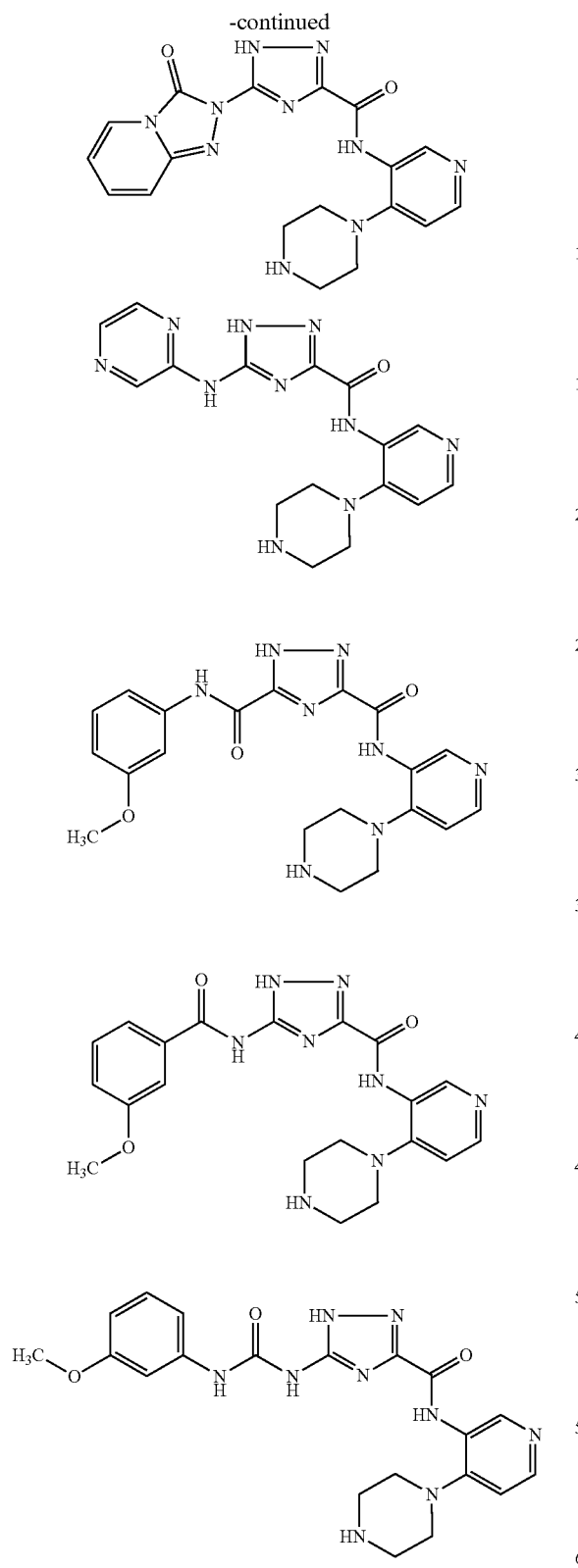
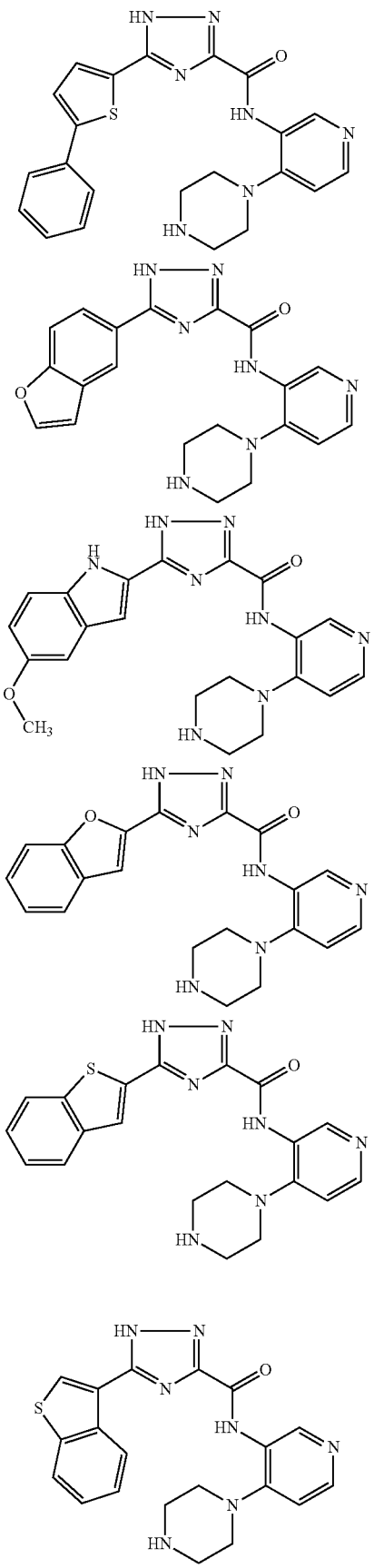
or a pharmaceutically acceptable salt, solvate, ester or prodrug thereof.
In another embodiment of the present invention is a heterocyclic amide derivative selected from the group consisting of:

-continued
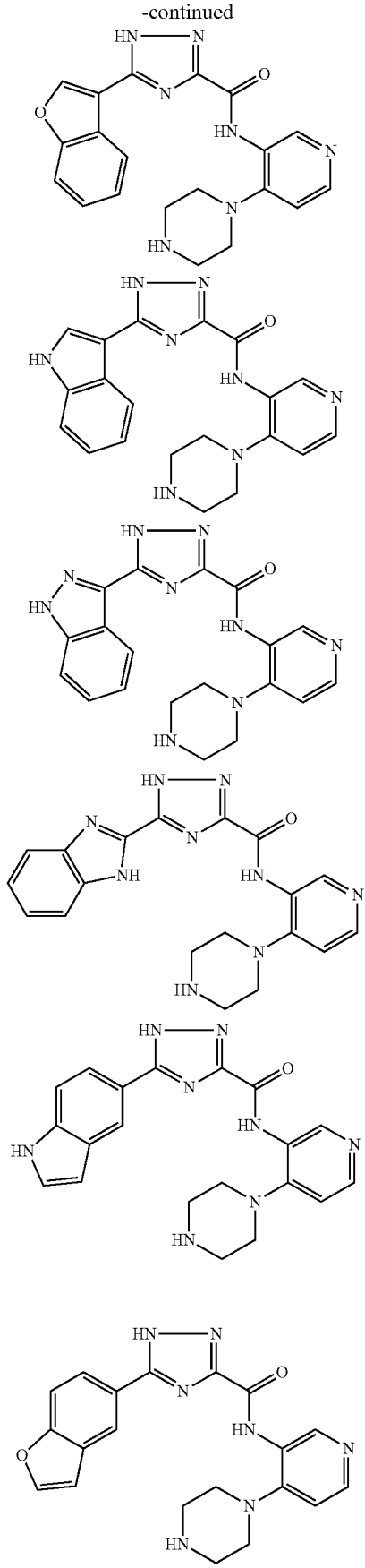
-continued
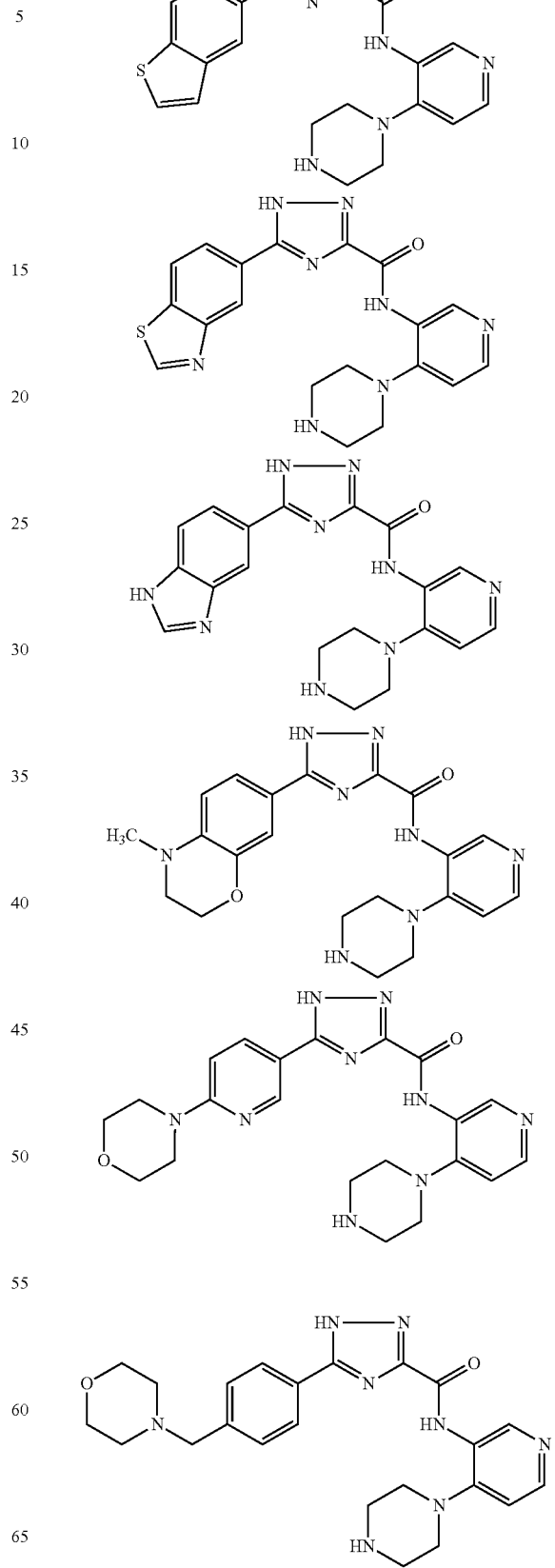

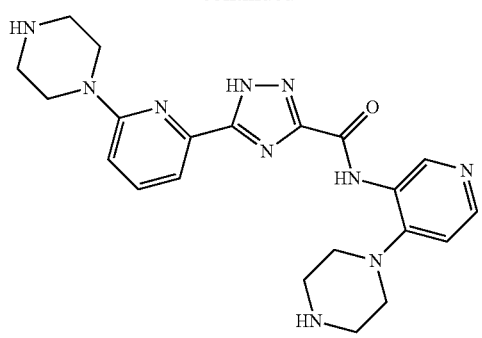
or a pharmaceutically acceptable salt, solvate, ester or prodrug thereof.
In another embodiment of the present invention is a heterocyclic amide derivative selected from the group consisting of:
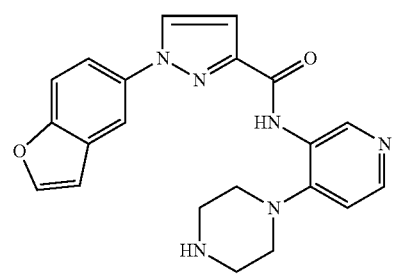
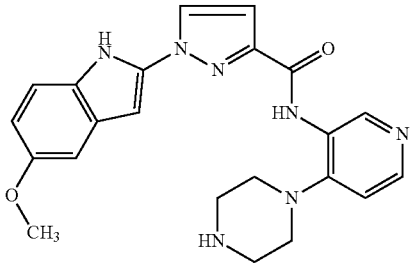
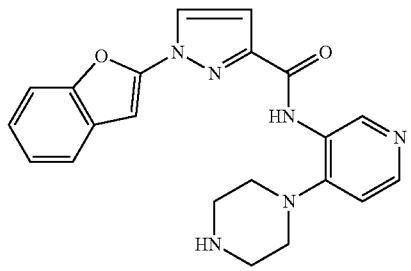
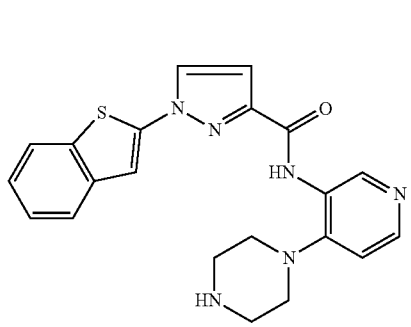
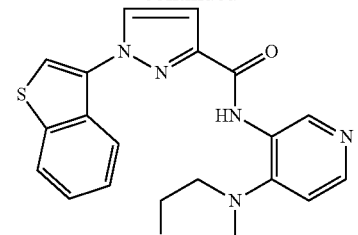
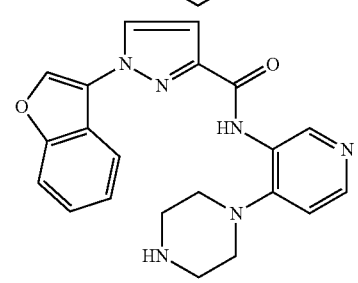
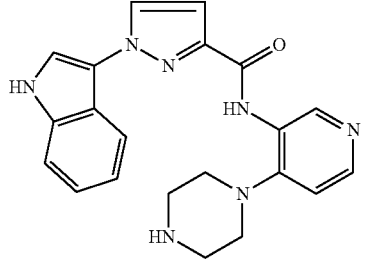
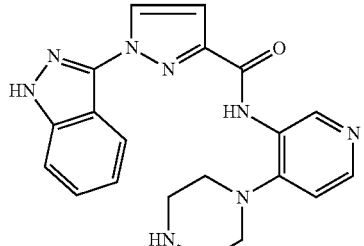
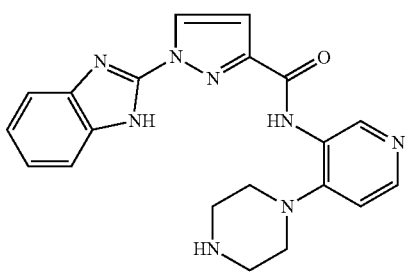
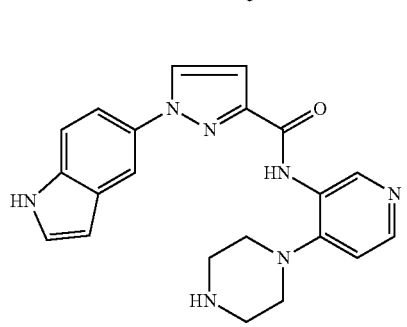

-continued

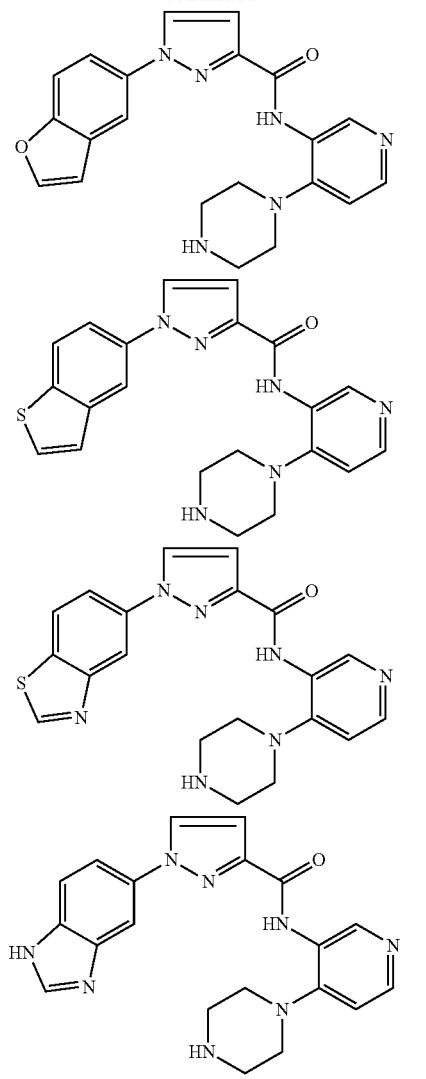

-continued

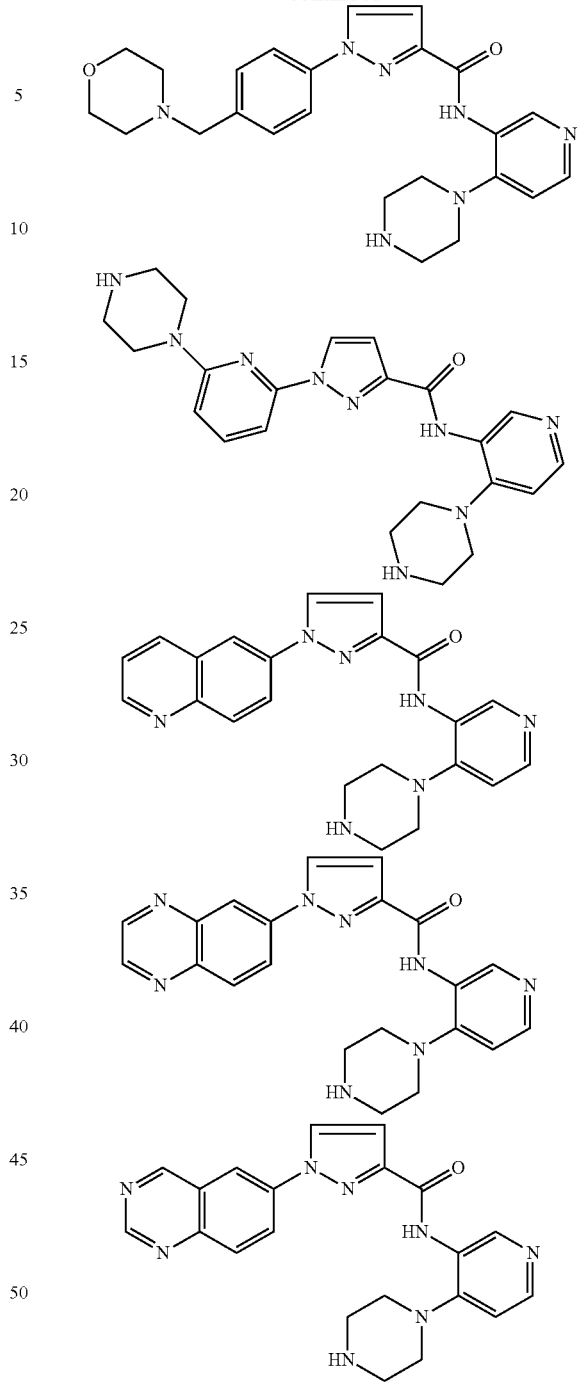

or a pharmaceutically acceptable salt, solvate, ester or prodrug thereof.

Preparation of Heterocyclic Amide Derivatives of the Invention

The heterocyclic amide derivatives of Formula (I) are prepared by methods well known in the art of organic chemistry, see for example, J. March, '*Advanced Organic Chemistry*' 4th Edition, John Wiley and Sons. Specific synthetic routes are described in the generalized Schemes . . . depicted below. Alternative synthetic pathways and analogous structures will be apparent to those skilled in the art of organic synthesis. During synthetic sequences it may be necessary and/or desir-

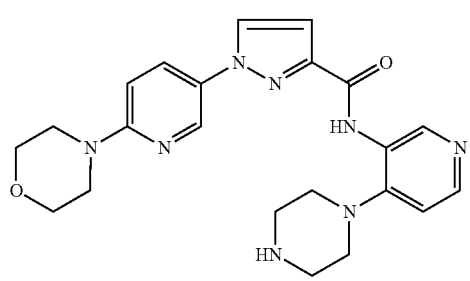

able to protect sensitive or reactive groups on any of the molecules concerned. This is achieved by means of conventional protecting groups, such as those described in T. W. Greene and P. G. M. Wutts 'Protective Groups in Organic Synthesis' 3$^{rd}$ Edition, John Wiley and Sons, 1999. The protective groups are optionally removed at a convenient subsequent stage using methods well known in the art of organic chemistry.

Methods useful for making the heterocyclic amide derivatives of formula (I) are set forth below in Schemes 1-16. Alternative mechanistic pathways and analogous structures will be apparent to those skilled in the art. The methods begin from commercially available starting materials or starting materials which are readily prepared by known processes from commercially available precursors.

Scheme 1 illustrates a method for making the intermediate amine compounds of formula 4.

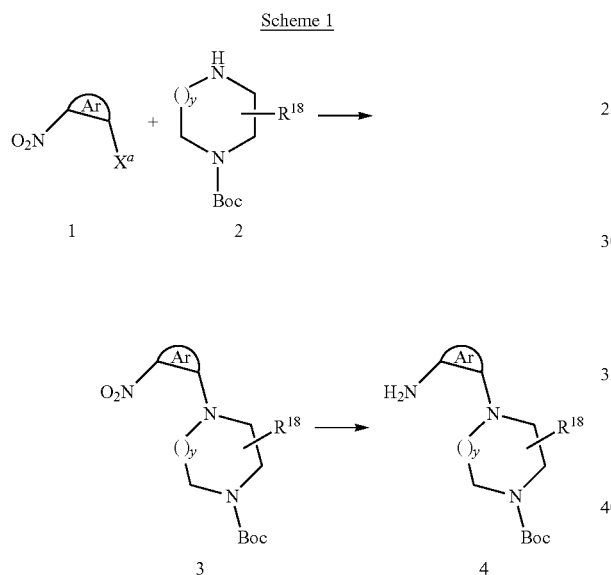

wherein $X^a$ is F or Cl, and $R^{18}$, y and Ar and are as defined above for the compounds of formula (II).

A nitro-substituted aryl or heteroaryl derivative of formula 1 can be coupled with a piperizine compound of formula 2 in the presence of diisopropylethylamine (DIEA) using a microwave-assisted process to provide the coupled compound 3. The nitro group of a compound of formula 3 can then be reduced using an appropriate method to provide the intermediate amine compounds of formula 4.

Scheme 2 illustrates a method for making the intermediate amine compounds of formula 7.

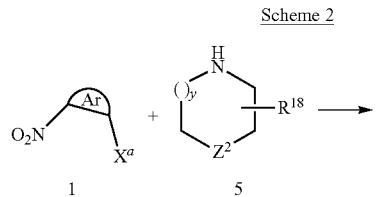

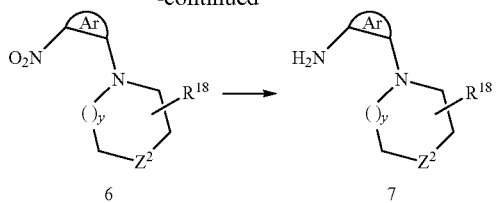

wherein $X^a$ is F or Cl, and $R^{18}$, y, z and Ar are as defined above for the compounds of formula (II).

A nitro-substituted aryl or heteroaryl derivative of formula 1 can be coupled with a cyclic amine of formula 5 to provide the coupled compound 6, using the DIEA coupling method described in Scheme 1. The nitro group of a compound of formula 6 can then be reduced using an appropriate method to provide the intermediate amine compounds of formula 7.

Scheme 3 illustrates a method for making the intermediate amine compounds of formula 10.

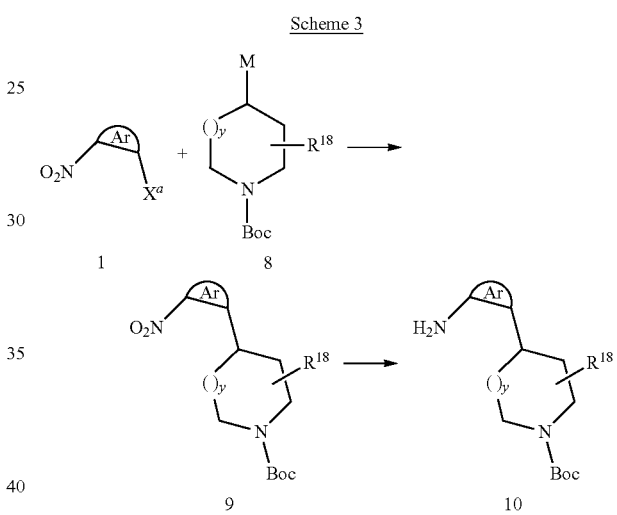

wherein $X^a$ is Cl, Br or —OTf; M is $B(OH)_2$, ZnX or $SnBu_3$; and $R^{18}$, y and Ar are as defined above for the compounds of formula (II).

A nitro-substituted aryl or heteroaryl derivative of formula 1 can be coupled with a piperidine compound of formula 8 using a Pd-catalyzed coupling method (e.g., a Suzuki coupling, a Negishi coupling or a Stille coupling) to provide the coupled compound 9. The nitro group of a compound of formula 9 can then be reduced using an appropriate reduction method to provide the intermediate amine compounds of formula 10.

Scheme 4 illustrates a method for making the intermediate amine compounds of formula 13.

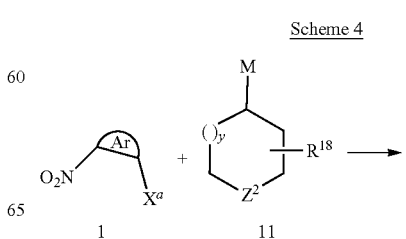

143

-continued

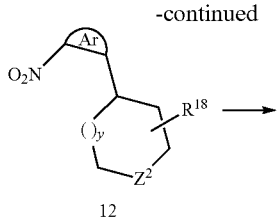

12        13 wherein $X^a$ is —Cl, —Br or —OTf; M is B(OH)$_2$, ZnX or SnBu$_3$; and $R^{18}$, $Z^2$, y and Ar are as defined above for the compounds of formula (II).

A nitro-substituted aryl or heteroaryl derivative of formula 1 can be coupled with a compound of formula 11 to provide a compound of formula 12, using the Pd coupling method described in Scheme 3. The nitro group of a compound of formula 12 can then be reduced using an appropriate method to provide the intermediate amine compounds of formula 13.

Scheme 5 illustrates a method for making the Anilinopiperazine Derivatives of formula (II), wherein $Z^1$ is N and $Z^2$ is NH.

Scheme 5

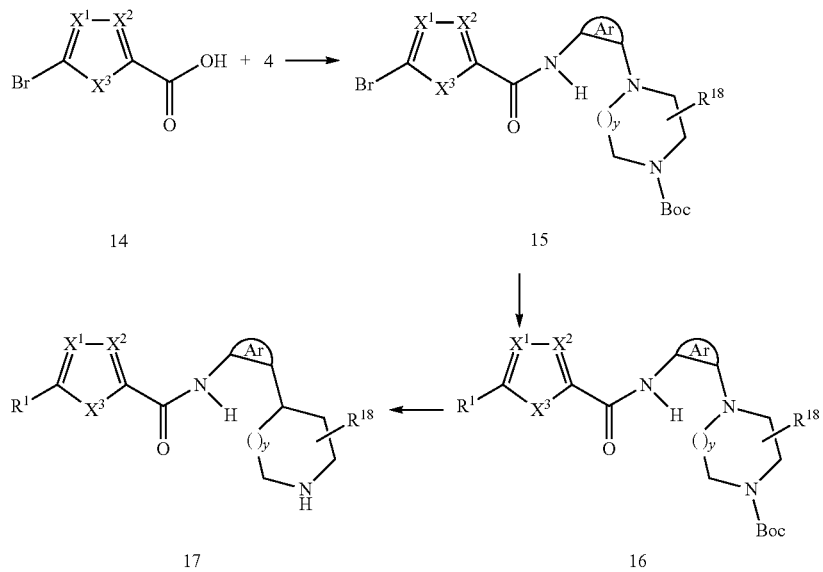

wherein $X^1$, $X^2$, $X^3$, $R^{18}$, y and Ar are as defined above for the compounds of formula (II) and $R^1$ a nitrogenous heterocycle, $Z^1$ is N, and $Z^2$ is NH.

A 2-bromo-azole-4-carboxylic acid compound of formula 14 can be coupled with an amine compound of formula 4 using 2-(1H-7-azabenzotriazol-1-yl)-1,1,3,3-tetramethyl uronium hexafluorophosphate (HATU) in the presence of N,N-diisopropylethylamine (DIPEA) to provide the amido intermediates of formula 15. A compound of formula 15 can then be coupled with a nitrogenous heterocycle $R^1$H (using a palladium-catalyzed process using, for example, tris(dibenzylideneacetone)dipalladium(0) (Pd$_2$(dba)$_3$) and xantphos in the presence of potassium phosphate in toluene at 100° C. to provide the compounds of formula 16. Removal of the Boc protecting group from a compound of formula 16 using an acid, such as TFA or formic acid, provides the Anilinopiperazine Derivative 17.

144

Scheme 6 illustrates a method for making the Anilinopiperazine Derivatives of formula (II), wherein $Z^1$ is N and Scheme 6

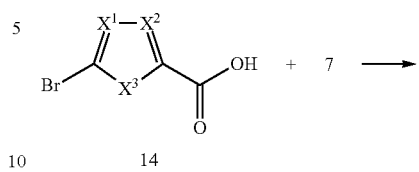

14

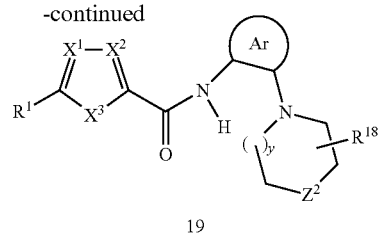

18

↓

-continued

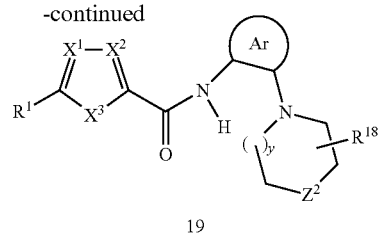

19 wherein $X^1$, $X^2$, $X^3$, $R^{18}$, y Ar and $Z^2$ are as defined above for the compounds of formula (II).

A 2-bromo-thiazole-4-carboxylic acid compound of formula 14 can be coupled with an amine intermediate of formula 7 using the HATU coupling method set forth in Scheme 5 to provide the amido intermediates of formula 18. A compound of formula 18 can then be coupled with a nitrogenous heterocycle $R^1$H using the Pd coupling method set forth in Scheme 5 to provide the Anilinopiperazine Derivatives of formula 19.

Scheme 7 illustrates a method for making the heterocyclic amide derivatives of formula (II), wherein $Z^1$ is —CH— and $Z^2$ is $NR^{18a}$, wherein $R^{18a}$ is as previously defined.

Scheme 7

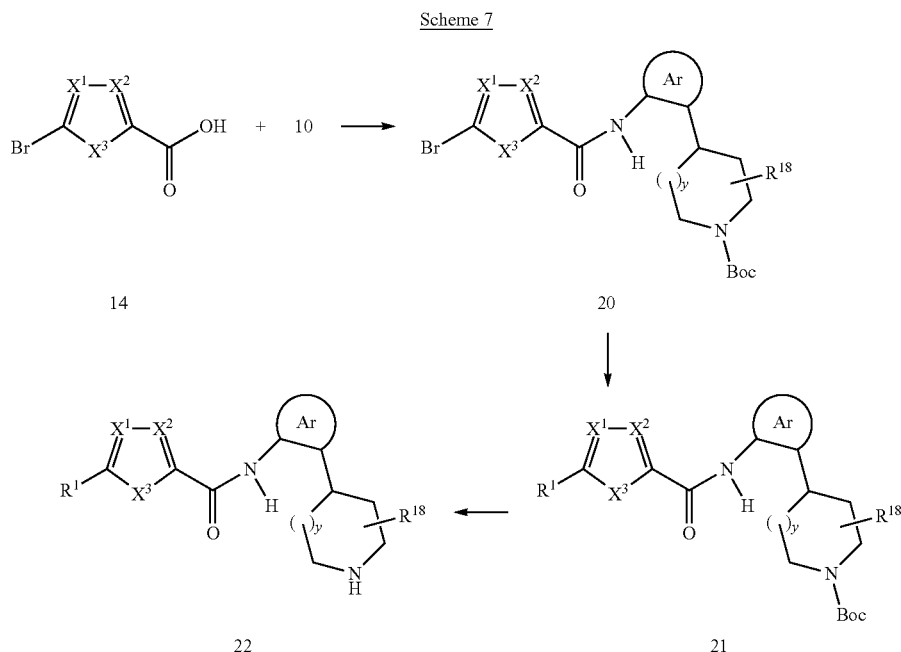

wherein $X^1$, $X^2$, $X^3$, $R^{18}$, y and Ar are as defined above for the compounds of formula (II).

Using the method described in Scheme 5 and substituting intermediate amine compound 10 for intermediate amine compound 4, the piperidine Derivative 22 can be prepared.

Scheme 8 illustrates a method for making the heterocyclic amide derivatives of formula (II), wherein $Z^1$ is CH Scheme 8

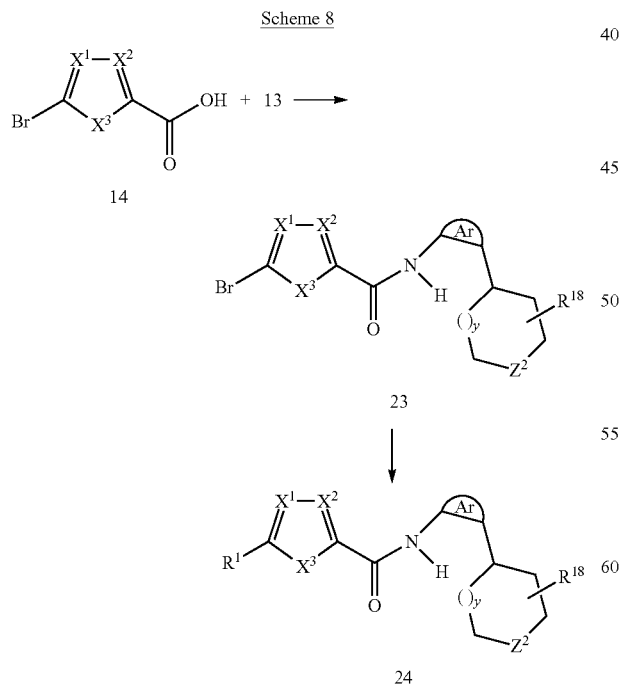

and wherein $R^1$, $X^1$, X2, $X^3$, $R^{18}$, y, $Z^2$ and Ar are as defined above for the compounds of formula (II).

Using the method described in Scheme 6 and substituting intermediate amine compound 13 for intermediate amine compound 7, the heterocyclic amide derivatives of formula 24 can be prepared.

Scheme 9 illustrates an alternative method for coupling the nitrogenous heterocycle $R^1H$ with a compound of formula 25

Scheme 9

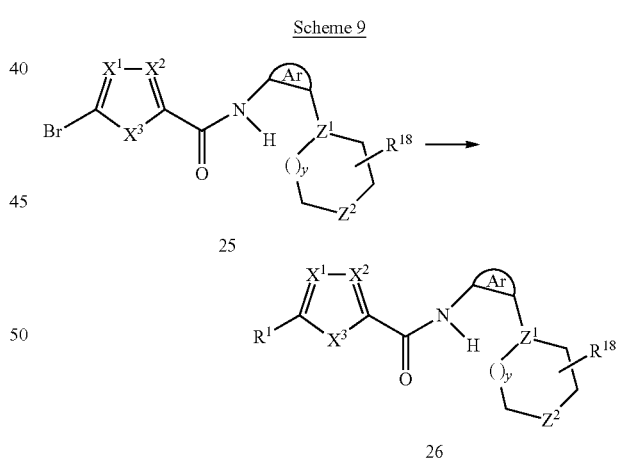

wherein $R^1$, $X^1$, X2, $X^3$, $R^{18}$, y, $Z^1$, $Z^2$ and Ar are as defined above for the compounds of formula (II).

An amido compound of formula 25 can be coupled with an amine $R^1H$ in the presence of diisopropylethylamine using a microwave-assisted process to provide the amine compounds of formula 26.

Scheme 10 describes an alternative method of building up nitrogenous heterocyclic $R^1$ forming part of an intermediate 28, which can then be elaborated by further reaction with intermediates 4, 7, 10 and 13, using, for example aqueous lithium hydroxide followed by coupling the free acid formed with the amine 4, 7, 10, or 13 using standard conditions (HATU/DIEA) to yield the product 29.

Scheme 10

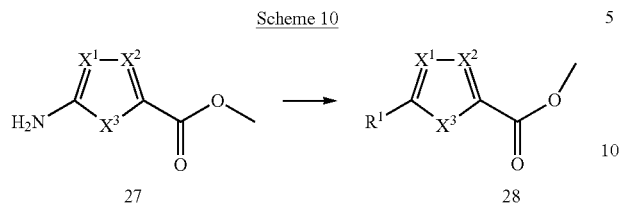

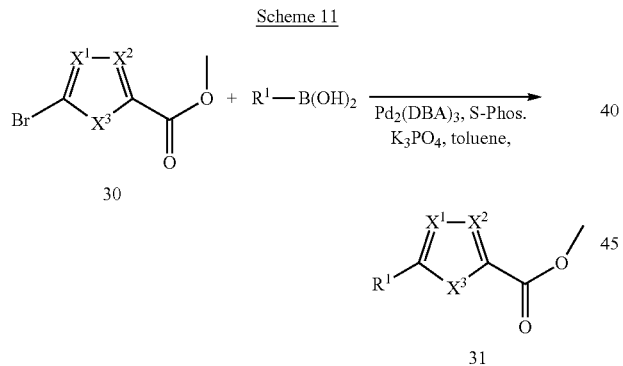

Scheme 11 illustrates coupling methods useful for forming the substituent $R^1$ in 2-substituted-azole-5-carboxylic acid compounds, which are useful intermediates for making the heterocyclic amide derivatives of formula (II). The acids are obtained by hydrolysis of the ester intermediates 31 shown using, for example, lithium hydroxide in THF/water followed by acidification using, for example, HCl.

Scheme 11

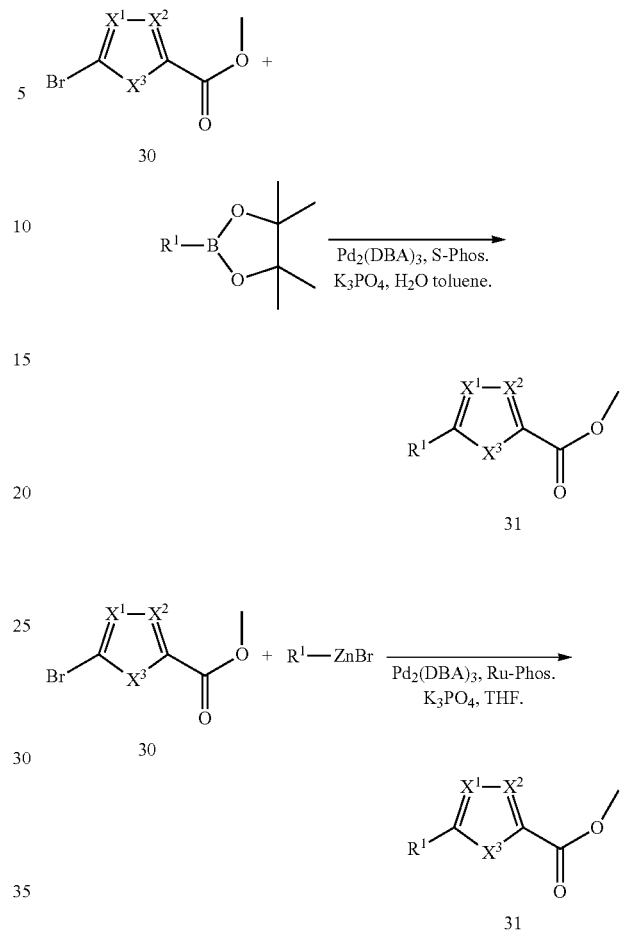

wherein $R^1$ is as defined above for the compounds of formula (I).

2-bromo-carboxylic acid ethyl ester (30) can be reacted with (i) a boronic acid compound, (ii) a boronic pinacol ester compound or (iii) a zinc bromide compound using appropriate palladium coupling conditions to make the 2-substituted ester intermediate of formula 31.

Scheme 12 illustrates a method for making the Anilinopiperazine Derivatives of formula (II), wherein $Z^1$ is —N— and $Z^2$ is NH.

Scheme 12

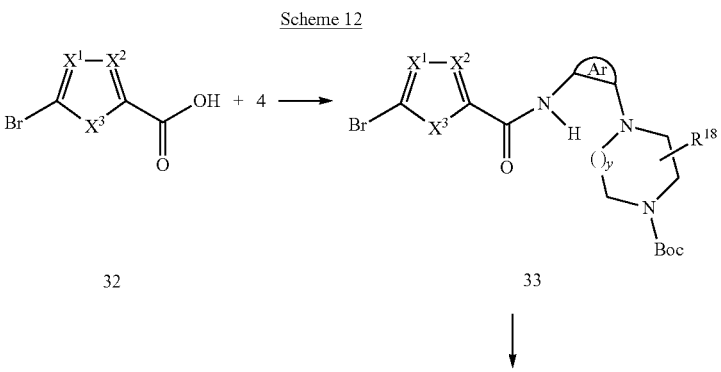

-continued

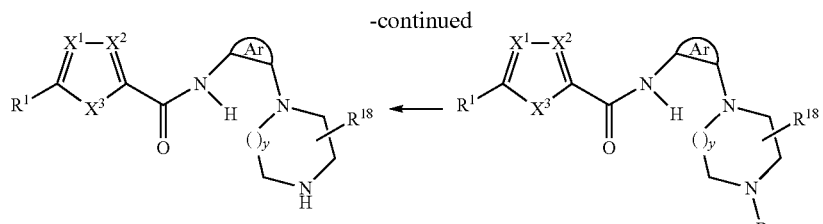

35    34 and wherein $R^1$, $X^1$, $X^2$, $X^3$, Ar, y and $R^{18}$ are as defined above for the compounds of formula (II).

A 2-bromo-carboxylic acid compound of formula 32 can be coupled with an amine compound of formula 4 using 2-(1H-7-azabenzotriazol-1-yl)-1,1,3,3-tetramethyl uronium hexafluorophosphate (HATU) in the presence of N,N-diisopropylethylamine to provide the amido intermediates of formula 33. A compound of formula 33 can then be coupled with an $R^1$ group using a palladium-catalyzed process described in Scheme 6 to provide the compounds of formula 34. Removal of the Boc protecting group from a compound of formula 34 using an acid, such as TFA or formic acid, provides the Anilinopiperazine Derivative 35.

Scheme 13 illustrates a method for making the Anilinopiperazine Derivatives of formula (II), wherein $Z^1$ is N and $Z^2$ is $CR^{18a}$.

Scheme 13

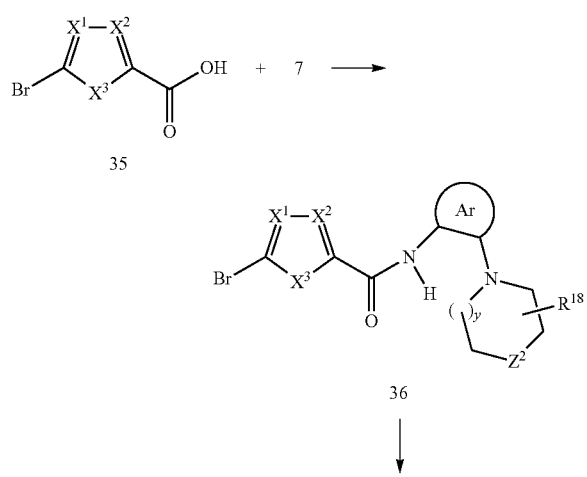

-continued

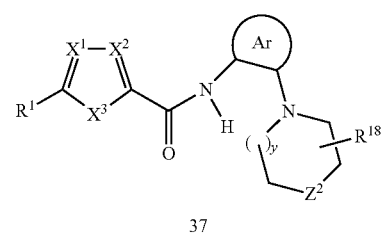

37 and wherein $R^1$, $X^1$, $X^2$, $X^3$, Ar, y, $Z^2$ and $R^{18}$ are as defined above for the compounds of formula (II).

A 2-bromo-carboxylic acid compound of formula 35 can be coupled with an amine intermediate of formula 7 using the HATU coupling method set forth in Scheme 10 to provide the amido intermediates of formula 36. A compound of formula 36 can then be coupled with an $R^1$ group using a palladium-catalyzed process described in Scheme 11 to provide the Anilinopiperazine Derivatives of formula 37.

Scheme 14 illustrates a method for making heterocyclic amide derivatives of formula (II), wherein $Z^1$ is CH and $Z^2$ is $NR^{18a}$, wherein $R^{18a}$ is as previously defined.

Scheme 14

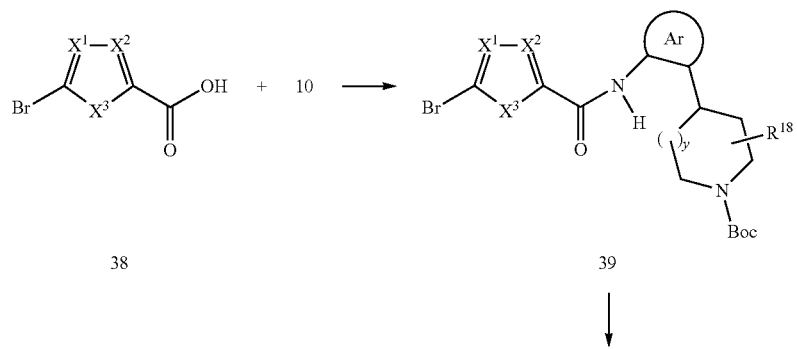

38    39

-continued

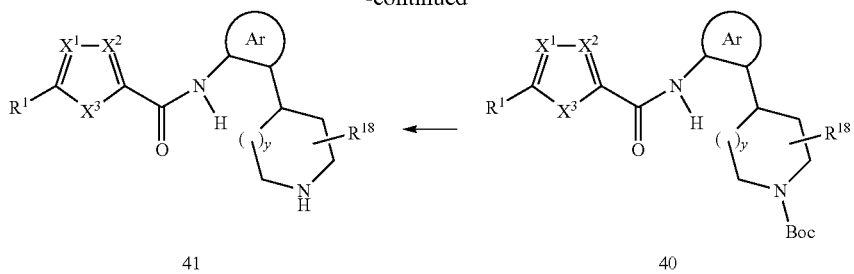

41        40 wherein $R^1$, $X^1$, $X^2$, $X^3$, Ar, y and $R^{18}$ are as defined above for the compounds of formula (II).

Using the method described in Scheme 12 and substituting intermediate amine compound 10, the piperidine Derivative of formula 41 can be prepared via intermediates 39 and 40.

Scheme 15 illustrates a method for making the heterocyclic amide derivatives of formula (II), wherein $Z^1$ is CH and $Z^2$ is —$CR^{18a}$.

Scheme 15

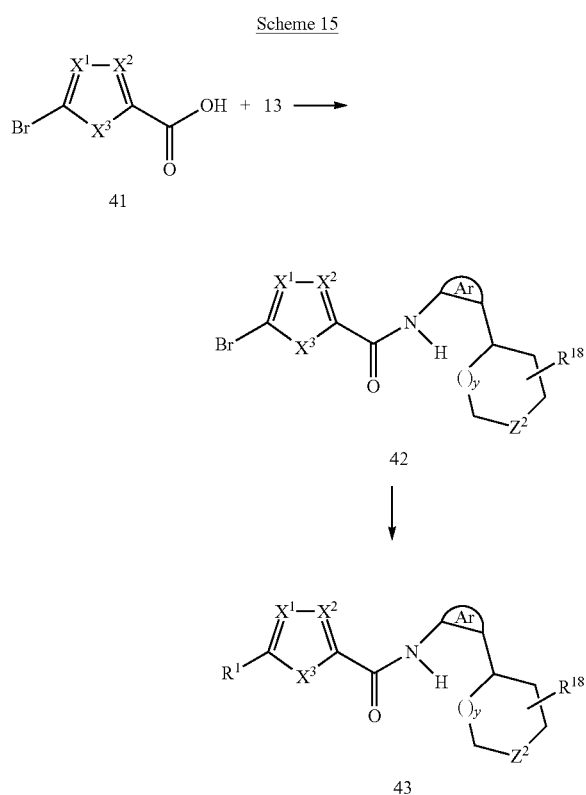

wherein $R^1$, $X^1$, $X^2$, $X^3$, Ar, y, $Z^2$ and $R^{18}$ are as defined above for the compounds of formula (II).

Using the method described in Scheme 13 and substituting intermediate amine compound 13 for intermediate amine compound 7, the piperidine Derivative 43 can be prepared via intermediate 42.

Scheme 16 illustrates an alternative method for making the heterocyclic amide derivatives of formula (II) comprising coupling an amine compound of formula 4, 7, 10 or 13 with a 2-substituted-heterocyclic-5-carboxylic acid of formula 44.

Scheme-16

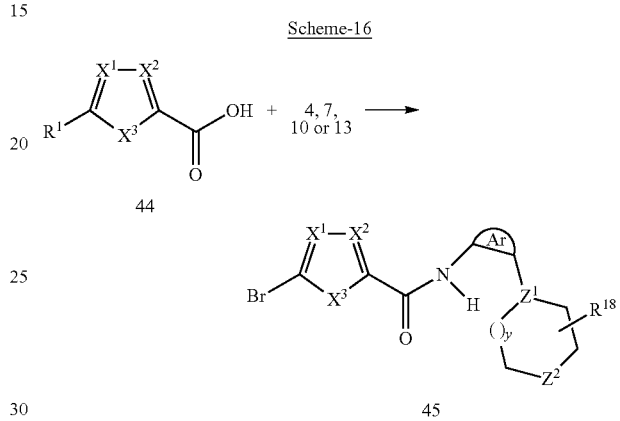

wherein $R^1$, $X^1$, $X^2$, $X^3$, Ar, $Z^1$, $Z^2$, y, and $R^{18}$ are as defined above for the compounds of formula (II).

A 2-substituted-heterocyclic-5 carboxylic acid of formula 44 can be coupled with an amine compound of formula 4, 7, 10 or 13 using the HATU-mediated coupling method set forth in Scheme 5 to provide the desired heterocyclic amide derivative 45.

Uses of Heterocyclic Amide Derivatives of the Invention

The compounds of the present invention can be useful for treating or preventing a proliferative disease, such as cancer; an autoimmune disease; a viral disease; a fungal disease; a neurological or neurodegenerative disorder (e.g., Alzheimer's disease or Parkinson's disease); arthritis; inflammation; an ischemic injury; an anti-proliferative disorder (e.g., ocular retinopathy); a neuronal disease; alopecia; or a cardiovascular disease. Specific diseases and disorders treatable by administration of at least one compound of present invention include, but are not limited to, those disclosed in U.S. Pat. No. 6,413,974, which is incorporated by reference herein.

The compounds of the present invention have pharmacological properties. In one embodiment, the present compounds (i.e. those of Formula I-VI) can be inhibitors, regulators or modulators of protein kinases. Accordingly, the present compounds are useful for treating or preventing diseases and disorders related to the activity of one or more protein kinases. Non-limiting examples of protein kinases that can be inhibited, regulated or modulated by the compounds of the present invention include cyclin-dependent kinases (CDKs) such as CDK1, CDK2, CDK3, CDK4, CDK5, CDK6 and CDK7, CDK8; aurora kinases such as Aurora-A, Aurora-B and Aurora-C; mitogen activated protein kinase (MAPK/ERK); glycogen synthase kinase 3 (GSK3beta); c-Met kinases, such as c-Met; Pim-1 kinases; checkpoint kinases, such as Chk1 and Chk2; tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)); non-receptor protein tyrosine kinases, for example LCK, Src, Frk, Btk, Csk, Abl, Zap70, Fes/Fps, Fak, Jak, Ack, and LIMK; and growth factor receptor tyrosine kinases such as VEGF-R2, FGF-R, TEK, Akt kinases and the like.

The present compounds can be useful for inhibiting oncogenes that encode for protein kinases. Non-limiting examples of such oncogenes include C-Met.

The present compounds can be useful for treating or preventing a proliferative disease. Illustrative examples of proliferative diseases that can be treated or prevented according to the present methods include, but are not limited to, cancer, atherosclerosis, arthritis, psoriasis, idiopathic pulmonary fibrosis, scleroderma and cirrhosis of the liver.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The present compounds may also be useful in the treatment of Alzheimer's disease, as suggested by the recent finding that CDK5 is involved in the phosphorylation of tau protein (*J. Biochem*, (1995) 117, 741-749).

The present compounds may induce or inhibit apoptosis. The apoptotic response is aberrant in a variety of human diseases. The present compounds, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The present compounds, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

The present compounds may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl, m-Tor, PDK and ERK, and thus be effective in the treatment of diseases associated with other protein kinases.

Accordingly, one aspect of this invention is a method for treating a disease or disorder in a patient, wherein the disease or disorder is associated with one or more protein kinases, the method comprising administering to the patient a therapeutically effective amount of at least one compound of the present invention, or a pharmaceutically acceptable salt, solvate, ester or prodrug thereof.

In a specific embodiment, the compounds of the present invention can be useful in the treatment or prevention of a variety of cancers and metastases thereof, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including brain tumors such as an astrocytoma, a neuroblastoma, a glioma (such as glioblastoma multiforme) or a schwannoma; and other tumors, including melanoma, seminoma, teratocarcinoma, osteosarcoma, xenoderoma pigmentosum, keratoctanthoma, thyroid follicular cancer and Kaposi's sarcoma. The present compounds are useful for treating primary and/or metastatic tumors.

The present compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The present compounds may also be useful in inhibiting tumor angiogenesis and metastasis.

The compounds of this invention may also be useful in combination (administered together or sequentially in any order) with one or more separate anticancer treatments such as radiation therapy, and/or at least one anticancer agent different from the present compounds. The compounds of the present invention can be present in the same dosage unit as the anticancer agent or in separate dosage units.

Another aspect of the present invention is a method of treating one or more diseases associated with a cyclin dependent kinase, comprising administering to a patient in need of such treatment an amount of a first compound, which is a compound of Formula I-VI, or a pharmaceutically acceptable salt, solvate, ester, prodrug or stereoisomer thereof; and an amount of at least one second compound, the second compound being an anticancer agent different from the present compounds, wherein the amounts of the first compound and the second compound result in a therapeutic effect.

Non-limiting examples of additional anticancer agents (also known as anti-neoplastic agents) suitable for use in combination with the compounds of the present invention include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR® from Merck & Company, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Merck & Company, Kenilworth, N.J.), tipifarnib (Zarnestre or R115777 or tipifarnib from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® or gefitinib from Astra Zeneca Pharmaceuticals, England), Tarceva® (EGFR kinase inhibitors, erlotinib), antibodies to EGFR (e.g., C225), GLEEVEC® (C-abl kinase inhibitor from Novartis Pharmaceuticals, East Hanover, N.J.; imatinib); interferons such as, for example, intron (from Merck & Company), Peg-Intron (from Merck & Company); hormonal therapy combinations; aromatase combinations; ara-C, adriamycin, cytoxan, and gemcitabine.

Other useful additional anticancer agents include but are not limited to Uracil mustard, Chlormethine, Ifosfamide, Melphalan, Chlorambucil, Pipobroman, Triethylenemelamine, ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other useful additional anticancer agents include but are not limited to Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN® from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Oxaliplatin, Aroplatin, Hydroxyurea, Amsacrine, Procarbazine, Mitotane, Mitoxantrone, Levamisole, Navelbene, Anastrazole, tetrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 (cetuximab) and Campath.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. The compounds of the present invention may also be administered sequentially with known anticancer or cytotoxic agents when a combination formulation is inappropriate. The invention is not limited in the sequence of administration; the present compounds may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in one aspect, this invention includes methods for treating cancer in a patient, comprising administering to the patient an amount of at least one compound of the present invention, or a pharmaceutically acceptable salt, solvate, ester, prodrug or stereoisomer thereof, and one or more other anticancer treatment modalities, wherein the amounts of the present compound(s)/other treatment modality result in the desired therapeutic effect. In one embodiment, the at least one compound of the present invention and the one or more other treatment modalities act synergistically. In one embodiment, the at least one compound of the present invention and the one or more other treatment modalities act additively.

In one embodiment, the other treatment modality is surgery.

In another embodiment, the other treatment modality is radiation therapy.

In another embodiment, the other treatment modality is biological therapy, such as hormonal therapy or anticancer vaccine therapy.

In another embodiment, the present invention provides a method of inhibiting one or more Checkpoint kinases in a patient in need thereof, comprising administering to the patient a therapeutically effective amount of at least one compound of the present invention or a pharmaceutically acceptable salt, solvate, ester, prodrug or stereoisomer thereof.

Another aspect of the present invention is a method of treating, or slowing the progression of, a disease associated with one or more Checkpoint kinases in a patient in need thereof, comprising administering a therapeutically effective amount of at least one compound of the present invention or a pharmaceutically acceptable salt, solvate, ester, prodrug or stereoisomer thereof.

Yet another aspect of the present invention is a method of treating one or more diseases associated with Checkpoint kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one compound of the present invention, or a pharmaceutically acceptable salt, solvate, ester, prodrug or stereoisomer thereof.

In the above methods, the checkpoint kinase to be inhibited can be Chk1 and/or Chk2.

Another aspect of the present invention is a method of inhibiting one or more tyrosine kinases in a patient in need thereof, comprising administering to the patient a therapeutically effective amount of at least one compound of the present invention or a pharmaceutically acceptable salt, solvate, ester, prodrug or stereoisomer thereof.

Yet another aspect of the present invention is a method of treating, or slowing the progression of, a disease associated with one or more tyrosine kinases in a patient in need thereof, comprising administering a therapeutically effective amount of at least one compound of the present invention or a pharmaceutically acceptable salt, solvate, ester, prodrug or stereoisomer thereof.

Another aspect of the present invention is a method of treating one or more diseases associated with tyrosine kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one one compound of the present invention and the at least one anticancer agent result in a therapeutic effect.

Another aspect of the present invention is a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

In the above methods, the tyrosine kinase can be VEGFR (VEGF-R2), EGFR, HER2, SRC, JAK and/or TEK.

Another aspect of the present invention is a method of inhibiting one or more Pim-1 kinases in a patient in need thereof, comprising administering to the patient a therapeutically effective amount of at least one compound of the present invention or a pharmaceutically acceptable salt, solvate, ester, prodrug or stereoisomer thereof.

Yet another aspect of the present invention is a method of treating, or slowing the progression of, a disease associated with one or more Pim-1 kinases in a patient in need thereof, comprising administering a therapeutically effective amount of at least one compound of the present invention or a pharmaceutically acceptable salt, solvate, ester, prodrug or stereoisomer thereof.

Another aspect of the present invention is a method of treating one or more diseases associated with Pim-1 kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Pim-1 kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

Another aspect of the present invention is a method of treating one or more diseases associated with an Aurora kinase, comprising administering to a patient in need of such treatment at least one compound of the present invention, or a pharmaceutically acceptable salt, solvate, ester, prodrug or stereoisomer thereof; and at least one additional anticancer agent, wherein the amounts of the at least one compound of the present invention and the at least one anticancer agent result in a therapeutic effect.

Another aspect of the present invention is a method of treating, or slowing the progression of, a disease associated with one or more Aurora kinases in a patient in need thereof, comprising administering a therapeutically effective amount of a pharmaceutical composition comprising in combination at least one pharmaceutically acceptable carrier and at least one compound of the present invention or a pharmaceutically acceptable salt, solvate, ester, prodrug or stereoisomer thereof.

The pharmacological properties of the compounds of this invention may be confirmed by a number of pharmacological assays. The exemplified pharmacological assays which are described herein below have been carried out with compounds according to the invention and their salts, solvates, esters or prodrugs.

Compositions of Heterocyclic Amide Derivatives of the Invention

This invention is also directed to pharmaceutical compositions which comprise at least one compound of the present invention, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt, solvate, ester or prodrug of said compound and a pharmaceutically acceptable carrier, vehicle or diluent.

In another aspect the present invention provides a kit comprising an amount of at least one compound of the present invention, or a pharmaceutically acceptable salt, solvate, ester or prodrug of said compound and an amount of at least one anticancer therapy and/or additional anticancer agent listed above, wherein the amounts of the two or more ingredients result in desired therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

Experimental Methods

The present invention is further illustrated by the following examples which are not intended to limit the scope thereof. Unless otherwise indicated, temperature is in ° C. or is at ambient temperature, and pressure is at or near atmospheric. Commercial reagents and solvents were used without further purification.

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from Me$_4$Si with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech platinum C18, 3 micron, 33 mm×7 mm 1D; gradient flow: 0 min—10% CH$_3$CN, 5 min—95% CH$_3$CN, 7 min—95% CH$_3$CN, 7.5 min—10% CH$_3$CN, 9 min—stop. MS data were obtained using Agilent Technologies LC/MSD SL or 1100 series LC/MSD mass spectrometer. Final compounds were purified by PrepLC using the column of Varian Pursuit XRs C18 10 u 250×21.2 mm and an eluent mixture of mobile phase A and B. The mobile phase A is composed of 0.1% TFA in H$_2$O and the mobile phase B is composed of CH$_3$CN (95%)/H$_2$O (5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 u150×4.6 mm column and an eluent mixture of mobile phase A and B, wherein mobile phase A is composed of 0.1% TFA in H$_2$O and the mobile phase B is composed of CH$_3$CN (95%)/H$_2$O (5%)/TFA (0.1%). The column was eluted at a flow rate of 3 mL/min at a temperature of 60° C. Intermediate compounds were characterized by LCMS using a Higgins Haisil HL C18 5u 50×4.6 mm column and an eluent mixture of mobile phase A and B, wherein mobile phase A is composed of 0.1% TFA in H$_2$O and the mobile phase B is composed of CH$_3$CN (95%)/H$_2$O (5%)/TFA (0.1%). The column was eluted at a flow rate of 3 mL/min at a column temperature of 60° C.

Synthesis of Non-Limiting Examples of the Present Invention

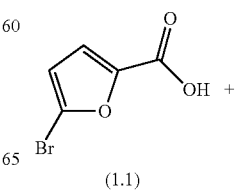

(1.1)

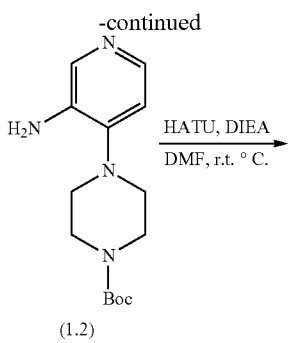

(1.2)

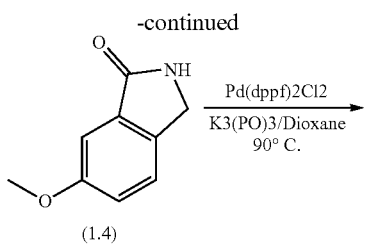

(1.4)

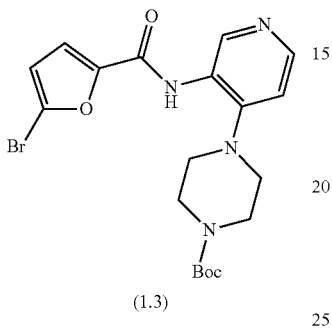

(1.3)

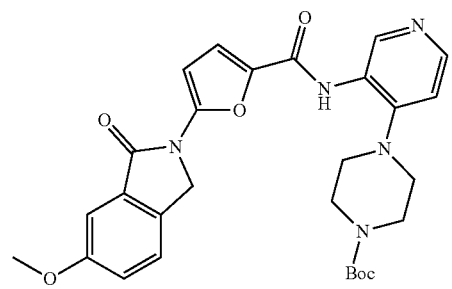

(1.5)

5-Bromo furan-2 carboxylic acid (1.1) is coupled with amine compound, tert-butyl-4-(3-aminopyridin-4-yl-1-carboxylate of formula (1.2) using 2-(1H-7-azabenzotriazol-1-yl)-1,1,3,3-tetramethyl uronium hexafluorophosphate (HATU) in the presence of N,N-disopropylethylamine to provide the amido intermediate, tert-butyl 4-(3-(5-bromofuran-2-carboxamido)pyridin-4-yl)piperazine-1-carboxylate, (1.3) Mass calculated for formula $C_{19}H_{23}BrN_4O_4$, 450.09, observed LCMS m/z 451.31 (M+H)

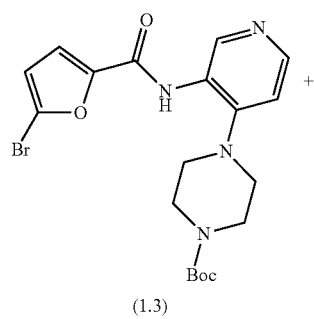

(1.3)

A mixture of tert-butyl 4-(3-(5-bromofuran-2-carboxamido)pyridin-4-yl)piperazine-1-carboxylate (1.3, 100 mg, 0.20 mmol), the 6-methoxy-2,3-dihydro-isoindol-1-one,(1.4, 1.2 equivalent), Tris(dibenzylideneacetone) dipalladium(0) (20 mg, 0.02 mmol), Xantphos (26 mg, 0.04 mmol), Potassium acetate (139 mg, 0.66 mmol) in 5 ml of Dioxane was heated to 85° C. for 16 hours. Resulting suspension was diluted with ethyl acetate and passed through a celite filter to remove insoluble solid. Organic layer was concentrated in vacuo. The crude compound was purified by Prep-LC to yield compound, tert-butyl 4-(3-(5-(6-methoxy-1-oxoisoindolin-2-yl)furan-2-carboxamido)pyridin-4-yl)piperazine-1-carboxylate (1.5). HPLC-MS tR=3.84 min (UV254 nm); Mass calculated for formula $C_{28}H_{31}N_5O_6$, 533.23; observed LCMS m/z 534.20(M+H).

By essentially following the procedure described above for the preparation of intermediate (1.5), the compounds (2.5)-(9.5) of Table 1 below could be prepared.

TABLE 1

| Intermediate | Structure | MWt | M + H | HPLC ret time, min* 5 min run |
|---|---|---|---|---|
| (1.5) | 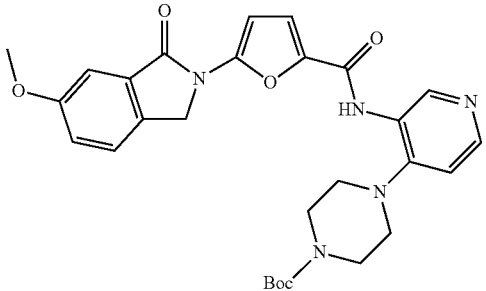 [SMILES: COc1ccc2c(c1)C(=O)N(c1ccc(C(=O)Nc3cnccc3N3CCN(C(=O)OC(C)(C)C)CC3)o1)C2] | 533.23 | 534.20 | 2.51 |

TABLE 1-continued

| Intermediate | Structure | MWt | M + H | HPLC ret time, min* 5 min run |
|---|---|---|---|---|
| (2.5) | 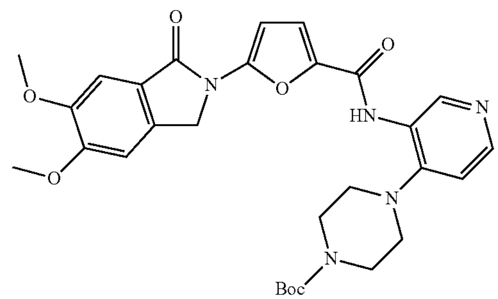 [SMILES: COc1cc2c(cc1OC)C(=O)N(c1ccc(C(=O)Nc3cnccc3N3CCN(C(=O)OC(C)(C)C)CC3)o1)C2] | 563.24 | 564.20 | 1.95 |
| (3.5) | 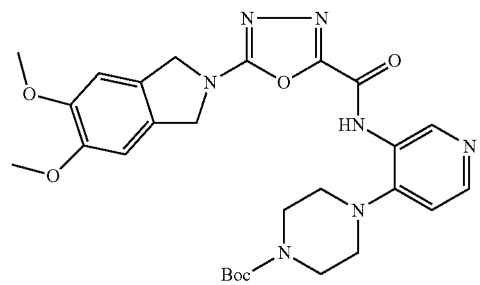 [SMILES: COc1cc2c(cc1OC)CN(c1nnc(C(=O)Nc3cnccc3N3CCN(C(=O)OC(C)(C)C)CC3)o1)C2] | 551.59 | 552.20 | 1.85 |
| (4.5) | 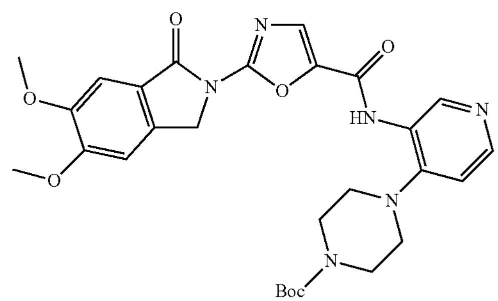 [SMILES: COc1cc2c(cc1OC)C(=O)N(c1ncc(C(=O)Nc3cnccc3N3CCN(C(=O)OC(C)(C)C)CC3)o1)C2] | 564.23 | 565.10 | 2.20 |
| (5.5) | 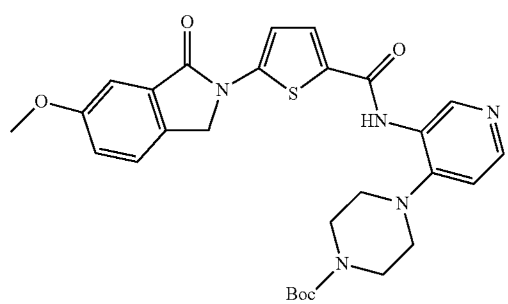 [SMILES: COc1ccc2c(c1)C(=O)N(c1ccc(C(=O)Nc3cnccc3N3CCN(C(=O)OC(C)(C)C)CC3)s1)C2] | 549.20 | 550.10 | 3.20 |
| (6.5) | 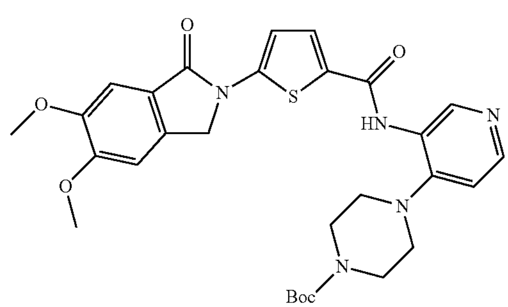 [SMILES: COc1cc2c(cc1OC)C(=O)N(c1ccc(C(=O)Nc3cnccc3N3CCN(C(=O)OC(C)(C)C)CC3)s1)C2] | 579.22 | 580.10 | 3.0 |

TABLE 1-continued
| Intermediate | Structure | MWt | M + H | HPLC ret time, min* 5 min run |
|---|---|---|---|---|
| (7.5) | 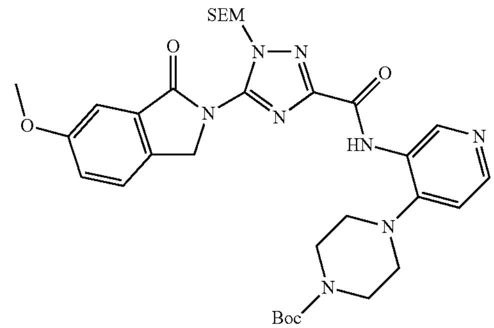 [SMILES: COc1ccc2c(c1)C(=O)N(c1nc(C(=O)Nc3cnccc3N3CCN(C(=O)OC(C)(C)C)CC3)nn1COCC[Si](C)(C)C)C2] | 664.32 | 665.20 | 3.55 |
| (8.5) | 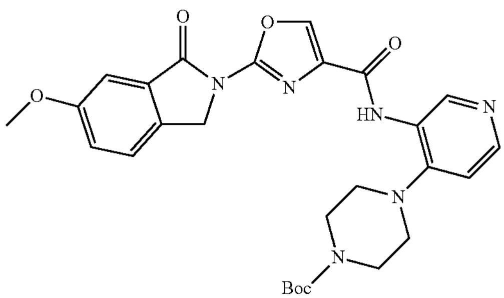 [SMILES: COc1ccc2c(c1)C(=O)N(c1nc(C(=O)Nc3cnccc3N3CCN(C(=O)OC(C)(C)C)CC3)co1)C2] | 534.32 | 535.20 | 2.90 |
| (9.5) | 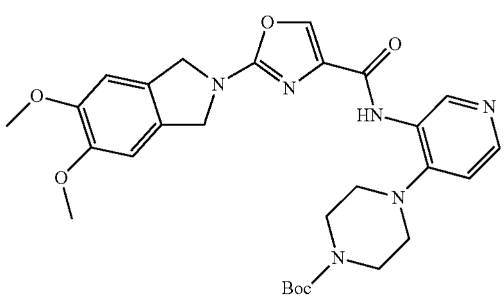 [SMILES: COc1cc2c(cc1OC)CN(c1nc(C(=O)Nc3cnccc3N3CCN(C(=O)OC(C)(C)C)CC3)co1)C2] | 550.25 | 551.20 | 2.75 |
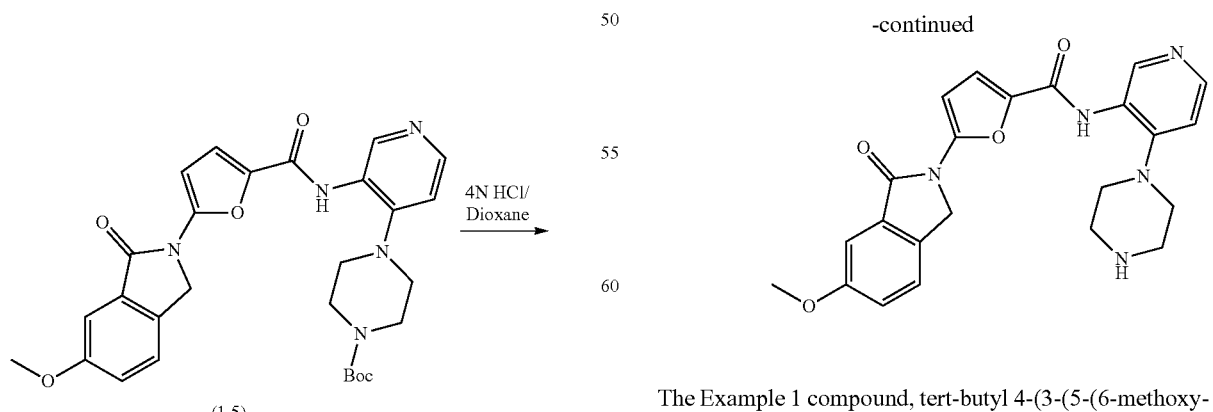
The Example 1 compound, tert-butyl 4-(3-(5-(6-methoxy-1-oxoisoindolin-2-yl)furan-2-carboxamido)pyridin-4-yl)piperazine-1-carboxylate (1.5) (0.1 mmol) was cooled to 0° C. in 1 mL of dioxane and was added to 4N HCl in dioxane (1 mL) and stirred at room temperature for 30 min. Dioxane was removed under vacuo, redissolved in water-acetonitrile and freezed and lyophilized to obtain 5-(6-methoxy-1-oxoisoindolin-2-yl)-N-(4-(piperazin-1-yl)pyridin-3-yl)furan-2-carboxamide (Example 1) as white powder. HPLC-MS tR=0.75 min (UV254 nm); Mass calculated for formula $C_{23}H_{23}N_5O_4$, 433.18, observed LCMS m/z 434.20 (M+H)

By essentially following the procedure described for Intermediate (1.5) to (1.9), Examples 1-9 in Table 2 could be synthesized

TABLE 2

| Example. | Structure | MWt | M + H | HPLC ret time, min, 10 min run |
|---|---|---|---|---|
| 1 | 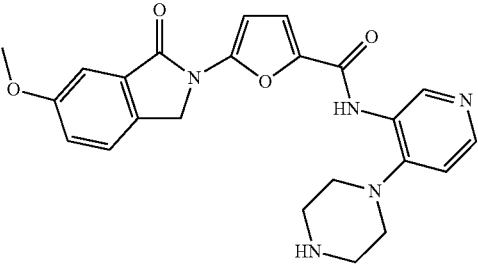 [SMILES: COc1ccc2c(c1)C(=O)N(c1ccc(C(=O)Nc3cnccc3N3CCNCC3)o1)C2] | 433.23 | 434.20 | 2.45 |
| 2 | 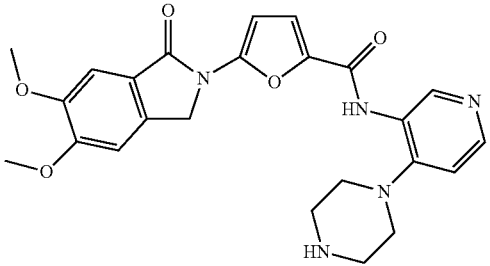 [SMILES: COc1cc2c(cc1OC)C(=O)N(c1ccc(C(=O)Nc3cnccc3N3CCNCC3)o1)C2] | 436.41 | 437.20 | 2.25 |
| 3 | 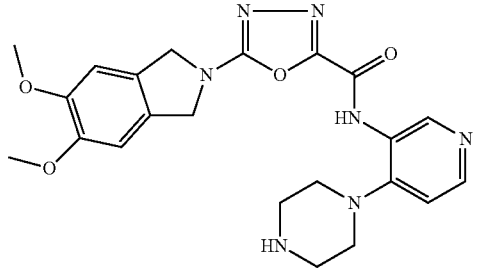 [SMILES: COc1cc2c(cc1OC)CN(c1nnc(C(=O)Nc3cnccc3N3CCNCC3)o1)C2] | 460.86 | 461.20 | 2.75 |
| 4 | 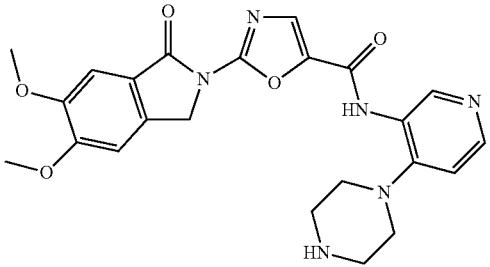 [SMILES: COc1cc2c(cc1OC)C(=O)N(c1ncc(C(=O)Nc3cnccc3N3CCNCC3)o1)C2] | 464.23 | 465.20 | 2.20 |
| 5 | 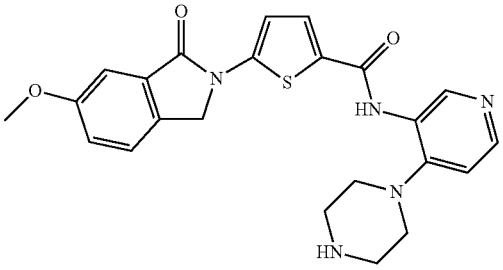 [SMILES: COc1ccc2c(c1)C(=O)N(c1ccc(C(=O)Nc3cnccc3N3CCNCC3)s1)C2] | 422.44 | 423.20 | 3.10 |

TABLE 2-continued

| Example. | Structure | MWt | M + H | HPLC ret time, min, 10 min run |
|---|---|---|---|---|
| 6 | 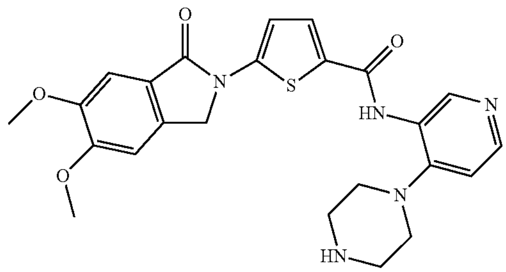 [SMILES: COc1cc2c(cc1OC)C(=O)N(c1ccc(C(=O)Nc3cnccc3N3CCNCC3)s1)C2] | 452.47 | 453.20 | 3.00 |
| 7 | 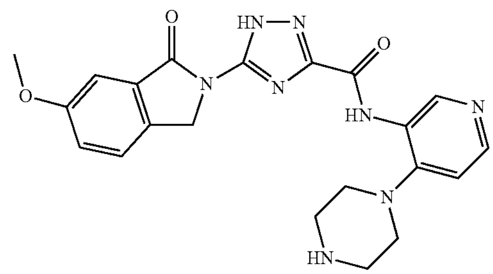 [SMILES: COc1ccc2c(c1)C(=O)N(c1nc(C(=O)Nc3cnccc3N3CCNCC3)n[nH]1)C2] | 434.18 | 435.10 | 2.35 |
| 8 | 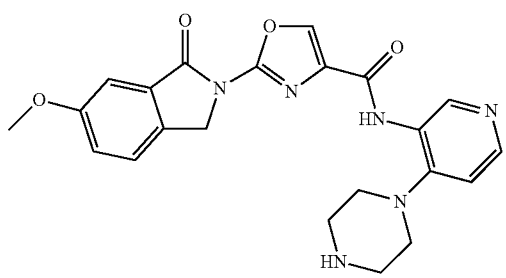 [SMILES: COc1ccc2c(c1)C(=O)N(c1nc(C(=O)Nc3cnccc3N3CCNCC3)co1)C2] | 434.17 | 435.10 | 2.10 |
| 9 | 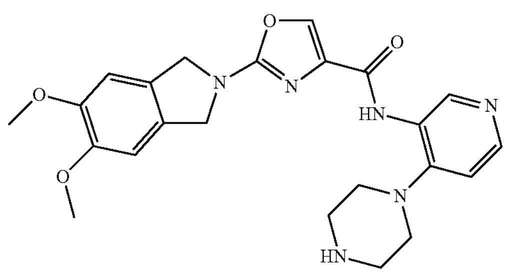 [SMILES: COc1cc2c(cc1OC)CN(c1nc(C(=O)Nc3cnccc3N3CCNCC3)co1)C2] | 450.20 | 451.20 | 2.20 |

Assays
CHK1 SPA Assay

An in vitro assay was developed that utilizes recombinant His-CHK1 expressed in the baculovirus expression system as an enzyme source and a biotinylated peptide based on CDC25C as substrate (biotin-RSGLYRSPSMPENLNRPR).

Materials and Reagents:
1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 µg/mL, stored at −80° C.
3) D-PBS (without CaCl and MgCl): GIBCO, Cat. #14190-144
4) SPA beads: Amersham, Cat. #SPQ0032: 500 mg/vial
  Add 10 mL of D-PBS to 500 mg of SPA beads to make a working concentration of 50 mg/mL. Store at 4° C. Use within 2 week after hydration.
5) 96-Well White Microplate with Bonded GF/B filter: Packard, Cat. #6005177
6) Top seal-A 96 well Adhesive Film: Perkin Elmer, Cat. #6005185
7) 96-well Non-Binding White Polystyrene Plate: Corning, Cat. #6005177
8) $MgCl_2$: Sigma, Cat. #M-8266
9) DTT: Promega, Cat. #V3155
10) ATP, stored at 4° C.: Sigma, Cat. #A-5394
11) $\gamma^{33}$P-ATP, 1000-3000 Ci/mMol: Amersham, Cat. #AH9968
12) NaCl: Fisher Scientific, Cat. #BP358-212
13) $H_3PO_4$ 85% Fisher, Cat. #A242-500
14) Tris-HCL pH 8.0: Bio-Whittaker, Cat. #16-015V
15) Staurosporine, 100 µg: CALBIOCHEM, Cat. #569397
16) Hypure Cell Culture Grade Water, 500 mL: HyClone, Cat. #SH30529.02

Reaction Mixtures:
1) Kinase Buffer: 50 mM Tris pH 8.0; 10 mM $MgCl_2$; 1 mM DTT
2) His-CHK1, In House Lot P976, MW ~30 KDa, stored at −80° C.
   6 nM is required to yield positive controls of ~5,000 CPM. For 1 plate (100 rxn): dilute 8 μL of 235 μg/mL (7.83 μM) stock in 2 mL Kinase Buffer. This makes a 31 nM mixture. Add 20 μL/well. This makes a final reaction concentration of 6 nM.
3) CDC25C Biotinylated peptide.
   Dilute CDC25C to 1 mg/mL (385 μM) stock and store at −20° C. For 1 plate (100 rxn): dilute 10 μL of 1 mg/mL peptide stock in 2 mL Kinase Buffer. This gives a 1.925 μM mix. Add 20 μL/rxn. This makes a final reaction concentration of 385 nM.
4) ATP Mix.
   For 1 plate (100 rxn): dilute 10 μL of 1 mM ATP (cold) stock and 2 μL fresh P33-ATP (20 μCi) in 5 mL Kinase Buffer. This gives a 2 μM ATP (cold) solution; add 50 μL/well to start the reaction. Final volume is 100 μL/rxn so the final reaction concentrations will be 1 μM ATP (cold) and 0.2 μCi/rxn.
5) Stop Solution:
   For 1 plate add: To 10 mL Wash Buffer 2 (2M NaCl 1% $H_3PO_4$): 1 mL SPA bead slurry (50 mg); Add 100 μL/well
6) Wash buffer 1: 2 M NaCl
7) Wash buffer 2: 2 M NaCl, 1% $H_3PO_4$
Assay Procedure:

| Assay Component | Final Concentration | Volume |
| --- | --- | --- |
| CHK1 | 6 nM | 20 μl/rxn |
| Compound (10% DMSO) | — | 10 μl/rxn |
| CDC25C | 0.385 μM | 20 μl/rxn |
| $\gamma^{33}$P-ATP | 0.2 μCi/rxn | 50 μl/rxn |
| Cold ATP | 1 μM | |
| Stop solution SPA beads | 0.5 mg/rxn | 100 μl/rxn* |
| | | 200 μl/rxn** |

*Total reaction volume for assay.
**Final reaction volume at termination of reaction (after addition of stop solution).

1) Dilute compounds to desired concentrations in water/10% DMSO—this will give a final DMSO concentration of 1% in the rxn. Dispense 10 μL/rxn to appropriate wells. Add 10 μL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 μL to each well.
3) Thaw the Biotinylated substrate on ice and dilute in kinase buffer (see Reaction Mixtures). Add 20 μL/well except to negative control wells. Instead, add 20 μL Kinase Buffer to these wells.
4) Dilute ATP (cold) and P33-ATP in kinase buffer (see Reaction Mixtures). Add 50 μL/well to start the reaction.
5) Allow the reaction to run for 2 hours at room temperature.
6) Stop reaction by adding 100 μL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% $H_3PO_4$
11) Allow filter plate to dry 15 min.
12) Put TopSeal-A adhesive on top of filter plate.
13) Run filter plate in Top Count
   Settings: Data mode: CPM
   Radio nuclide: Manual SPA:P33
   Scintillator: Liq/plant
   Energy Range: Low
$IC_{50}$ Determinations
   Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.
CDK2 Assay
Baculovirus Constructions
   Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPD-YAS). The expressed protein was approximately 34 kDa in size.
Enzyme Production
   Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed overnight in 2 liters of kinase buffer containing 50 mM Tris pH 8.0, 1 mM DTT, 10 mM $MgCl_2$, 100 μM sodium orthovanadate and 20% glycerol. Enzyme was stored in aliquots at −70° C.
In Vitro Cyan E/CDK2 Kinase Assay
   Cyclin E/CDK2 kinase assays were performed in low protein binding 96-well plates (Corning Inc, Corning, N.Y.). Enzyme was diluted to a final concentration of 50 μg/mL in kinase buffer containing 50 mM Tris pH 8.0, 10 mM $MgCl_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μL of the 50 μg/mL enzyme solution (1 μg of enzyme) and 20 μl of the 2 μM substrate solution were mixed, then combined with 10 μL of diluted compound in each well for testing. The kinase reaction was started by addition of 50 μL of 2 μM ATP and 0.1 μCi of 33P-ATP (from Amersham, UK). The reaction was allowed to run for 1 hour at room temperature. The reaction was stopped by adding 200 μL of stop buffer containing 0.1% Triton X-100, 1 mM ATP, 5 mM EDTA, and 5 mg/mL streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ Determinations

Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis.

MEK1 Kinase Assay

Full-length active phosphorylated MEK1 was expressed as a 6× histidine tagged protein ($His_6$-MEK1) by baculovirus infection of Hi-Five cells co-infected with a baculovirus expressing untagged constitutively active Raf-1. Several milligrams of active $His_6$-MEK1 was then purified by Ni-NTA affinity chromatography followed by gel filtration chromatography. Full-length murine catalytically inactive ERK2KR, which had the lysine in subdomain II mutated to arginine was used as a substrate. ERK2KR was expressed from vector pET32aRC in IPTG-induced BL21D3 *E. coli* as a biotinylated, 6× histidine and thioredoxin tagged fusion protein and purified by Ni-NTA affinity chromatography followed by Mono Q ion exchange chromatography. Kinase reactions were performed in duplicate in a 96-well plate, 33 μL per well at 25° C. for 15 mins, and consisted of 20 nM $His_6$-MEK1, 2 μM ERK2KR, 2 μM ATP, 10 μCi/μL [γ-$^{33}$P]-ATP, 10 mM $MgCl_2$, 0.01% β-octylglucoside, 1 mM DTT, 20 mM HEPES pH 7.5, 3% DMSO and test compounds ranging from 20 μM down to 0.08 nM. Kinase reactions were stopped by addition of 30 μL of 1.5% o-phosphoric acid, transferred to Millipore Multiscreen-PH plates and incubated for 5 minutes to allow ERK2KR binding. Non-specific activity was estimated from pre-inactivated reactions wherein 30 μL of 1.5% o-phosphoric acid was added per well before addition of enzyme. Stopped plates were washed three times by vacuum filtration with 0.75% o-phosphoric acid followed by two washes with 100% ethanol and air dried. 50 μL of scintillation cocktail was added to each well and $^{33}$P incorporated into ERK2KR was detected using a Wallac Microbeta 1450 JET scintillation counter. Percentage inhibition, $IC_{50}$ and Hill slope values were calculated using ActivityBase software.

General Procedure for MEK1 TdF Assays

1 μM protein was mixed with micromolar concentrations (usually 1-50 μM) of compounds in 20 μl of assay buffer (25 mM HEPES, pH 7.4, 300 mM NaCl, 1 mM DTT, 2% DMSO, Sypro Orange 5×) in a white 96-well PCR plate. The plate is sealed by clear strips and placed in a thermocycler (Chromo4, BioRad). The fluorescence intensities are monitored at every 0.5° C. increment during melting from 25° C. to 95° C. The data are exported into an excel sheet and subject to a custom curve fitting algorithm to derive TdF Kd values. All TdF Kd values have an error margin of ~50% due to uncertainty with the enthalpy change of binding.

In Vitro Aurora TdF Assays

Aurora A Assay

Aurora A kinase assays were performed in low protein binding 384-well plates (Corning Inc). All reagents were thawed on ice. Test compounds were diluted in 100% DMSO to desirable concentrations. Each reaction consisted of 8 nM enzyme (Aurora A, Upstate cat #14-511), 100 nM Tamra-PKAtide (Molecular Devices, 5TAMRA-GRTGRRNSI-COOH), 25 μM ATP (Roche), 1 mM DTT (Pierce), and kinase buffer (10 mM Tris, 10 mM $MgCl_2$, 0.01% Tween 20). For each reaction, 14 μl containing TAMRA-PKAtide, ATP, DTT and kianse buffer were combined with 1 μl diluted compound. The kinase reaction was started by the addition of 5 μl diluted enzyme. The reaction was allowed to run for 2 hours at room temperature. The reaction was stopped by adding 60 μl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

Aurora B Assay

Aurora A kinase assays were performed in low protein binding 384-well plates (Corning Inc). All reagents were thawed on ice. Compounds were diluted in 100% DMSO to desirable concentrations. Each reaction consisted of 26 nM enzyme (Aurora B, invitrogen cat#pv3970), 100 nM Tamra-PKAtide (Molecular Devices, 5TAMRA-GRTGRRNSI-COOH), 50 μM ATP (Roche), 1 mM DTT (Pierce), and kinase buffer (10 mM Tris, 10 mM $MgCl_2$, 0.01% Tween 20). For each reaction, 14 μl containing TAMRA-PKAtide, ATP, DTT and kianse buffer were combined with 1 μl diluted compound. The kinase reaction was started by the addition of 5 μl diluted enzyme. The reaction was allowed to run for 2 hours at room temperature. The reaction was stopped by adding 60 μl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

$IC_{50}$ Determinations

Dose-response curves were plotted from inhibition data generated each in duplicate, from 8-point serial dilutions of test compounds. Concentration of compound was plotted against kinase activity, calculated by degree of fluorescent polarization. To generate $IC_{50}$ values, the dose-response curves were then fitted to a standard sigmoidal curve and $IC_{50}$ values were derived by nonlinear regression analysis.

The compounds of the present invention exhibited Chk1 $IC_{50}$ values ranging from about 1 nM to about 50 μM or higher, Chk2 $IC_{50}$ values ranging from about 0.8 μM to about 50 μM or higher, CDK2 $IC_{50}$ values ranging from about 2.3 μM to about 50 μM or higher, and Chk1 $EC_{50}$ values ranging from about 0.15 μM to about 1.5 μM or higher.

What is claimed is:

1. A heterocyclic amide derivative of Formula (I):

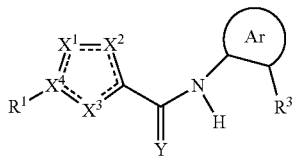

Formula (I)

wherein:
the moiety

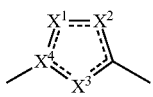

is selected from the group consisting of

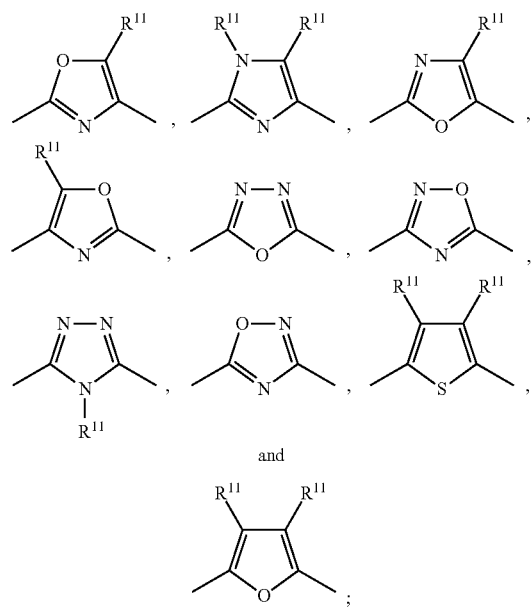

Ar is $C_{6-10}$arylene or a 5-10 membered heteroarylene comprising one ring or two rings fused together at adjacent ring atoms comprising 1-3 heteroatoms independently selected from O, S, and N, said $C_{6-10}$arylene and 5-10 membered heteroarylene being joined to $NR^2$ and $R^3$ via any two adjacent ring carbons on said $C_{6-10}$arylene and 5-10 membered heteroarylene, and being optionally substituted with one or more substituents independently selected from $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^4$, —$S(O)R^4$, —$S(O)_2R^4$, —$COR^4$, —$CO_2R^4$, —$CONHR^4$, —$CON(R^4)_2$, —$NHCOR^4$, CN, and $NO_2$, wherein said $C_{1-6}$alkyl, $C_{3-8}$cycloalkyl and $C_{1-6}$alkyloxy are optionally substituted with one or more halogens, and wherein said $C_{6-10}$aryl and $C_{6-10}$aryloxy are optionally substituted with one or more substituents independently selected from halogen, hydroxyl, $C_{1-6}$alkyl, and $C_{1-6}$alkyloxy;

$R^1$ is $CONR^5R^6$, $NR^7COR^8$, $C_{6-10}$aryl or a 4-10 membered saturated or unsaturated heterocyclic ring system comprising one ring or two rings fused together at adjacent ring atoms comprising a N atom and optionally comprising one or more further heteroatoms independently selected from O, S, and $N(R^{1a})_m$, said $C_{6-10}$aryl and 4-10 membered saturated or unsaturated heterocyclic ring system being optionally substituted with one or more substituents independently selected from $C_{1-6}$alkyl, $C_{3-8}$cycloalkyl, $C_{1-6}$alkyloxy, hydroxy$C_{1-6}$alkoxy, $C_{1-2}$alkoxy$C_{1-6}$alkoxy, $(C_{1-6}$alkyl$)_2$-N—$C_{1-6}$alkoxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^9$, —$S(O)R^9$, —$S(O)_2R^9$, —$COR^9$, —$CO_2R^9$, —$CON(R^9)_2$, —$NHCOR^9$, CN, and $NO_2$, or two substituents on the same carbon form together with said carbon a carbonyl, wherein said $C_{1-6}$alkyl, $C_{3-8}$cycloalkyl, and $C_{1-6}$alkyloxy are optionally substituted with one or more halogens, and wherein said $C_{6-10}$aryl and $C_{6-10}$aryloxy are optionally substituted with one or two substituents independently selected from halogen, hydroxyl, $C_{1-6}$alkyl, and $C_{1-6}$alkyloxy;

$R^{1a}$ is H or $C_{1-6}$alkyl;

$R^2$ is H or $C_{1-6}$alkyl;

$R^3$ is $C_{6-10}$aryl or a 4-12 membered saturated or unsaturated heterocyclic ring system comprising one ring or two rings fused together at adjacent ring atoms or comprising two rings linked together at the same ring atom thereby forming a spirocyclic ring, said 4-12 membered heterocyclic ring system comprising a N atom and optionally comprising one or more further heteroatoms independently selected from O, S, and $N(R^{3a}a)_n$, said $C_{6-10}$aryl and 4-12 membered saturated or unsaturated heterocyclic ring system being optionally substituted with one or more substituents independently selected from $C_{1-6}$alkyl optionally substituted with hydroxyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$S(O)R^{10}$, —$S(O)_2R^{10}$, —$COR^{10}$, —$CO_2R^{10}$, —$CON(R^{10})_2$, —$NHCOR^{10}$, CN, and $NO_2$, or two substituents on the same carbon form together with said carbon a carbonyl, wherein said $C_{1-6}$alkyl and $C_{1-6}$alkyloxy are optionally substituted with one or more halogens, and wherein said $C_{6-10}$aryl and $C_{6-10}$aryloxy are optionally substituted with one or two substituents independently selected from halogen, hydroxyl, $C_{1-6}$alkyl, and $C_{1-6}$alkyloxy;

$R^{3a}$ is H or $C_{1-6}$alkyl;

each $R^4$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{4a})_p$, said $C_{1-6}$alkyl, $C_{3-8}$cycloalkyl, $C_{1-6}$alkyloxy and $C_{3-8}$cycloalkyloxy being optionally substituted with one or more halogens and said $C_{6-10}$aryl, $C_{6-10}$aryloxy and 4-7 membered saturated or unsaturated heterocyclic ring being optionally substituted with one or more substituents independently selected from halogen, hydroxyl, $C_{1-6}$alkyl, and $C_{1-6}$alkyloxy;

$R^{4a}$ is H or $C_{1-6}$alkyl;

$R^5$ and $R^6$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatoms independently selected from O, S, and $N(R^{5a})_q$, said $C_{1-6}$alkyl and $C_{3-8}$cycloalkyl being optionally substituted with one or more halogens, and said $C_{6-10}$aryl, $C_{6-10}$aryl$C_{1-2}$alkyl, and 4-10 membered saturated or unsaturated heterocyclic ring system being optionally substituted with one or more substituents independently selected from halogen, hydroxyl, $C_{1-6}$alkyl, and $C_{1-6}$alkyloxy, or $R^5$ and $R^6$ together with the N to which they are bonded form a 4-7 membered heterocyclic ring optionally comprising a further heteroatom selected from O, S, and $N(R^{6a})_r$;

$R^{5a}$ and $R^{6a}$ are independently H or $C_{1-6}$alkyl;

$R^7$ and $R^8$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatoms independently selected from O, S, and $N(R^{7a})_s$, said $C_{1-6}$alkyl and $C_{3-8}$cycloalkyl being optionally substituted with one or more halogens, and said $C_{6-10}$aryl, $C_{6-10}$aryl$C_{1-2}$alkyl, and 4-10 membered saturated or unsaturated heterocyclic ring system being optionally substituted with one or more substituents independently selected from halogen, hydroxyl, $C_{1-6}$alkyl, and $C_{1-6}$alkyloxy;

$R^{7a}$ is H or $C_{1-6}$alkyl;

each $R^9$ is independently $C_{1-6}$alkyl, $C_{3-6}$cycloalkyl, $C_{1-6}$alkyloxy, $C_{3-6}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{9a})_t$, said $C_{1-6}$alkyl, $C_{3-6}$cycloalkyl, $C_{1-6}$alkyloxy, and $C_{3-6}$cycloalkyloxy being optionally substituted with one or more halogens, and said $C_{6-10}$aryl, $C_{6-10}$aryloxy, and 4-7 membered saturated or unsaturated heterocyclic ring being optionally substituted with one or more substituents selected from halogen, hydroxyl, $C_{1-6}$alkyl, and $C_{1-6}$alkyloxy;

$R^{9a}$ is H or $C_{1-6}$alkyl;

each $R^{10}$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{10a})_u$, said $C_{1-6}$alkyl, $C_{3-8}$cycloalkyl, $C_{1-6}$alkyloxy, and $C_{3-8}$cycloalkyloxy being optionally substituted with one or more halogens, and said $C_{6-10}$aryl, $C_{6-10}$aryloxy, and 4-7 membered saturated or unsaturated heterocyclic ring being optionally substituted with one or more substituents selected from halogen, hydroxyl, $C_{1-6}$alkyl and $C_{1-6}$alkyloxy;

$R^{10a}$ is H or $C_{1-6}$alkyl;

each $R^{11}$ is independently H, $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{11a})_w$, said $C_{1-6}$alkyl, $C_{3-8}$cycloalkyl, $C_{1-6}$alkyloxy, and $C_{3-8}$cycloalkyloxy being optionally substituted with one or more halogens, and said $C_{6-10}$aryl, $C_{6-10}$aryloxy, and 4-7 membered saturated or unsaturated heterocyclic ring being optionally substituted with one or more substituents selected from halogen, hydroxyl, $C_{1-6}$alkyl, and $C_{1-6}$alkyloxy;

Y is O, S, or —$NR^{12}$;

$R^{12}$ is H or $C_{1-4}$alkyl; and m, n, p, q, r, s, t, u, v, and w are independently 0 or 1, or a pharmaceutically acceptable salt thereof.

2. The heterocyclic amide derivative according to claim 1, wherein Ar is phenylene or pyridylene optionally substituted with one or more substituents independently selected from $C_{1-6}$alkyl, $C_{1-6}$alkyloxy, and halogen.

3. The heterocyclic amide derivative according to claim 2, wherein Ar is pyridylene optionally substituted with methyl, methoxy, chloro, or fluoro.

4. The heterocyclic amide derivative according to claim 1, wherein $R^1$ is $R^{13}$ is one or more optional substituents independently selected from $C_{1-6}$alkyl, $C_{1-6}$alkyloxy, amino, halogen, $C_{1-2}$alkyl-O—$C_{1-2}$alkylene-O—, HO—$C_{1-2}$alkylene-O—, and $(C_{1-6}alkyl)_2$-N—$C_{1-2}$alkylene-O—, and x is an integer from 1-3.

5. The heterocyclic amide derivative according to claim 4, wherein $R^1$ is $R^{13}$ is one or more optional substituents independently selected from methoxy, ethoxy, methyl, amino, halogen, and $H_3C$—$(CH_2)_2$—O—, and x is an integer from 1-2.

6. The heterocyclic amide derivative according to claim 1, wherein $R^2$ is H.

7. The heterocyclic amide derivative according to claim 1, wherein $R^3$ is

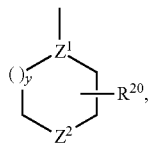

$Z^1$ is CH or N, $Z^2$ is $CHR^{20a}$ or $NR^{20a}$, y is an integer from 1-3, $R^{20}$ is one or two optional substituents selected from $C_{1-6}$alkyl optionally substituted with hydroxyl, $C_{1-6}$alkyloxy, amino, hydroxyl, $NH(C_{1-6}alkyl)$, and $N(C_{1-6}alkyl)_2$, and $R^{20a}$ is H or $C_{1-6}$alkyl.

8. The heterocyclic amide derivative according to claim 7, wherein $R^3$ is

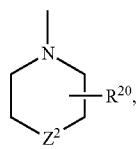

$Z^2$ is $CH_2$ or NH, and $R^{20}$ is one or two optional substituents independently selected from methyl, hydroxymethyl, methoxy, amino, hydroxyl, methylamino, and dimethylamino.

9. The heterocyclic amide derivative according to claim 1, wherein Y is O.

10. A heterocyclic amide derivative selected from the group consisting of:

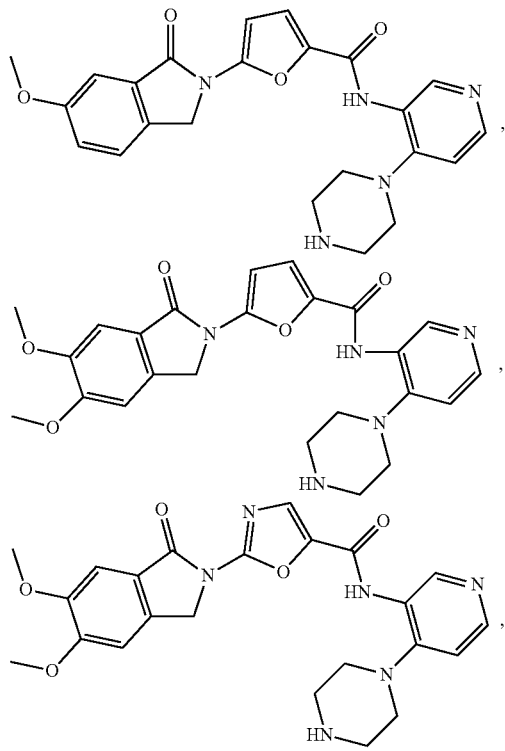

-continued

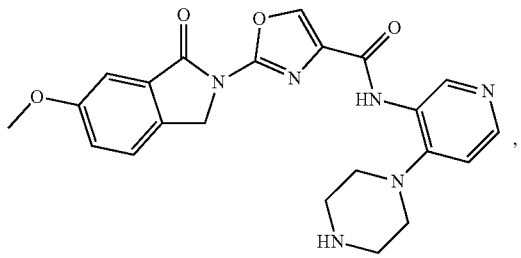

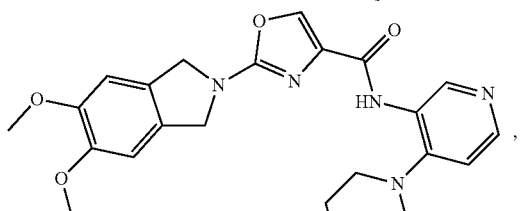

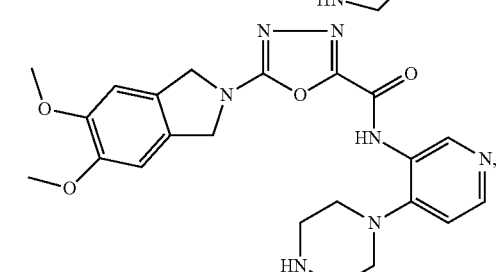

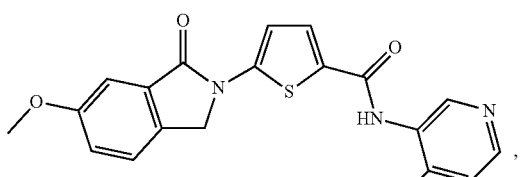

and

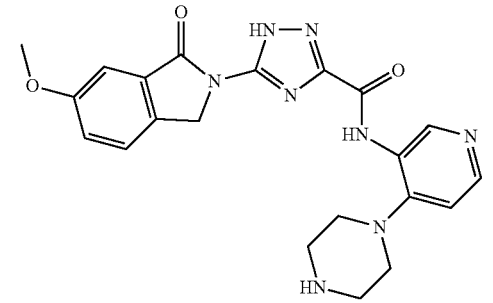

or a pharmaceutically acceptable salt thereof.

11. A pharmaceutical composition comprising a heterocyclic amide derivative according to claim 1, or a pharmaceutically acceptable salt thereof, in combination with at least one pharmaceutically acceptable carrier.

12. A heterocyclic amide derivative of Formula (I):

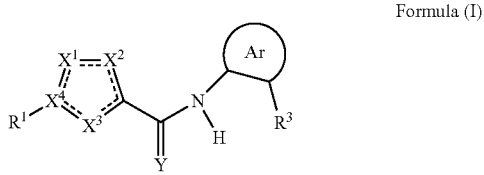

Formula (I)

wherein:
the moiety

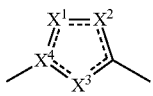

is selected from the group consisting of

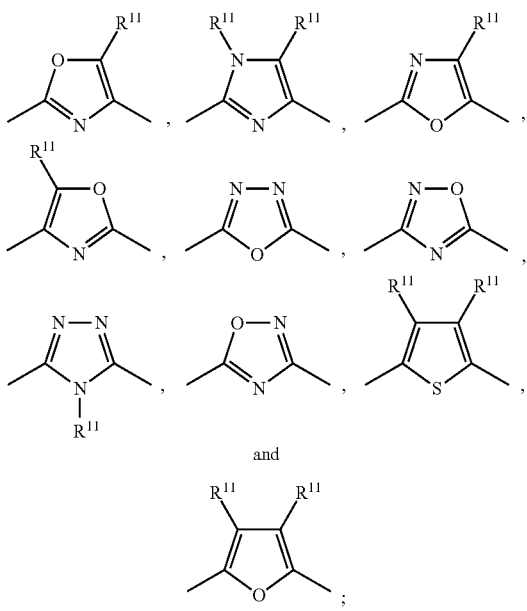

Ar is a 5-10 membered heteroarylene comprising one ring or two rings fused together at adjacent ring atoms comprising 1-3 heteroatoms independently selected from O, S, and N, said 5-10 membered heteroarylene being joined to $NR^2$ and $R^3$ via any two adjacent ring carbons on said 5-10 membered heteroarylene, and being optionally substituted with one or more substituents independently selected from $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^4$, —$S(O)R^4$, —$S(O)_2R^4$, —$COR^4$, —$CO_2R^4$, —$CONHR^4$, —$CON(R^4)_2$, —NHCOR$^4$, CN, and $NO_2$, wherein said $C_{1-6}$alkyl, $C_{3-8}$cycloalkyl and $C_{1-6}$alkyloxy are optionally substituted with one or more halogens, and wherein said $C_{6-10}$aryl and $C_{6-10}$aryloxy are optionally substituted with one or more substituents independently selected from halogen, hydroxyl, $C_{1-6}$alkyl, and $C_{1-6}$alkyloxy;

$R^1$ is a 4-10 membered saturated or unsaturated heterocyclic ring system comprising one ring or two rings fused together at adjacent ring atoms comprising an N atom and optionally comprising one or more further heteroatoms independently selected from O, S, and $N(R^{1a})_m$, said 4-10 membered saturated or unsaturated heterocyclic ring system being optionally substituted with one or more substituents independently selected from $C_{1-6}$alkyl, $C_{3-8}$cycloalkyl, $C_{1-6}$alkyloxy, hydroxy$C_{1-6}$alkoxy, $C_{1-2}$alkoxy$C_{1-6}$alkoxy, $(C_{1-6}$alkyl$)_2$-N—$C_{1-6}$alkoxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^9$, —$S(O)R^9$, —$S(O)_2R^9$, —$COR^9$, —$CO_2R^9$, —$CON(R^9)_2$, —NHCOR$^9$, CN, and $NO_2$, or two substituents on the same carbon form together with said carbon a carbonyl, wherein said $C_{1-6}$alkyl, $C_{3-8}$cycloalkyl, and $C_{1-6}$alkyloxy are optionally substituted with one or more halogens, and wherein said $C_{6-10}$aryl and $C_{6-10}$aryloxy are optionally substituted with one or two substituents independently selected from halogen, hydroxyl, $C_{1-6}$alkyl, and $C_{1-6}$alkyloxy;

$R^{1a}$ is H or $C_{1-6}$alkyl;

$R^2$ is H or $C_{1-6}$alkyl;

$R^3$ is a 4-12 membered saturated or unsaturated heterocyclic ring system comprising one ring or two rings fused together at adjacent ring atoms or comprising two rings linked together at the same ring atom thereby forming a spirocyclic ring, said 4-12 membered heterocyclic ring system comprising a N atom and optionally comprising one or more further heteroatoms independently selected from O, S, and $N(R^{3a})_n$, said 4-12 membered saturated or unsaturated heterocyclic ring system being optionally substituted with one or more substituents independently selected from $C_{1-6}$alkyl optionally substituted with hydroxyl, $C_{3-8}$cycloalkyl, $C_{1-6}$alkyloxy, $C_{3-8}$cycloalkyloxy, $C_{6-10}$aryl, $C_{6-10}$aryloxy, halogen, hydroxyl, $NH_2$, —$NHC_{1-6}$alkyl, —$N(C_{1-6}$alkyl$)_2$, —$SR^{10}$, —$S(O)R^{10}$, —$S(O)_2R^{10}$, —$COR^{10}$, —$CO_2R^{10}$, —$CON(R^{10})_2$, —NHCOR$^{10}$, CN, and $NO_2$, or two substituents on the same carbon form together with said carbon a carbonyl, wherein said $C_{1-6}$alkyl and $C_{1-6}$alkyloxy are optionally substituted with one or more halogens, and wherein said $C_{6-10}$aryl and $C_{6-10}$aryloxy are optionally substituted with one or two substituents independently selected from halogen, hydroxyl, $C_{1-6}$alkyl, and $C_{1-6}$alkyloxy;

$R^{3a}$ is H or $C_{1-6}$alkyl;

each $R^4$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{4a})_p$, said $C_{1-6}$alkyl, $C_{3-8}$cycloalkyl, $C_{1-6}$alkyloxy and $C_{3-8}$cycloalkyloxy being optionally substituted with one or more halogens, and said $C_{6-10}$aryl, $C_{6-10}$aryloxy, and 4-7 membered saturated or unsaturated heterocyclic ring being optionally substituted with one or more substituents independently selected from halogen, hydroxyl, $C_{1-6}$alkyl, and $C_{1-6}$alkyloxy;

$R^{4a}$ is H or $C_{1-6}$alkyl;

$R^5$ and $R^6$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatoms independently selected from O, S, and $N(R^{5a})_q$, said $C_{1-6}$alkyl and $C_{3-8}$cycloalkyl being optionally substituted with one or more halogens, and said $C_{6-10}$aryl, $C_{6-10}$aryl$C_{1-2}$alkyl and 4-10 membered saturated or unsaturated heterocyclic ring system being optionally substituted with one or more substituents independently selected from halogen, hydroxyl, $C_{1-6}$alkyl and $C_{1-6}$alkyloxy, or $R^5$ and $R^6$ together with the N to which they are bonded form a 4-7 membered heterocyclic ring optionally comprising a further heteroatom selected from O, S, and $N(R^{6a})_r$;

$R^{5a}$ and $R^{6a}$ are independently H or $C_{1-6}$alkyl;

$R^7$ and $R^8$ are independently H, $C_{1-6}$alkyl, $C_{3-8}$cycloalkyl, $C_{6-10}$aryl, $C_{6-10}$aryl$C_{1-2}$alkyl or a 4-10 membered saturated or unsaturated heterocyclic ring system comprising one ring or two rings fused together at adjacent ring atoms and comprising one or more heteroatoms independently selected from O, S, and $N(R^{7a})_s$, said $C_{1-6}$alkyl and $C_{3-8}$cycloalkyl being optionally substituted with one or more halogens, and said $C_{6-10}$aryl, $C_{6-10}$aryl$C_{1-2}$alkyl, and 4-10 membered saturated or unsaturated heterocyclic ring system being optionally substituted with one or more substituent independently selected from halogen, hydroxyl, $C_{1-6}$alkyl, and $C_{1-6}$alkyloxy;

$R^{7a}$ is H or $C_{1-6}$alkyl;

each $R^9$ is independently $C_{1-6}$alkyl, $C_{3-6}$cycloalkyl, $C_{1-6}$alkyloxy, $C_{3-6}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{9a})_t$, said $C_{1-6}$alkyl, $C_{3-6}$cycloalkyl, $C_{1-6}$alkyloxy, and $C_{3-6}$cycloalkyloxy being optionally substituted with one or more halogens, and said $C_{6-10}$aryl, $C_{6-10}$aryloxy and 4-7 membered saturated or unsaturated heterocyclic ring being optionally substituted with one or more substituents selected from halogen, hydroxyl, $C_{1-6}$alkyl, and $C_{1-6}$alkyloxy;

$R^{9a}$ is H or $C_{1-6}$alkyl;

each $R^{10}$ is independently $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{10a})_u$, said $C_{1-6}$alkyl, $C_{3-8}$cycloalkyl, $C_{1-6}$alkyloxy, and $C_{3-8}$cycloalkyloxy being optionally substituted with one or more halogens, and said $C_{6-10}$aryl, $C_{6-10}$aryloxy and 4-7 membered saturated or unsaturated heterocyclic ring being optionally substituted with one or more substituents selected from halogen, hydroxyl, $C_{1-6}$alkyl, and $C_{1-6}$alkyloxy;

$R^{10a}$ is H or $C_{1-6}$alkyl;

each $R^{11}$ is independently H, $C_{1-6}$alkyl, $C_{3-8}$cycloalkyl, $C_{1-6}$alkyloxy, $C_{3-8}$cycloalkyloxy, $C_{6-10}$aryl, $C_{6-10}$aryloxy or a 4-7 membered saturated or unsaturated heterocyclic ring comprising one or more heteroatoms independently selected from O, S, and $N(R^{11a})_w$, said $C_{1-6}$alkyl, $C_{3-8}$cycloalkyl, $C_{1-6}$alkyloxy, and $C_{3-8}$cycloalkyloxy being optionally substituted with one or more halogens, and said $C_{6-10}$aryl, $C_{6-10}$aryloxy, and 4-7 membered saturated or unsaturated heterocyclic ring being optionally substituted with one or more substituents selected from halogen, hydroxyl, $C_{1-6}$alkyl, and $C_{1-6}$alkyloxy;

Y is O, S, or $-NR^{12}$;

$R^{12}$ is H or $C_{1-4}$alkyl; and m, n, p, q, r, s, t, u, v, and w are independently 0 or 1, or a pharmaceutically acceptable salt thereof.

13. A heterocyclic amide derivative according to claim 12, wherein the moiety

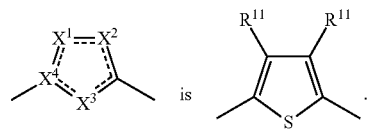

is

14. The heterocyclic amide derivative according to claim 12 wherein Ar is pyridylene optionally substituted with methyl, methoxy, chloro, or fluoro.

15. The heterocyclic amide derivative according to claim 12, wherein $R^1$ is

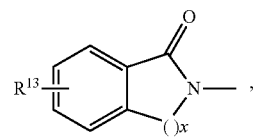

$R^{13}$ is one or more optional substituents independently selected from methoxy, ethoxy, methyl, amino, halogen and $H_3C-(CH_2)_2-O-$, and x is an integer from 1-2.

16. A heterocyclic amide derivative according to claim 14, wherein $R^3$ is

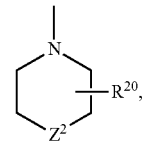

$Z^2$ is $CH_2$ or NH, and $R^{20}$ is one or two optional substituents independently selected from methyl, hydroxymethyl, methoxy, amino, hydroxyl, methylamino, and dimethylamino.

17. A heterocyclic amide derivative according to the following formula

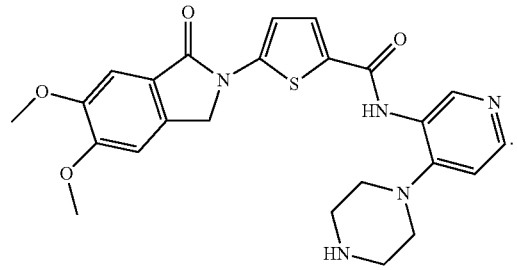 [SMILES: COc1cc2c(cc1OC)C(=O)N(c1ccc(C(=O)Nc3cnccc3N3CCNCC3)s1)C2]

18. A pharmaceutical composition comprising a heterocyclic amide derivative according to claim 17, or a pharmaceutically acceptable salt thereof, in combination with at least one pharmaceutically acceptable carrier.

* * * * *